(12) United States Patent
Geneste et al.

(10) Patent No.: US 8,431,567 B2
(45) Date of Patent: Apr. 30, 2013

(54) SUBSTITUTED OXINDOLE DERIVATIVES AND THEIR USE AS VASOPRESSIN AND/OR OXYTOCIN RECEPTOR LIGANDS

(75) Inventors: Herve Geneste, Ludwigshafen (DE); Thorsten Oost, Biberach an der Riss (DE); Astrid Netz, Ludwigshafen (DE); Charles W. Hutchins, Green Oaks, IL (US); Wolfgang Wernet, Ludwigshafen (DE); Wilfred Lubisch, Heidelberg (DE); Liliane Unger, Ludwigshafen (DE); Wilfried Hornberger, Ludwigshafen (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

(21) Appl. No.: 12/438,696

(22) PCT Filed: Aug. 24, 2007

(86) PCT No.: PCT/EP2007/058839
§ 371 (c)(1),
(2), (4) Date: Aug. 31, 2009

(87) PCT Pub. No.: WO2008/025735
PCT Pub. Date: Mar. 6, 2008

(65) Prior Publication Data
US 2009/0318406 A1 Dec. 24, 2009

Related U.S. Application Data

(60) Provisional application No. 60/958,591, filed on Jul. 6, 2007.

(30) Foreign Application Priority Data

Aug. 26, 2006 (DE) .......................... 10 2006 040 915

(51) Int. Cl.
*A61K 31/551* (2006.01)
*A61K 31/496* (2006.01)
*A61K 31/4439* (2006.01)
*C07D 243/08* (2006.01)
*C07D 401/14* (2006.01)
*C07D 401/02* (2006.01)

(52) U.S. Cl.
USPC ...... 514/218; 514/253.09; 514/339; 540/575; 544/364; 546/277.7

(58) Field of Classification Search ............ 514/210.16, 514/253.09, 339, 218, 210.01; 544/364; 546/277.7; 540/597
See application file for complete search history.

(56) References Cited

U.S. PATENT DOCUMENTS

| 5,594,023 A | 1/1997 | Wagnon et al. |
| 6,090,818 A | 7/2000 | Foulon et al. |
| 2003/0109545 A1 | 6/2003 | Serradeil-Le-Gal et al. |
| 2003/0139413 A1 | 7/2003 | Schoentjes et al. |
| 2003/0162767 A1 | 8/2003 | Roux et al. |
| 2004/0180878 A1 | 9/2004 | DiMalta et al. |
| 2009/0005397 A1 | 1/2009 | Lubisch et al. |

FOREIGN PATENT DOCUMENTS

| WO | WO93/15051 | 5/1993 |
| WO | WO01/55130 | 8/2001 |
| WO | WO2005/030755 | 4/2005 |
| WO | WO 2006/080574 A1 * | 8/2006 |

OTHER PUBLICATIONS

Wolff et al. (Burger's Medicinal Chemistry, 5th Ed., vol. 1, pp. 975-977, 1994).*
Testa, Bernard, Biochemical Pharmacology, Prodrug Research: futile or fertile? 68 (2004) 2097-2106.*
Ettmayer, Peter, Medicinal Chemistry, Lessons Learned from Marketed and Investigational Prodrugs, 47(10), (2004) 2394-2404.*
Thibonnier, M. 1998. Exp. Opin. Invest. Drugs. (5), 729-740.
Roche Encyclopedia of Medicine, Third Edition, 1993, Definition of oxytocine, p. 1247. (English translation).
Database CA, Chemical Abstracts Service, Columbus, Ohio, US; Sekiguchi, Yoshinori et al.: "Preparation of 1,3-dihydro-2H-indol-2-one compounds and pyrrolidin-2-one compound fused with aromatic heterocycle as antagonists of arginine-vasopressin V1b receptor" XP002462422, dated Dec. 20, 2007, pp. 1-2.

* cited by examiner

*Primary Examiner* — Kristin Bianchi
(74) *Attorney, Agent, or Firm* — Lisa V. Mueller; Michael Best & Friedrich LLP

(57) ABSTRACT

The present invention relates to novel oxindole derivatives of general formula (I),

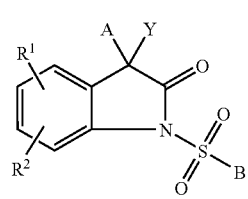

(I)

in which the substituents $R^1$, $R^2$, A, B and Y are as defined in claim 1, medicinal products containing them and use thereof for the prophylaxis and/or treatment of vasopressin-dependent and/or oxytocin-dependent diseases.

22 Claims, No Drawings

SUBSTITUTED OXINDOLE DERIVATIVES AND THEIR USE AS VASOPRESSIN AND/OR OXYTOCIN RECEPTOR LIGANDS

RELATED APPLICATIONS

This application is a 371 of PCT Application No. 371 of PCT/EP2007/058839, filed Aug. 24, 2007, which claims priority to U.S. Patent Application Ser. No. 60/958,591, filed Jul. 6, 2007 and to German Patent Application No. 102006040915.9, filed Aug. 26, 2006, the contents of all of which are herein incorporated by reference in their entireties.

The present invention relates to novel substituted oxindole derivatives, medicinal products containing them and use thereof for the treatment of diseases.

Vasopressin is an endogenous hormone, which exerts a wide range of effects on organs and tissues. The vasopressin system is presumed to play a role in various pathological states, for example heart failure and hypertension. Currently three receptors (V1a, V1b or V3 and V2) are known, via which vasopressin imparts its numerous effects. Therefore antagonists of these receptors are being investigated as possible new therapeutic approaches for the treatment of diseases (M. Thibonnier, Exp. Opin. Invest. Drugs 1998, 7(5), 729-740).

Oxytocin is a hormone that is formed in neurosecretory neurons of the hypothalamus and—bound to neurophysins—is transported to the neurohypophysis, where it is stored. Oxytocin stimulates the contraction of the uterine muscles and of the myoepithelial cells of the mammary gland (milk ejection); the readiness of the uterus to contract is varied by oestrogens (promoting action) and gestagens (inhibiting action). Oxytocin is broken down by the enzyme oxytocinase. Oxytocin finds application in obstetrics (e.g. for inducing labour, in postpartum uterine atony) (cited from: Roche Lexikon Medizin 5th edition).

The present application describes novel substituted oxindoles, which have an aryl-sulphonyl group in position 1. 1-Phenylsulphonyl-1,3-dihydro-2H-indol-2-ones have already been described as ligands of the vasopressin receptors. In WO 93/15051, WO95/18105, WO 98/25901, WO 01/55130, WO 01/55134, WO 01/164668 and WO 01/98295, derivatives are described, which were derived from the oxindole main structure and have arylsulphonyl groups in position 1. These compounds differ markedly in the substitution in position 3.

In particular, WO 93/15051 and WO 98/25901 describe 1-phenylsulphonyl-1,3-dihydro-2H-indol-2-ones as ligands of the vasopressin receptors, in which the oxindole core is substituted at position 3 with two alkyl radicals, which can also be a cycloalkyl radical (spiro union). As an alternative, the spiro ring can contain heteroatoms, such as oxygen and nitrogen (optionally with substituents).

WO 95/18105 describes 1-phenylsulphonyl-1,3-dihydro-2H-indol-2-ones as ligands of the vasopressin receptors, which have a nitrogen atom at position 3. In addition, radicals, which can be alkyl, cycloalkyl, phenyl or benzyl radicals (optionally with substituents in each case) are bound at position 3.

WO 03/008407 describes 1-phenylsulphonyl-oxindoles in which pyridylpiperazines are bound at position 3 via an oxycarbonyl group on the oxindole.

The problem of the present invention is to make available further compounds for the treatment or prophylaxis of various vasopressin-dependent or oxytocin-dependent diseases, which display high and selective activity, preferably in particular with respect to the vasopressin $V_{1B}$ receptor.

This problem is solved in that at least one compound of general formula (I),

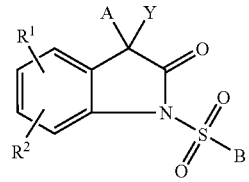

in which

A is $C_6$-$C_{10}$-aryl, which can be substituted with one, two, three or four residues selected from the group comprising $R_A^1$, $R_A^2$, $R_A^3$ and/or $R_A^4$, in which $R_A^1$, $R_A^2$, $R_A^3$ and $R_A^4$, independently of one another and regardless of their respective occurrence, are selected from the group comprising hydrogen, chlorine, bromine, iodine, fluorine, CN, in each case optionally substituted $OR_A^5$, $COR_A^5$, $COOR_A^5$, $SR_A^5$, $C_3$-$C_7$-cycloalkyl, $OCOR_A^5$, $SO_2NR_A^6R_A^7$, $CONR_A^6R_A^7$, $C_0$-$C_4$-alkylene-CN, $C_1$-$C_6$-haloalkyl, $C_1$-$C_6$-haloalkoxy, $NO_2$, $C_0$-$C_4$-alkylene-$OR_A^5$, $C_1$-$C_6$-alkyl, $C_2$-$C_6$-alkenyl, $C_2$-$C_6$-alkynyl, $C_2$-$C_6$-alkenyloxy, $C_2$-$C_6$-alkynyloxy, $C_1$-$C_4$-alkylthio, $C_0$-$C_4$-alkylene-$COR_A^5$, $SO_2R_A^5$, $C_0$-$C_4$-alkylene-$COOR_A^5$, O—$C_1$-$C_4$-alkylene-$COOR_A^5$, $C_0$-$C_4$-alkylene-$SR_A^5$, $C_0$-$C_4$-alkylene-$C_3$-$C_7$-cycloalkyl, $C_0$-$C_4$-alkylene-$OCOR_A^5$, $C_0$-$C_4$-alkylene-$SO_2NR_A^6R_A^7$, $C_0$-$C_4$-alkylene-$NR_A^6R_A^7$, $C_0$-$C_4$-alkylene-$CONR_A^6R_A^7$, $C_1$-$C_4$-alkylene-$OCONR_A^6R_A^7$, $C_1$-$C_4$-alkylene-$SOR_A^5$, $C_1$-$C_4$-alkylene-$SO_2R_A^5$, $NHCOO$-$C_0$-$C_4$-alkylene-aryl, $NHCOOH$, $NH_2$, $NH(C_1$-$C_4$-alkyl), $N(C_1$-$C_4$-alkyl)$_2$, $NHCHO$, $NHCONH_2$, $N(C_0$-$C_4$-alkylene)$CONH_2$, $N(C_0$-$C_4$-alkylene)$CONH(C_1$-$C_4$-alkyl), $NHCOCH_3$, $NO_2$, $(CH_2)_{0-2}$—OH, O—$C_1$-$C_6$-alkyl, $(CH_2)_{0-2}$—O—$C_1$-$C_4$-alkyl, O—$C_0$-$C_4$-alkylene-phenyl, phenyl, where two of the residues $R_A^1$, $R_A^2$, $R_A^3$ and $R_A^4$ positioned adjacent ("ortho") to one another can also form an, optionally substituted, fused saturated, unsaturated and/or aromatic 3- to 10-membered carbon ring or a cyclic acetal —O—$CH_2$—$CH_2$—O— or —O—$CH_2$—O— or a fused furan ring (—O—CH=CH—), and in which $R_A^5$ regardless of its respective occurrence denotes hydrogen, a linear or branched $C_1$-$C_6$-alkyl residue, or a linear or branched, optionally substituted $C_2$-$C_6$-alkenyl, $C_2$-$C_6$-alkynyl, $C_3$-$C_7$-cycloalkyl, $C_1$-$C_4$-alkylene-$C_3$-$C_7$-cycloalkyl or $C_1$-$C_4$-alkylene-($C_6$-$C_{10}$)-aryl residue, $R_A^6$ and $R_A^7$, independently of one another and regardless of their respective occurrence, denote hydrogen, a linear or branched, optionally substituted $C_1$-$C_6$-alkyl, $C_2$-$C_6$-alkenyl, $C_2$-$C_6$-alkynyl, $C_1$-$C_5$-alkylene-$C_1$-$C_4$-alkoxy, $C_3$-$C_7$-cycloalkyl, $C_1$-$C_4$-alkylene-$C_3$-$C_7$-cycloalkyl, $C_1$-$C_4$-alkylene-aryl residue, or an —$SO_2R_A^5$, —$CO_2R_A^5$, —CO—$NR_A^5R_A^5$, or —$COR_A^5$ residue, or together with the nitrogen atom to which they are bonded are a 3-, 4-, 5-, 6- or 7-membered, saturated or unsaturated nitrogen heterocycle which may have a further heteroatom from the group of O, S and $NR_A^{76}$ and which is unsubstituted and/or may have 1, 2, 3 or 4 substituents $R_A^{77}$, where $R_A^{76}$ is selected from $C_1$-$C_6$-alkyl, $C_1$-$C_6$-haloalkyl, $C_1$-$C_6$-alkoxy, $C_1$-$C_6$-haloalkoxy, $C_3$-$C_6$-cycloalkyl, $C_3$-$C_6$-cycloalkoxy, $C_1$-$C_6$-alkylcarbonyl and $C_1$-$C_6$-haloalkylcarbonyl, $R_A^{77}$ has one of the meanings indicated for $R_A^{76}$, or is halogen, and where 2 substituents $R_A^{77}$ bonded to a C atom of the nitrogen heterocycle may also form a carbonyl oxygen, and B is an aromatic or partially aromatic $C_6$-$C_{10}$ single or fused double ring, which can be substituted with at most four residues selected from the group comprising $R_B^1$, $R_B^2$, $R_B^3$, and $R_B^4$, where $R_B^1$, $R_B^2$, $R_B^3$ and $R_B^4$ independently of one another and regardless of their respective occurrence, are selected from the group comprising hydrogen, chlorine, bromine, iodine, fluorine, CN, $OR_B^5$, $COR_B^5$, $COOR_B^5$, $SR_B^5$, $C_3$-$C_7$-cycloalkyl, $OCOR_A^5$, $SO_2NR_A^6R_A^7$, $CONR_A^6R_A^7$, ($C_6$-$C_{10}$)-aryl, ($C_3$-$C_{10}$)-hetaryl, $NR_B^6R_B^7$, $C_3$-$C_7$-heterocycloalkyl, $C_3$-$C_7$-heterocycloalkenyl, $OCOR_B^5$, $SO_2NR_B^6R_B^7$, $CONR_B^6R_B^7$, $C_0$-$C_4$-alkylene-CN, $C_1$-$C_6$-haloalkyl, $C_1$-$C_6$-haloalkoxy, $NO_2$, $C_0$-$C_4$-alkylene-$OR_B^5$, O—$C_0$-$C_4$-alkylene-($C_6$-$C_{10}$)-aryl, O—$C_0$-$C_4$-alkylene-($C_2$-$C_{10}$)-hetaryl, $C_0$-$C_4$-alkylene-($C_6$-$C_{10}$)-aryl, $C_0$-$C_4$-alkylene-($C_2$-$C_{10}$)-hetaryl, $C_1$-$C_6$-alkyl, $C_2$-$C_6$-alkenyl, $C_2$-$C_6$-alkynyl, $C_2$-$C_6$-alkenyloxy, $C_2$-$C_6$-alkynyloxy, $C_1$-$C_4$-alkylthio, $C_0$-$C_4$-alkylene-$NR_B^6R_B^7$, $C_0$-$C_4$-alkylene-$COR_B^5$, $SO_2R_B^5$, $C_0$-$C_4$-alkylene-$COOR_B^5$, O—$C_1$-$C_4$-alkylene-$COOR_B^5$, $C_0$-$C_4$-alkylene-$SR_B^5$, $C_0$-$C_4$-alkylene-$C_3$-$C_7$-cycloalkyl, $C_0$-$C_4$-alkylene-$C_3$-$C_7$-heterocycloalkyl, $C_0$-$C_4$-alkylene-$C_3$-$C_7$-heterocycloalkenyl, $C_0$-$C_4$-alkylene-$OCOR_B^5$, $C_0$-$C_4$-alkylene-$SO_2NR_B^6R_B^7$, $C_0$-$C_4$-alkylene-$CONR_B^6R_B^7$, $C_1$-$C_4$-alkylene-$OCONR_B^6R_B^7$, $C_1$-$C_4$-alkylene-$SOR_B^5$, $C_1$-$C_4$-alkylene-$SO_2R_B^5$, NHCOO—$C_0$-$C_4$-alkylene-($C_6$-$C_{10}$)-aryl, NHCOO-($C_6$-$C_{10}$)-aryl, $NH_2$, NH($C_1$-$C_4$-alkyl), N($C_1$-$C_4$-alkyl)$_2$, morpholin-4-yl, pyrrolidin-1-yl, piperidin-1-yl, 4-piperazin-1-yl, 4-($C_1$-$C_4$-alkyl)-piperazin-1-yl;

where two of the residues $R_B^1$, $R_B^2$, $R_B^3$, or $R_B^4$ positioned adjacent ("ortho") to one another can also form a fused, unsaturated or aromatic 3- to 10-membered carbon ring, optionally substituted singly or multiply, identically or differently with the residues $C_1$-$C_6$-alkyl, $OCH_3$ or halogen, in which $R_B^5$ regardless of its respective occurrence, denotes hydrogen, a linear or branched, optionally substituted $C_1$-$C_6$-alkyl-, $C_2$-$C_6$-alkenyl-, $C_2$-$C_6$-alkynyl, $C_1$-$C_5$-alkylene-$C_1$-$C_4$-alkoxy-, mono- or bis-($C_1$-$C_6$)-alkylamino-($C_1$-$C_4$)-alkylene or ($C_1$-$C_6$)-acylamino-($C_1$-$C_4$)-alkylene residue or denotes an optionally substituted ($C_6$-$C_{10}$)-aryl, $C_3$-$C_7$-heterocycloalkyl, $C_3$-$C_7$-heterocycloalkenyl, ($C_3$-$C_{10}$)-hetaryl, $C_3$-$C_7$-cycloalkyl, $C_1$-$C_4$-alkylene-$C_3$-$C_7$-cycloalkyl, $C_1$-$C_4$-alkylene-($C_6$-$C_{10}$)-aryl, $C_1$-$C_4$-alkylene $C_3$-$C_7$-heterocycloalkyl, $C_1$-$C_4$-alkylene-$C_3$-$C_7$-heterocycloalkenyl or $C_1$-$C_4$-alkylene-($C_2$-$C_{10}$)-hetaryl, $R_B^6$ and $R_B^7$ independently of one another and regardless of their respective occurrence, denote hydrogen, a linear or branched, optionally substituted $C_1$-$C_6$-alkyl, $C_2$-$C_6$-alkenyl, $C_2$-$C_6$-alkynyl, $C_1$-$C_5$-alkylene-$C_1$-$C_4$-alkoxy, mono or bis-($C_1$-$C_6$)-alkylamino-($C_1$-$C_4$)-alkylene or ($C_1$-$C_6$)-acylamino-($C_1$-$C_4$)-alkylene residue or an, optionally substituted, ($C_6$-$C_{10}$)-aryl, $C_3$-$C_7$-heterocycloalkyl, $C_3$-$C_7$-heterocycloalkenyl, ($C_2$-$C_{10}$)-hetaryl, $C_3$-$C_7$-cycloalkyl, $C_1$-$C_4$-alkylene-$C_3$-$C_7$-cycloalkyl, $C_1$-$C_4$-alkylene-($C_6$-$C_{10}$)-aryl, $C_1$-$C_4$-alkylene-$C_3$-$C_7$-heterocycloalkyl, $C_1$-$C_4$-alkylene-$C_3$-$C_7$-heterocycloalkenyl or $C_1$-$C_4$-alkylene-($C_2$-$C_{10}$)-hetaryl residue, or an —$SO_2R_B^5$, —$CO_2R_B^5$, —CO—$NR_B^5R_B^5$, or $COR_B^5$ residue;

or $R_B^6$ and $R_B^7$ regardless of their respective occurrence together represent a 3 to 7 membered, optionally substituted, or preferably substituted with $C_1$-$C_6$-alkyl, OMe, halogen, saturated, unsaturated or aromatic heterocycle, which in addition to the ring nitrogen atom can contain up to three further different or identical heteroatoms selected from the group comprising O, N and S, and optionally two residues $R^x$ and $R^x$ substituted on this heterocycle together can represent a fused, saturated, unsaturated or aromatic carbon ring or heterocycle, which can contain up to three different or identical heteroatoms selected from the group comprising O, N and S and the ring can be optionally substituted or a further, optionally substituted ring can be condensed on this ring, $R^1$ and $R^2$ independently of one another, denote one of the residues hydrogen, Br, F, Cl, I, $C_1$-$C_4$-alkylene-CN, CN, $C_1$-$C_6$-haloalkyl, $C_1$-$C_6$-haloalkoxy, $NO_2$, $C_1$-$C_4$-alkylene-$OR_X^1$, $OR_X^1$, O—$C_1$-$C_4$-alkylene-($C_6$-$C_{10}$)-aryl, O—($C_6$-$C_{10}$)-aryl, O—$C_1$-$C_4$-alkylene-hetaryl, 0-hetaryl, $C_1$-$C_4$-alkylene-($C_6$-$C_{10}$)-aryl, ($C_6$-$C_{10}$)-aryl, $C_1$-$C_4$-alkylene-hetaryl, ($C_2$-$C_{10}$)-hetaryl, $C_1$-$C_6$-alkyl, $C_2$-$C_6$-alkenyl, $C_2$-$C_6$-alkynyl, $C_2$-$C_6$-alkenyloxy, $C_2$-$C_6$-alkynyloxy, $C_1$-$C_4$-alkylthio, $C_1$-$C_4$-alkylene-$NR_X^2R_X^3$, $NR_X^2R_X^3$, $C_1$-$C_4$-alkylene-$COR_X^1$, $COR_X^1$, $SO_2R_X^1$, $C_1$-$C_4$-alkylene-$COOR_X^1$, $COOR_X^1$, O—$C_1$-$C_4$-alkylene-$COOR_X^1$, $C_1$-$C_4$-alkylene-$SR_X^1$, $SR_X^1$, $C_1$-$C_4$-alkylene-$C_3$-$C_7$-cycloalkyl, $C_3$-$C_7$-cycloalkyl, $C_1$-$C_4$-alkylene-$C_3$-$C_7$-heterocycloalkyl, $C_3$-$C_7$-heterocycloalkyl, $C_1$-$C_4$-alkylene-$C_3$-$C_7$-heterocycloalkenyl, $C_3$-$C_7$-heterocycloalkenyl, $C_1$-$C_4$-alkylene-$OCOR_X^1$, $OCOR_X^1$, $C_1$-$C_4$-alkylene-$SO_2NR_X^2R_X^3$, $SO_2NR_X^2R_X^3$, $C_1$-$C_4$-alkylene-$CONR_X^2R_X^3$, $CONR_X^2R_X^3$, $C_1$-$C_4$-alkylene-$OCONR_X^2R_X^3$, $C_1$-$C_4$-alkylene-$SOR_X^1$, $C_1$-$C_4$-alkylene-$SO_2R_X^1$, NHCOO—$C_0$-$C_4$-alkylene-($C_6$-$C_{10}$)-aryl or NHCOO—($C_6$-$C_{10}$)-aryl in which $R_X^1$ regardless of its respective occurrence, denotes hydrogen, a linear or branched, optionally substituted $C_1$-$C_6$-alkyl, $C_2$-$C_6$-alkenyl, $C_2$-$C_6$-alkynyl, $C_1$-$C_5$-alkylene-$C_1$-$C_4$-alkoxy, mono or bis-($C_1$-$C_6$)-alkylamino-($C_1$-$C_4$)-alkylene or ($C_1$-$C_6$)-acylamino-($C_1$-$C_4$)-alkylene residue or an optionally substituted ($C_6$-$C_{10}$)-aryl, $C_3$-$C_7$-heterocycloalkyl, $C_3$-$C_7$-heterocycloalkenyl, ($C_2$-$C_{10}$)-hetaryl, $C_3$-$C_7$-cycloalkyl, $C_1$-$C_4$-alkylene-$C_3$-$C_7$-cycloalkyl, $C_1$-$C_4$-alkylene-($C_6$-$C_{10}$)-aryl, $C_1$-$C_4$-alkylene-$C_3$-$C_7$-heterocycloalkyl, $C_1$-$C_4$-alkylene $C_3$-$C_7$-heterocycloalkenyl or $C_1$-$C_4$-alkylene-($C_2$-$C_{10}$)-hetaryl residue, $R_X^2$ and $R_X^3$ independently of one another and regardless of their respective occurrence, denote hydrogen, a linear or branched, optionally substituted $C_1$-$C_6$-alkyl, $C_2$-$C_6$-alkenyl, $C_2$-$C_6$-alkynyl, $C_1$-$C_5$-alkylene-$C_1$-$C_4$-alkoxy, mono or bis-($C_1$-$C_6$)-alkylamino-($C_1$-$C_4$)-alkylene or ($C_1$-$C_6$)-acylamino-($C_1$-$C_4$)-alkylene residue or an optionally substituted ($C_6$-$C_{10}$)-aryl, $C_3$-$C_7$-heterocycloalkyl, $C_3$-$C_7$-heterocycloalkenyl, ($C_2$-$C_{10}$)-hetaryl, $C_3$-$C_7$-cycloalkyl, $C_1$-$C_4$-alkylene-$C_3$-$C_7$-cycloalkyl, $C_1$-$C_4$-alkylene-($C_6$-$C_{10}$)-aryl, $C_1$-$C_4$-alkylene-$C_3$-$C_7$-heterocycloalkyl, $C_1$-$C_4$-alkylene-$C_3$-$C_7$-heterocycloalkenyl or $C_1$-$C_4$-alkylene-($C_2$-$C_{10}$)-hetaryl residue, or an —$SO_2R_X^1$, —$CO_2R_X^1$, —CO—$NR_X^1R_X^1$, or $COR_X^1$ residue, or $R_X^2$ and $R_X^3$ together can form a 3-, 4-, 5-, 6- or 7-membered, optionally substituted, optionally preferably substituted with $C_1$-$C_6$-alkyl, $OCH_3$, and/or halogen, saturated, unsaturated or aromatic ($C_2$-$C_{10}$) heterocycle, which in addition to the ring nitrogen atom can contain one, two or three further different or identical heteroatoms selected from the group comprising O, N, and S, and optionally two residues $R_X^4$ and $R_X^5$ substituted on this heterocycle together can form a single or fused double or triple ring with a total of 3 to 21 ring atoms, each being saturated, unsaturated or aromatic and can optionally be substituted with up to six residues selected from the group comprising $C_1$-$C_6$-alkyl, $OCH_3$ and halogen, where at least one ring can contain a ring nitrogen atom and additionally, independently of one another, up to three further different or identical heteroatoms selected from the group comprising O, N, and S can be contained in each ring, or $R^1$ and $R^2$ independently of one another, denote hydrogen or an unsubstituted or singly, doubly or triply, identically or differently substituted 5- or 6-membered, aromatic heterocycle, having 1, 2, 3 or 4 heteroatoms, which are selected from the group comprising N, O and S, where the aromatic heterocycle can have one, two or three substituents $R_X^1$, which are selected, independently of one another and regardless of their respective occurrence, from the group comprising the residues hydrogen, Br, F, Cl, I, $C_1$-$C_4$-alkylene-CN, CN, $C_1$-$C_6$-haloalkyl, $C_1$-$C_6$-haloalkoxy, $NO_2$, $C_1$-$C_4$-alkylene-$OR_X^1$, $OR_X^1$, O—$C_1$-$C_4$-alkylene-($C_6$-$C_{10}$)-aryl, O—($C_6$-$C_{10}$)-aryl, O—$C_1$-$C_4$-alkylene-hetaryl, O-hetaryl, $C_1$-$C_4$-alkylene-($C_6$-$C_{10}$)-aryl, ($C_6$-$C_{10}$)-aryl, $C_1$-$C_4$-alkylene-hetaryl, ($C_2$-$C_{10}$)-hetaryl, $C_1$-$C_6$-alkyl, $C_2$-$C_6$-alkenyl, $C_2$-$C_6$-alkynyl, $C_2$-$C_6$-alkenyloxy, $C_2$-$C_6$-alkynyloxy, $C_1$-$C_4$-alkylthio, $C_1$-$C_4$-alkylene-$NR_X^2R_X^3$, $NR_X^2R_X^3$, $C_1$-$C_4$-alkylene-$COR_X^1$, $COR_X^1$, $SO_2R_X^1$, $C_1$-$C_4$-alkylene-$COOR_X^1$, $COOR_X^1$, O—$C_1$-$C_4$-alkylene-$COOR_X^1$, $C_1$-$C_4$-alkylene-$SR_X^1$, $SR_X^1$, $C_1$-$C_4$-alkylene-$C_3$-$C_7$-cycloalkyl, $C_3$-$C_7$-cycloalkyl, $C_1$-$C_4$-alkylene-$C_3$-$C_7$-heterocycloalkyl, $C_3$-$C_7$-heterocycloalkyl, $C_1$-$C_4$-alkylene-$C_3$-$C_7$-heterocycloalkenyl, $C_3$-$C_7$-heterocycloalkenyl, $C_1$-$C_4$-alkylene-$OCOR_X^1$, $OCOR_X^1$, $C_1$-$C_4$-alkylene-$SO_2NR_X^2R_X^3$, $SO_2NR_X^2R_X^3$, $C_1$-$C_4$-alkylene-$CONR_X^2R_X^3$, $CONR_X^2R_X^3$, $C_1$-$C_4$-alkylene-$OCONR_X^2R_X^3$, $C_1$-$C_4$-alkylene-$SOR_X^1$, $C_1$-$C_4$-alkylene-$SO_2R_X^1$, NHCOO—$C_0$-$C_4$-alkylene-($C_6$-$C_{10}$)-aryl or NHCOO—($C_6$-$C_{10}$)-aryl, in which the residues $R_X^1$, $R_X^2$ and $R_X^3$ have the meaning stated above;

Y is a residue —($R^y$)-(Z)-, in which $R^y$ denotes the general formula

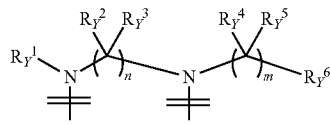

in which $R_Y^1$, $R_Y^2$, $R_Y^3$, $R_Y^4$, $R_Y^5$ and $R_Y^6$ independently of one another, are selected from the group comprising H, $C_1$-$C_6$-alkyl and $C_3$-$C_7$-cycloalkyl, n stands for the integer 1, 2 or 3, m stands for the integer 0, 1, 2 or 3, in which the residue $R_Y^1$ with one of the residues $R_Y^2$ and $R_Y^3$, in each case together with the N or C atom to which they are bound, yields a saturated or unsaturated 4-, 5-, 6- or 7-membered monocyclic ring;

or in which the residue $R_Y^1$ with one of the residues $R_Y^4$, $R_Y^5$ or $R_Y^6$, in each case together with the N or C atom to which they are bound, yields a saturated or unsaturated 4-, 5-, 6- or 7-membered monocyclic ring;

and/or in which one or two of the residues $R_Y^1$ and $R_Y^2$ with one or two of the residues $R_Y^4$, $R_Y^5$ or $R_Y^6$, in each case together with the N or C atom to which they are bound, yield a saturated or unsaturated mono-, bi- or tricyclic ring structure, which has 4-, 5-, 6- and/or 7-membered ring elements;

or in which the residue $R_Y^1$ plus one of the residues $R_Y^2$ and $R_Y^3$, in each case together with the N or C atom to which they are bound, yield a saturated or unsaturated 4-, 5-, 6- or 7-membered monocyclic ring and in addition one or two of the residues $R_Y^1$ and $R_Y^2$ are joined to one or two of the residues $R_Y^4$, $R_Y^5$ or $R_Y^6$, in each case together with the N or C atom to which they are bound, in such a way that overall a saturated or unsaturated bi- or tricyclic ring structure is formed, which has 4-, 5-, 6- and/or 7-membered ring members;

or in which the residue $R_Y^1$ plus one of the residues $R_Y^4$, $R_Y^5$ or $R_Y^6$, in each case together with the N or C atom to which they are bound, yields a saturated or unsaturated four-, five-, six- or seven-membered monocyclic ring and in addition one or two of the residues $R_Y^1$ and $R_Y^2$ with one or two of the residues $R_Y^4$, $R_Y^5$ or $R_Y^6$, in each case together with the N or C atom to which they are bound, are joined together so that overall a saturated or unsaturated bi- or tricyclic ring structure is formed, which has 4-, 5-, 6- and/or 7-membered ring members;

where the 4-, 5-, 6- or 7-membered, saturated or unsaturated mono-, bi- or tricyclic ring or the ring structure with 4-, 5-, 6- and/or 7-membered ring members thus formed, in addition can have a further heteroatom, selected from the group comprising O, S and $NR_{YY}^5$, as ring member, where $R_{YY}^5$ regardless of its respective occurrence for hydrogen, can stand for $C_1$-$C_4$-alkyl or $C_3$-$C_7$-cycloalkyl, and where the 4-, 5-, 6- or 7-membered, saturated or unsaturated mono-, bi- or tricyclic ring or the ring structure with 4-, 5-, 6- and/or 7-membered ring members thus formed, can have one or two substituents $R_{YY}^6$ and $R_{YY}^7$, which, independently of one another and regardless of their respective occurrence, are selected from the group comprising the residues $C_1$-$C_6$-alkyl, $C_1$-$C_6$-alkoxy, $C_3$-$C_6$-cycloalkyl, $C_3$-$C_6$-cycloalkoxy, oxo (—C=O), CN, $OR_{YY}^8$, $NR_{YY}^9R_{YY}^{10}$, $C_1$-$C_6$-alkylene-$NR_{YY}^9R_{YY}^{10}$, $SO_2NR_{YY}^9R_{YY}^{10}$, $CONR_{YY}^9R_{YY}^{10}$ and halogen;

Z is a 5- or 6-membered, saturated or fully or partially unsaturated heterocycle or aromatic heteroaryl ring, which has 1, 2, 3 or 4 heteroatoms, which are selected from the group comprising N, O and S, where the heterocycle or heteroaryl ring can have one, two or three identical or different substituents $R_Z^1$, which, independently of one another and regardless of their respective occurrence, are selected from the group comprising the residues $C_1$-$C_6$-alkyl, $C_1$-$C_6$-haloalkyl, $C_1$-$C_6$-alkyloxy, $CF_3$, $CHF_2$, $CH_2F$, $C_1$-$C_6$-haloalkyloxy, $OCH_3$, $OCF_3$, $OCHF_2$, CN, $OR_Z^2$, $NR_Z^3R_Z^4$, $NSO_2$—$C_1$-$C_6$-alkyl, $NSO_2$—$C_3$-$C_6$-cycloalkyl, $NO_2$, $SR_Z^5$, $SO_2R_Z^5$, $SO_2NR_Z^3R_Z^4$, $CONR_Z^3R_Z^4$, $COOR_Z^5$, $COR_Z^6$, $C_1$-$C_4$-haloalkyloxy, $C_2$-$C_6$-alkenyl, $C_2$-$C_6$-alkynyl, $C_2$-$C_6$-alkenyloxy, $C_2$-$C_6$-alkynyloxy, $C_3$-$C_7$-cycloalkyl, $C_3$-$C_7$-cycloalkyloxy, $C_3$-$C_7$-halocycloalkyloxy and halogen;

in which
$R_Z^1$, $R_Z^2$, $R_Z^3$, $R_Z^4$, $R_Z^5$ and $R_Z^6$ independently of one another and regardless of their respective occurrence, are selected from the group comprising H, optionally substituted $C_1$-$C_6$-alkyl, optionally substituted $C_3$-$C_7$-cycloalkyl and optionally substituted phenyl,
where $R_Z^2$ regardless of its respective occurrence can also be a —$(CH_2)_p$—$COR_Z^7$ or —CO—$(CH_2)_p$—$CONR_Z^8 R_Z^9$ residue,
in which
$R_Z^7$ regardless of its respective occurrence denotes H, OH, $C_1$-$C_6$-alkyl, $C_1$-$C_6$-alkoxy, $C_3$-$C_7$-cycloalkyl, $CH_2CH_2COOH$, $NR_Z^{10}R_Z^{11}$, preferably H, $CH_3$, $C_2H_5$, isopropyl, cyclohexyl, —$CH_2CH_2COOH$, $NH_2$, $N(CH_3)_2$;
$R_Z^8$ and $R_Z^9$ independently of one another, and their respective occurrence, are selected from the group comprising H, $C_1$-$C_6$-alkyl and $C_3$-$C_6$-cycloalkyl;
or $R_Z^8$ and $R_Z^9$ regardless of their respective occurrence, together with the nitrogen can form a ring selected from the group comprising azetidin-1-yl, pyrrolidin-1-yl, piperidin-1-yl, piperazin-1-yl, morpholin-4-yl and thiomorpholin-4-yl;
$R_Z^{10}$ regardless of its respective occurrence denotes H, $C_1$-$C_6$-alkyl, or $C_3$-$C_6$-cycloalkyl;
$R_Z^{11}$ regardless of its respective occurrence, denotes H, $C_1$-$C_6$-alkyl, $C_3$-$C_6$-cycloalkyl, —$C(CH_3)_2CH_2OH$, —$C(CH_3)(CH_2OH)_2$, or —$C(CH_2OH)_3$;
or $R_Z^{10}$ and $R_Z^{11}$ regardless of their respective occurrence, together with the nitrogen can form a ring selected from the group comprising azetidin-1-yl, pyrrolidin-1-yl, piperidin-1-yl, piperazin-1-yl, morpholin-4-yl and thiomorpholin-4-yl;
$R_Z^3$ regardless of its respective occurrence, can also denote a group $COR_Z^{12}$, in which $R_Z^{12}$ regardless of its respective occurrence, stands for hydrogen, optionally substituted $C_1$-$C_4$-alkyl or optionally substituted phenyl,
or where $R_Z^3$ with $R_Z^4$ regardless of their respective occurrence, also can jointly form a 5- or 6-membered, saturated or unsaturated carbon ring, which can have a heteroatom, selected from the group comprising O, S, and $NR_Z^{13}$, as ring member, where $R_Z^{13}$ stands for hydrogen or $C_1$-$C_4$-alkyl,
p regardless of its respective occurrence, denotes the integer 1 or 2;
their tautomeric, enantiomeric and diastereomeric forms, and prodrugs 30 thereof, and the physiologically compatible salts of said compounds, is provided.

Each of the aforementioned definitions of a variable can be combined with any of the aforementioned definitions of the other variables. This applies in particular to combination of preferred definitions of a variable with any or preferred definitions of the other variables.

According to a preferred embodiment of the invention, at least one compound of general formula (I) as stated above or according to claim 1, in which $R^1$, $R^2$, A and Y, unless described otherwise below, have the meanings given above and
B is a phenyl ring, which can be substituted with one or two identical or different residues, which are selected, independently of one another, from the group comprising chlorine, bromine, iodine, fluorine, CN, $CF_3$, $OCF_3$, $C_1$-$C_6$-alkoxy, $C_1$-$C_6$-haloalkoxy, $C_1$-$C_6$-haloalkyl, $NH_2$, NH—($C_1$-$C_6$-alkyl), N($C_1$-$C_6$-alkyl)($C_1$-$C_6$-alkyl), $C_1$-$C_6$-alkyl, $C_2$-$C_6$-alkenyl, $C_2$-$C_6$-alkynyl, $C_2$-$C_6$-alkenyloxy, $C_2$-$C_6$-alkynyloxy, $C_3$-$C_6$-cycloalkyl, $C_3$-$C_6$-cycloalkoxy, halogenated $C_3$-$C_6$-cycloalkyl and halogenated $C_3$-$C_6$-cycloalkoxy,
their tautomeric, enantiomeric and diastereomeric forms, and prodrugs thereof, and the physiologically compatible salts of said compounds, is provided. If there is a substituent on B, it is preferably disposed in position 2 or position 4 on the phenyl ring. If there are two substituents on B, they are preferably disposed in position 2 and position 4 or in position 2 and position 5 on the phenyl ring.

According to a preferred embodiment of the invention, at least one compound of general formula (I) as stated above or according to Claim 1 or 2, in which $R^1$, $R^2$, A and Y, unless described otherwise below, have the meanings given above and
B is a phenyl ring, which can be substituted with one or two identical or different residues, which are selected, independently of one another, from the group comprising hydrogen, chlorine, fluorine, CN, $CH_3$, $OCH_3$, $NH_2$, $NHCH_3$, $N(CH_3)_2$,
their tautomeric, enantiomeric and diastereomeric forms, and prodrugs thereof, and the physiologically compatible salts of said compounds, is provided. If there is a substituent on B, it is preferably disposed in position 2 or position 4 on the phenyl ring. If there are two substituents on B, they are preferably disposed in position 2 and position 4 or in position 2 and position 5 on the phenyl ring.

According to a preferred embodiment of the invention, at least one compound of general formula (I) as stated above, in which $R^1$, $R^2$, A and Y, unless described otherwise below, have the meanings given above and
B is a residue selected from the group comprising phenyl, 2-methoxyphenyl, 4-methoxyphenyl, 2,4-dimethoxyphenyl, 3,4-dimethoxyphenyl, 2-methoxy-4-methylphenyl, 2-fluorophenyl, 4-fluorophenyl, 4-chlorophenyl, 2-methoxy-5-fluorophenyl, 2-methoxy-5-methylphenyl, 2-methoxy-4-methoxyphenyl, 2-isobutoxy-5-methoxyphenyl, 2-ethoxy-5-ethylphenyl, 2-ethoxy-4-methoxyphenyl, and 4-cyanophenyl,
their tautomeric, enantiomeric and diastereomeric forms, and prodrugs thereof, and the physiologically compatible salts of said compounds, is provided.

According to a preferred embodiment of the invention, at least one compound of general formula (I) as stated above, in which $R^1$, $R^2$, A and Y, unless described otherwise below, have the meanings given above and
B is 2,4-dimethoxyphenyl,
their tautomeric, enantiomeric and diastereomeric forms, and prodrugs thereof, and the physiologically compatible salts of said compounds, is provided.

According to a preferred embodiment of the invention, at least one compound of general formula (I) as stated above, in which B, A and Y, unless described otherwise below, have the meanings given above and
$R^1$ and $R^2$ independently of one another, are selected from the group comprising hydrogen, halogen, F, Cl, Br, I, CN, $C_1$-$C_6$-alkyl, —O—$C_1$-$C_6$-alkyl, $C_3$-$C_6$-cycloalkyl, —O—$C_3$-$C_6$-cycloalkyl, halogenated O—$C_1$-$C_6$-alkyl, halogenated $C_1$-$C_6$-alkyl, halogenated $C_3$-$C_6$-cycloalkyl, halogenated —O—$C_3$-$C_6$-cycloalkyl and an unsubstituted or singly, doubly or triply, identically or differently substituted 5- or 6-membered, aromatic heterocycle, which has 1, 2, 3 or 4 heteroatoms, which are selected from the group comprising N, O and S, in particular from the group comprising hydrogen, halogen, F, Cl, Br, I, CN, $C_1$-$C_6$-alkyl, O—$C_1$-$C_6$-alkyl, halogenated O—$C_1$-$C_6$-alkyl and halogenated $C_1$-$C_6$-alkyl,
their tautomeric, enantiomeric and diastereomeric forms, and prodrugs thereof, and the physiologically compatible salts of said compounds, is provided.

According to a preferred embodiment of the invention, at least one compound of general formula (I) as stated above, in which B, A and Y, unless described otherwise below, have the meanings given above and $R^1$ and $R^2$ independently of one another, are selected from the group comprising hydrogen, Cl, CN, $OCH_3$, $CH_3$, and an unsubstituted or singly, doubly or triply, identically or differently substituted 5- or 6-membered, aromatic heterocycle, which has 1, 2, 3 or 4 heteroatoms, which are selected from the group comprising N, O and S, in particular from the group comprising Cl, CN, $OCH_3$ and $CH_3$, their tautomeric, enantiomeric and diastereomeric forms, and prodrugs thereof, and the physiologically compatible salts of said compounds, is provided.

$R^1$ is preferably a residue different from hydrogen, in particular a residue from the group consisting of F, Cl, Br, I, CN, $C_1$-$C_6$-alkyl, —O—$C_1$-$C_6$-alkyl, halogenated O—$C_1$-$C_6$-alkyl and halogenated $C_1$-$C_6$-alkyl, particularly preferably a residue from the group consisting of Cl, CN, $OCH_3$ and $CH_3$ and specifically CN.

$R^2$ is in particular hydrogen.

According to a preferred embodiment of the invention, at least one compound of general formula (I) as stated above, in which B, A and Y, unless described otherwise below, have the meanings given above and $R^1$ is CN and
$R^2$ is hydrogen,
their tautomeric, enantiomeric and diastereomeric forms, and prodrugs thereof, and the physiologically compatible salts of said compounds, is provided.

According to a preferred embodiment of the invention, at least one compound of general formula (I) as stated above, its tautomeric, enantiomeric and diastereomeric forms, and prodrugs thereof, and the physiologically compatible salts of said compounds, is provided, in which $R^1$, $R^2$, A and Y, unless described otherwise below, have the meanings given above and the residue R1 is in position 5 and is different from hydrogen, and is in particular CN. In this embodiment, $R^2$ is in particular hydrogen.

According to a preferred embodiment of the invention, at least one compound of general formula (I) as stated above, in which $R^1$, $R^2$, B and Y, unless described otherwise below, have the meanings given above and A is a phenyl ring, which is unsubstituted or substituted with one or two identical or different residues, which, independently of one another, are selected from the group comprising halogen, CN, $NO_2$, $C_1$-$C_4$-alkoxy, $C_1$-$C_6$-alkoxy-$C_1$-$C_6$-alkyl, $C_1$-$C_6$-alkyl, $NH_2$, NH—($C_1$-$C_6$-alkyl), N($C_1$-$C_6$-alkyl)($C_1$-$C_6$-alkyl), ($C_0$-$C_6$-alkyl)-NH—$C_1$-$C_6$-alkylene, ($C_0$-$C_6$-alkyl)($C_1$-$C_6$-alkyl)-N—$C_1$-$C_6$-alkylene, $C_3$-$C_6$-cycloalkyl, $C_3$-$C_6$-cycloalkoxy, $C_1$-$C_6$-haloalkyl, $C_1$-$C_6$-alkylcarbonyl, $C_1$-$C_6$-haloalkylcarbonyl, $C_1$-$C_6$-alkylsulphonyl, $C_1$-$C_6$-haloalkylsulphonyl, $C_1$-$C_6$-haloalkoxy, $C_3$-$C_6$-halocycloalkyl and $C_3$-$C_6$-halocycloalkoxy, in particular from the group comprising halogen, O—$C_1$-$C_4$-alkyl, $C_1$-$C_6$-alkyl-O—$C_1$-$C_6$-alkyl, ($C_0$-$C_6$-alkyl)-NH—$C_1$-$C_6$-alkylene, ($C_0$-$C_6$-alkyl)($C_1$-$C_6$-alkyl)-N-$C_1$-$C_6$-alkylene, $C_3$-$C_6$-cycloalkyl, —O—$C_3$-$C_6$-cycloalkyl, $C_1$-$C_6$-haloalkyl, $C_1$-$C_6$-haloalkoxy, $C_3$-$C_6$-halocycloalkyl and $C_3$-$C_6$-halocycloalkoxy, their tautomeric, enantiomeric and diastereomeric forms, and prodrugs thereof, and the physiologically compatible salts of said compounds, is provided. If there is a substituent on A, it is disposed in position 2, 3 or 4 on the phenyl ring. If there are two substituents on A, they are preferably disposed in position 2 and position 4 or in position 2 and position 5 on the phenyl ring.

According to a preferred embodiment of the invention, at least one compound of general formula (I) as stated above, in which $R^1$, $R^2$, B and Y, unless described otherwise below, have the meanings given above and A is a phenyl ring, which is substituted with one or two identical or different residues, which, independently of one another, are selected from the group comprising fluorine, chlorine, CN, $NH_2$, $CF_3$, $CH_3$, $C_2H_5$, n-$C_3H_7$, i-$C_3H_7$, sec-$C_4H_9$, iso-$C_4H_9$, tert-$C_4H_9$, $C(O)CH_3$, $SO_2CH_3$, $SO_2CF_3$, $OCF_3$, $OCHF_2$, methoxy, ethoxy, methoxymethyl, N,N-dimethylaminomethyl and N-methylaminomethyl, in particular from the group comprising fluorine, chlorine, methoxy, ethoxy, methoxymethyl, N,N-dimethylamino-methyl and N-methylaminomethyl, their tautomeric, enantiomeric and diastereomeric forms, and prodrugs thereof, and the physiologically compatible salts of said compounds, is provided. If there is a substituent on A, it is disposed in position 2, 3 or 4 on the phenyl ring. If there are two substituents on A, they are preferably disposed in position 2 and position 4 or in position 2 and position 5 on the phenyl ring.

According to a preferred embodiment of the invention, at least one compound of general formula (I) as stated above, in which $R^1$, $R^2$, B and Y, unless described otherwise below, have the meanings given above and A is a phenyl ring, which is substituted with one or two identical or different residues, which, independently of one another, are selected from the group comprising fluorine, chlorine, CN, $NH_2$, $CF_3$, $CH_3$, $C_2H_5$, n-$C_3H_7$, i-$C_3H_7$, sec-$C_4H_9$, iso-$C_4H_9$, tert-$C_4H_9$, $C(O)CH_3$, $SO_2CH_3$, $SO_2CF_3$, $OCF_3$, $OCHF_2$, methoxy, ethoxy, methoxymethyl, N,N-dimethylaminomethyl and N-methylaminomethyl, in particular from the group comprising fluorine, chlorine, methoxy, ethoxy, methoxymethyl, N,N-dimethylaminomethyl, N-methylaminomethyl, where if there is a substituent it is disposed in position 2, 3 or 4, and if there are two substituents, one substituent is disposed in position 2 and the other is disposed in position 4 or 5, their tautomeric, enantiomeric and diastereomeric forms, and prodrugs thereof, and the physiologically compatible salts of said compounds, is provided.

According to a preferred embodiment of the invention, at least one compound of general formula (I) as stated above, in which $R^1$, $R^2$, B and Y, unless described otherwise below, have the meanings given above and A is a phenyl ring, which is substituted with one or two residues, which, independently of one another, are selected from the group comprising 2-fluoro, 4-fluoro, 2-chloro, 4-chloro, 2-methoxy, 2-methyl, 2-ethyl, 3-methoxy, 4-methoxy, 2-ethoxy, 4-ethoxy, 4-trifluoromethyl, 4-difluoromethoxy, 4-trifluoromethoxy, 4-methyl, 4-ethyl, 4-isopropyl, 4-tert-butyl, 4-acetyl, 4-nitro, 4-cyano, 4-methylsulphonyl, 2-methoxymethyl, 4-amino, 3-N,N-dimethylaminomethyl and 3-N-methylaminomethyl, in particular from the group comprising, 4-fluoro, 2-chloro, 2-methoxy, 3-methoxy, 4-methoxy, 2-ethoxy, 2-methoxymethyl, 3-N,N-dimethylamino-methyl and 3-N-methylamino-methyl, their tautomeric, enantiomeric and diastereomeric forms, and prodrugs thereof, and the physiologically compatible salts of said compounds, is provided.

According to a preferred embodiment of the invention, at least one compound of general formula (I) as stated above, in which $R^1$, $R^2$, B and Y, unless described otherwise below, have the meanings given above and A is a residue selected from the group comprising 2-methoxyphenyl, 2-ethoxyphenyl, 2-ethoxy-4-fluorophenyl, 2-ethoxy-5-methoxyphenyl, 2-chlorophenyl, 3,4-dimethoxyphenyl, 2,4-dimethoxyphenyl, 2,3-dimethoxyphenyl, 2,5-dimethoxyphenyl, 2-methoxymethylphenyl, 3-N,N-dimethylaminomethylphenyl, 2-methoxy-3-N,N-dimethylamino-methylphenyl and 2-methoxy-3-N-methylaminomethylphenyl, 2,4-difluorophenyl, 2,4-dichlorophenyl, 2-chloro-4-fluorophenyl, 2-fluoro-4-cyanophenyl, 2-chloro-4-trifluoromethylphenyl, 2-methoxy-4-ethoxyphenyl, 4-chloro-2-fluorophenyl, 4-fluoro-2-methylphenyl, 4-tert-butylphenyl, 4-isopropylphenyl, 4-(trifluoromethoxy)phenyl, 4-trifluoromethylphenyl, 4-aminophenyl, 4-methylphenyl, 4-(methylsulphonyl)phenyl, 4-difluoromethoxyphenyl, 4-acetylphenyl, 4-ethoxyphenyl, 2-methoxy-4-nitrophenyl, 2-ethoxy-4-methoxyphenyl, in particular from the group comprising 2-methoxyphenyl, 2-ethoxyphenyl, 2-ethoxy-4-fluorophenyl, 2-ethoxy-5-methoxyphenyl, 2-chlorophenyl, 3,4-dimethoxyphenyl, 2,4-dimethoxyphenyl, 2,3-dimethoxyphenyl, 2,5-dimethoxyphenyl, 2-methoxymethylphenyl, 3-N,N-dimethylamino-methylphenyl, 2-methoxy-3-N,N-dimethylaminomethylphenyl and 2-methoxy-3-N-methylaminomethylphenyl,
their tautomeric, enantiomeric and diastereomeric forms, and prodrugs thereof, and the physiologically compatible salts of said compounds, is provided.

According to a further preferred embodiment of the invention, at least one compound of the general formula (I) as stated above, its tautomeric, enantiomeric and diastereomeric forms, and the prodrugs thereof, and the physiologically compatible salts of said compounds, in which $R^1$, $R^2$, B and Y, unless described otherwise below, have the meanings given above, and A is a naphthyl residue, in particular a 1-naphthyl residue, which is optionally substituted with one or two identical or different residues which are selected independently of one another from the group comprising halogen, CN, $NO_2$, $C_1$-$C_4$-alkoxy, $C_1$-$C_6$-alkoxy-$C_1$-$C_6$-alkyl, $C_1$-$C_6$-alkyl, $NH_2$, NH—($C_1$-$C_6$-alkyl), N($C_1$-$C_6$-alkyl)($C_1$-$C_6$-alkyl), ($C_0$-$C_6$-alkyl)-NH—$C_1$-$C_6$-alkylene, ($C_0$-$C_6$-alkyl)($C_1$-$C_6$-alkyl)-N—$C_1$-$C_6$-alkylene, $C_3$-$C_6$-cycloalkyl, $C_3$-$C_6$-cycloalkoxy, $C_1$-$C_6$-haloalkyl, $C_1$-$C_6$-alkylcarbonyl, $C_1$-$C_6$-haloalkylcarbonyl, $C_1$-$C_6$-alkylsulphonyl, $C_1$-$C_6$-haloalkylsulphonyl, $C_1$-$C_6$-haloalkoxy, $C_3$-$C_6$-halocycloalkyl and $C_3$-$C_6$-halocycloalkoxy, in particular from the group comprising fluorine, chlorine, CN, $NH_2$, $CF_3$, $CH_3$, $C_2H_5$, n-$C_3H_7$, i-$C_3H_7$, sec-$C_4H_9$, iso-$C_4H_9$, tert-$C_4H_9$, C(O)$CH_3$, $SO_2CH_3$, $SO_2CF_3$, $OCF_3$, $OCHF_2$, methoxy, ethoxy, methoxymethyl, N,N-dimethylaminomethyl, N-methylaminomethyl, in particular from the group comprising fluorine, chlorine, methoxy, ethoxy, methoxymethyl, N,N-dimethylaminomethyl and N-methylaminomethyl, is provided.

If there is a substituent on A, it is preferably disposed in position 5 on the naphthyl radical.

According to a further preferred embodiment of the invention, at least one compound of the general formula (I) as stated above, its tautomeric, enantiomeric and diastereomeric forms, and the prodrugs thereof, and the physiologically compatible salts of said compounds, in which $R^1$, $R^2$, B and Y, unless described otherwise below, have the meanings given above, and A is a 1-naphthyl residue which is substituted by a residue which is selected from the group consisting of fluorine and chlorine, where the residue is preferably disposed in position 5 of the naphthyl radical.

According to a preferred embodiment of the invention, at least one compound of general formula (I) as stated above, in which $R^1$, $R^2$, B and Y, unless described otherwise below, have the meanings given above and according to a preferred embodiment of the invention, at least one compound of the general formula (I) as stated above, its tautomeric, enantiomeric and diastereomeric forms, and the prodrugs thereof, and the physiologically compatible salts of said compounds, in which $R^1$, $R^2$, A and B, unless described otherwise below, have the meanings given above, and Y denotes a residue selected from the group comprising the residues Y1 to Y24 stated below

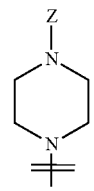

Y1

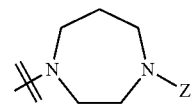

Y2

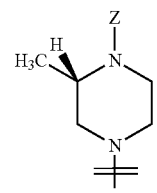

or enantiomer

Y3/4

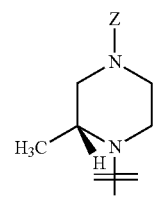

or enantiomer

Y5/6

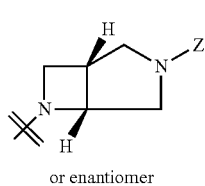

or enantiomer

Y7/8

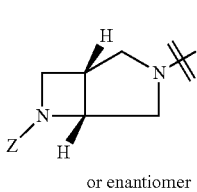

or enantiomer

Y9/10

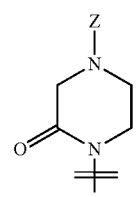

Y11

Y12

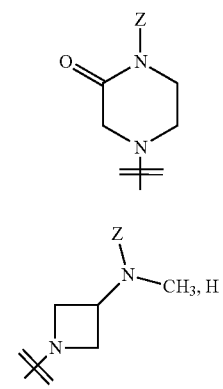

Y13

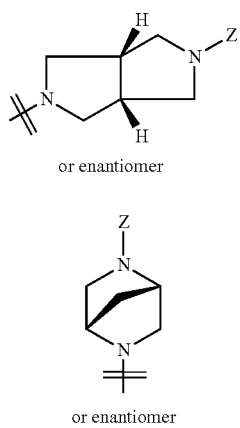

or enantiomer

Y14/15

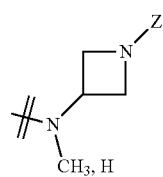

Y16/17

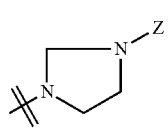

or enantiomer

Y18

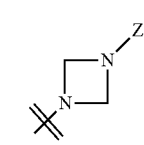

Y19

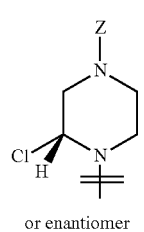

Y20

Y21/22

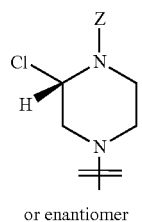

or enantiomer

Y23/24

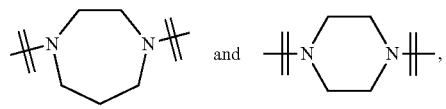

or enantiomer in which Z has the meanings stated above,
or Y stands for the residue $(R^Y)$-(Z), in which
$R^Y$ denotes a residue selected from the group of residues

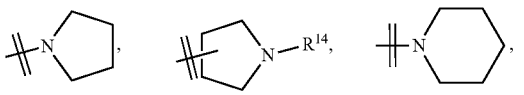

where $R^Y$ can be substituted with one or two substituents $R_{YY}^6$ and $R_{YY}^7$ and $R_{YY}^6$ and $R_{YY}^7$ independently of one another are as defined previously, and Z denotes a residue selected from the group of residues

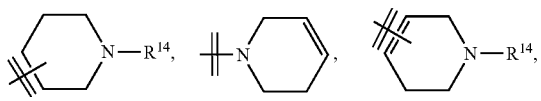

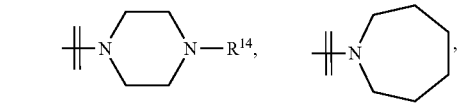

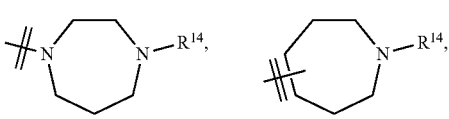

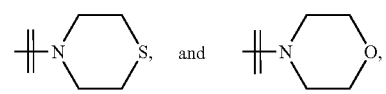

where Z can be substituted with one or two substituents $R_{YY}^6$ and $R_{YY}^8$ and $R_{YY}^6$ and $R_{YY}^7$ independently of one another, and regardless of their occurrence, are as defined previously, and $R^{14}$ has one of the abovementioned meanings.

According to a preferred embodiment of the invention, at least one compound of general formula (I) as stated above, its tautomeric, enantiomeric and diastereomeric forms, and prodrugs thereof, and the physiologically compatible salts of said compounds, is provided, in which $R^1$, $R^2$, A and B, unless described otherwise below, have the meanings given above and Y denotes a residue selected from the group comprising the residues Y1 to Y6 and Y14 to Y17 stated below

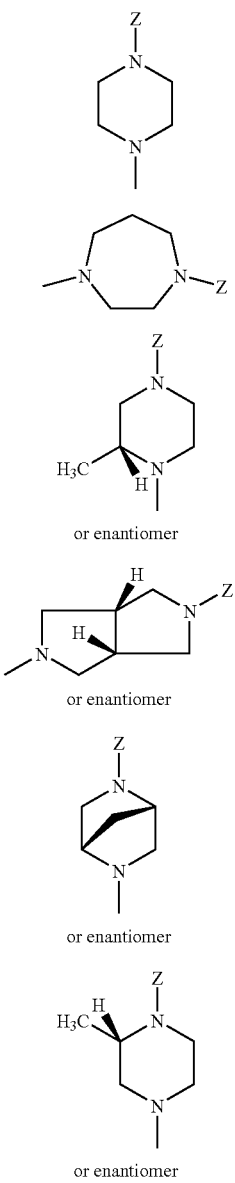

in which Z has the meanings stated above.

According to a particularly preferred embodiment of the invention, at least one compound of the general formula (I) as stated above, its tautomeric, enantiomeric and diastereomeric forms, and the prodrugs thereof, and the physiologically compatible salts of said compounds, in which $R^1$, $R^2$, A and B, unless described otherwise below, have the meanings given above, and Y is a Y1 residue, is provided.

According to a preferred embodiment of the invention, at least one compound of general formula (I) as stated above, its tautomeric, enantiomeric and diastereomeric forms, and prodrugs thereof, and the physiologically compatible salts of said compounds, is provided, in which $R^1$, $R^2$, A, B and $R^Y$, unless described otherwise below, have the meanings given above and Z is a 5- or 6-membered, saturated or fully or partially unsaturated heterocycle or aromatic heteroaryl ring, which has 1, 2, 3 or 4 heteroatoms, which are selected from the group comprising N, O and S, where the heterocycle or heteroaryl ring can have one, two or three identical or different substituents $R_Z^1$, which, independently of one another and regardless of their respective occurrence, are selected from the group comprising the residues hydrogen, halogen, chlorine, bromine, iodine, fluorine, CN, $CF_3$, $OCF_3$, $NO_2$, OH, O—$C_1$-$C_4$-alkyl, $C_1$-$C_6$-alkyl, O—$C_1$-$C_4$-haloalkyl, $C_1$-$C_6$-haloalkyl, $C_2$-$C_6$-alkenyl, $C_2$-$C_6$-alkynyl, $NH_2$, N-oxide, $NH(C_1$-$C_6$-alkyl) and $N(C_1$-$C_6$-alkyl)($C_1$-$C_6$-alkyl).

According to a preferred embodiment of the invention, at least one compound of general formula (I) as stated above, its tautomeric, enantiomeric and diastereomeric forms, and prodrugs thereof, and the physiologically compatible salts of said compounds, is provided, in which $R^1$, $R^2$, A, B and $R^Y$, unless described otherwise below, have the meanings given above and Z is a residue selected from the group comprising 4-pyridyl, 2-pyridyl, 3-pyridyl, 2-triazinyl, 4-pyrimidynyl, 1,3-thiazin-2-yl, which can be substituted with one, two or three identical or different substituents, which, independently of one another, are selected from the group comprising the residues hydrogen, halogen, chlorine, bromine, iodine, fluorine, CN, $CF_3$, $OCF_3$, $NO_2$, OH, or in each case optionally substituted O—$C_1$-$C_4$-alkyl, $C_1$-$C_6$-alkyl, O—$C_1$-$C_4$-haloalkyl, $C_3$-$C_7$-cycloalkyl, $C_1$-$C_6$-haloalkyl, $C_2$-$C_6$-alkenyl, $C_2$-$C_6$-alkynyl, $NH_2$, N-oxides, $NH(C_1$-$C_6$-alkyl) and $N(C_1$-$C_6$-alkyl)($C_1$-$C_6$-alkyl).

According to a preferred embodiment of the invention, at least one compound of general formula (I) as stated above, and its tautomeric, enantiomeric and diastereomeric forms, and prodrugs thereof, and the physiologically compatible salts of said compounds, is provided, in which $R^1$, $R^2$, A, B and $R^Y$, unless described otherwise below, have the meanings given above and Z is a residue selected from the group comprising the residues

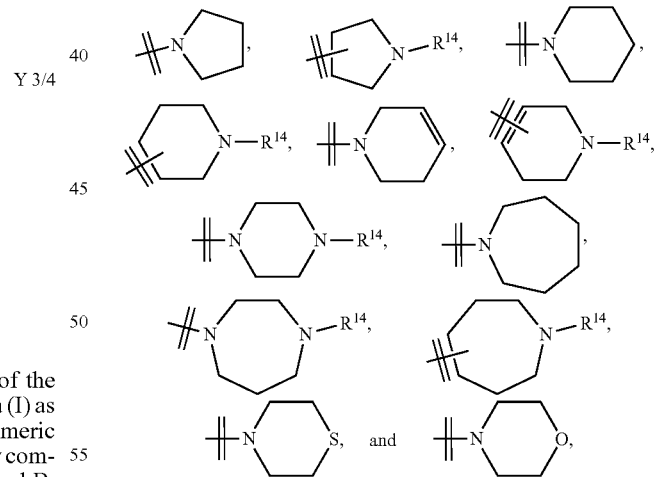

where Z can in addition be substituted with $R_Z^{12}$ and/or $R_Z^{13}$, where $R_Z^{12}$ is hydrogen, $C_1$-$C_6$-alkyl, $C_2$-$C_6$-alkenyl, $C_2$-$C_6$-alkynyl, OH, O—$C_1$-$C_4$-alkyl, O—$C_0$-$C_4$-alkylene-phenyl, $NH_2$, $NH(C_1$-$C_4$-alkyl) or $N(C_1$-$C_4$-alkyl)($C_1$-$C_4$-alkyl), $R_Z^{13}$ is hydrogen, $C_1$-$C_6$-alkyl, $C_2$-$C_6$-alkenyl, $C_2$-$C_6$-alkynyl, OH, $O(C_1$-$C_4$-alkyl), O—$C_0$-$C_4$-alkylene-phenyl, $NH_2$, $NH(C_1$-$C_4$-alkyl) or $N(C_1$-$C_4$-alkyl)($C_1$-$C_4$-alkyl), $R^{14}$ is hydrogen, $C_1$-$C_6$-alkyl, $C_2$-$C_6$-alkenyl, $C_2$-$C_6$-alkynyl or CO—$C_4$-alkylene-phenyl.

According to a preferred embodiment of the invention, at least one compound of general formula (I) as stated above, its tautomeric, enantiomeric and diastereomeric forms, and prodrugs thereof, and the physiologically compatible salts of said compounds, is provided, in which $R^1$, $R^2$, A, B and $R^Y$, unless described otherwise below, have the meanings given above and Z is a residue selected from the group comprising 4-pyridyl, 2-pyridyl, 3-pyridyl, 2-triazinyl, 4-pyrimidinyl, 1,3-thiazin-2-yl, which can be substituted with one, two or three identical or different substituents, which, independently of one another, are selected from the group comprising the residues hydrogen, chlorine, fluorine, CN, methyl, methoxy, ethyl, ethoxy, isopropyl and cyclopropyl. Z is in particular 4-pyridyl which may be substituted by one, two or three identical or different substituents which are selected independently of one another from the aforementioned substituents, and in particular from the group comprising the residues hydrogen, chlorine, fluorine, CN, methyl, methoxy, ethyl, ethoxy, isopropyl and cyclopropyl.

According to a preferred embodiment of the invention, at least one compound of general formula (I) as stated above, its tautomeric, enantiomeric and diastereomeric forms, and prodrugs thereof, and the physiologically compatible salts of said compounds, is provided, in which $R^1$, $R^2$, A, B and $R^Y$, unless described otherwise below, have the meanings given above and Z is a residue selected from the group comprising pyridin-4-yl, pyridin-3-yl, pyridin-2-yl, 2-methylpyridin-4-yl, 2-ethoxypyridin-4-yl, 2-fluoropyridin-4-yl, 2-chloropyridin-4-yl, 3-methyl pyridin-4-yl, 3-fluoropyridin-4-yl, N-oxopyridin-4-yl, 3,5-dichloropyridin-4-yl, 2-trifluoromethylpyridin-4-yl, 2-Isopropylpyridin-4-yl, 2-ethylpyridin-4-yl, 5-cyanopyridin-4-yl, 1,3-thiazol-2-yl, 1,3,5-triazin-2-yl and 1,3-pyrimidin-4-yl, in particular from the group comprising pyridin-4-yl, pyridin-3-yl, pyridin-2-yl, 2-methyl-pyridin-4-yl, 2-ethoxy-pyridin-4-yl, 2-fluoro-pyridin-4-yl, 2-chloro-pyridin-4-yl, 3-methyl-pyridin-4-yl, 3-fluoro-pyridin-4-yl, N-oxides-pyridin-4-yl, 5-cyano-pyridin-4-yl, 1,3-thiazol-2-yl, 1,3,5-triazin-2-yl and 1,3-pyrimidin-4-yl.

According to a preferred embodiment of the invention, at least one compound of general formula (I) as stated above, its tautomeric, enantiomeric and diastereomeric forms, and prodrugs thereof, and the physiologically compatible salts of said compounds, is provided, in which $R^1$, $R^2$, A, B and $R^Y$, unless described otherwise below, have the meanings given above and Z is a residue selected from the group comprising pyridin-4-yl, 2-methyl-pyridin-4-yl, 2-ethoxypyridin-4-yl, 2-fluoro-pyridin-4-yl, 2-chloropyridin-4-yl, 3-methylpyridin-4-yl, 3-fluoropyridin-4-yl, N-oxopyridin-4-yl, 3,5-dichloropyridin-4-yl, 2-trifluoromethylpyridin-4-yl, 2-isopropylpyridin-4-yl, 2-ethylpyridin-4-yl and 5-cyanopyridin-4-yl, in particular from the group comprising pyridin-4-yl and 2-methyl-pyridin-4-yl.

The compounds of the invention of the formula (I) have a chirality centre in position 3 of the oxindole structure (position bearing the Y and A residues). The compounds of the formula (I) are thus optically active substances. If the compounds of the general formula (I) have a further chirality centre, for example in the group $R^y$ or Z, diastereomers of these compounds exist. The compounds of the invention of the formula (I) can accordingly exist as a mixture of diastereomers, or as a mixture of diastereomers in which one of the two diastereomers is enriched, or as essentially diastereomerically pure compounds (diastereomeric excess de >90%). The compounds are preferably in the form of essentially diastereomerically pure compounds. The respective diastereomers may in turn be in the form of a mixture of enantiomers, for example as racemate, or of a mixture of enantiomers in which one of the two enantiomers is enriched, or of essentially enantiomerically pure compounds (enantiomeric excess ee >90%). The respective diastereomers are preferably in the form of essentially enantiomerically pure compounds. Compounds which are essentially diastereomerically pure and enantiomerically pure (de >90%, ee >90%) are particularly preferred.

General formula (I) therefore also encompasses diastereomeric and/or enantiomeric forms of the compounds of the general formula (I).

According to a further aspect of the invention, a medicinal product, containing at least one compound of general formula (I) as defined above or according to one of Claims 1 to 21 or a physiologically acceptable salt thereof, is provided.

According to a further aspect of the invention, the use of at least one compound of general formula (I) as defined above or according to one of Claims 1 to 21 or of a physiologically acceptable salt thereof as medicinal products, is provided.

According to a further aspect of the invention, the use of at least one compound of general formula (I) as defined above or of a physiologically acceptable salt thereof is provided for the treatment and/or prophylaxis of at least one vasopressin-dependent and/or oxytocin-dependent disease and/or for the production of a medicinal product for the treatment and/or prophylaxis of at least one of the stated diseases.

According to a further aspect of the invention, the use of at least one compound of general formula (I) as defined above or of a physiologically acceptable salt thereof is provided for the treatment and/or prophylaxis of at least one disease selected from the group comprising diabetes insipidus, enuresis nocturna, incontinence, diseases in which disturbances of blood clotting occur and/or for delaying micturition and/or for the production of a medicinal product for the treatment and/or prophylaxis of at least one of the stated diseases.

According to a further aspect of the invention, the use of at least one compound of general formula (I) as defined above or of a physiologically acceptable salt thereof is provided for the treatment and/or prophylaxis of at least one disease selected from the group comprising hypertension, pulmonary hypertension, heart failure, myocardial infarction, coronary spasm, unstable angina, PTCA (percutaneous transluminal coronary angioplasty), ischaemic heart diseases, disorders of the renal system, oedema, renal vasospasm, necrosis of the renal cortex, hyponatraemia, hypokalaemia, Schwartz-Bartter syndrome, disorders of the gastrointestinal tract, gastric vasospasm, hepatic cirrhosis, gastrointestinal ulcer, vomiting, vomiting associated with chemotherapy, and/or travel sickness and/or for the production of a medicinal product for the treatment and/or prophylaxis of at least one of the stated diseases.

According to a further aspect of the invention, the use of at least one compound of general formula (I) as defined above or of a physiologically acceptable salt thereof is provided for the treatment of affective disorders and/or for the production of a medicinal product for the treatment of affective disorders.

According to a further aspect of the invention, the use of at least one compound of general formula (I) as defined above or of a physiologically acceptable salt thereof is provided for the treatment of anxiety disorders and/or stress-related anxiety disorders and/or for the production of a medicinal product for the treatment of anxiety disorders and/or stress-related anxiety disorders.

According to a further aspect of the invention, the use of at least one compound of general formula (I) as defined above or of a physiologically acceptable salt thereof is provided for the treatment of memory disorders and/or Alzheimer's disease and/or for the production of a medicinal product for the treatment of memory disorders and/or Alzheimer's disease.

According to a further aspect of the invention, the use of at least one compound of general formula (I) as defined above or of a physiologically acceptable salt thereof is provided for the treatment of psychoses and/or psychotic disorders and/or for the production of a medicinal product for the treatment of psychoses and/or psychotic disorders.

According to a further aspect of the invention, the use of at least one compound of general formula (I) as defined above or of a physiologically acceptable salt thereof is provided for the treatment of Cushing syndrome and/or for the production of a medicinal product for the treatment of Cushing syndrome.

According to a further aspect of the invention, the use of at least one compound of general formula (I) as defined above or of a physiologically acceptable salt thereof is provided for the treatment of sleep disorders and/or for the production of a medicinal product for the treatment of sleep disorders.

According to a further aspect of the invention, a method is provided for the treatment and/or prophylaxis of at least one disease selected from the group comprising diabetes insipidus, enuresis nocturna, incontinence, diseases in which disturbances of blood clotting occur and for delaying micturition in a patient, characterized in that the patient is administered an effective amount of at least one compound of general formula (I) as defined above or according to one of Claims 1 to 21 or of a physiologically acceptable salt thereof.

According to a further aspect of the invention, a method is provided for the treatment and/or prophylaxis of at least one disease selected from the group comprising hypertension, pulmonary hypertension, heart failure, myocardial infarction, coronary spasm, unstable angina, PTCA (percutaneous transluminal coronary angioplasty), ischaemic heart diseases, disorders of the renal system, oedema, renal vasospasm, necrosis of the renal cortex, hyponatraemia, hypokalaemia, Schwartz-Bartter syndrome, disorders of the gastrointestinal tract, gastric vasospasm, hepatic cirrhosis, gastrointestinal ulcer, vomiting, vomiting associated with chemotherapy, and travel sickness in a patient, characterized in that the patient is administered an effective amount of at least one compound of general formula (I) as above or according to one of Claims 1 to 21 or of a physiologically acceptable salt thereof.

According to a further aspect of the invention, a method is provided for the treatment and/or prophylaxis of affective disorders in a patient, characterized in that the patient is administered an effective amount of at least one compound of general formula (I) as above or according to one of Claims 1 to 21 or of a physiologically acceptable salt thereof.

According to a further aspect of the invention, a method is provided for the treatment of anxiety disorders and/or stress-related anxiety disorders in a patient, characterized in that the patient is administered an effective amount of at least one compound of general formula (I) as above or according to one of Claims 1 to 21 or of a physiologically acceptable salt thereof.

According to a further aspect of the invention, a method is provided for the treatment of memory disorders and/or Alzheimer's disease in a patient, characterized in that the patient is administered an effective amount of at least one compound of general formula (I) as defined above or according to one of Claims 1 to 21 or of a physiologically acceptable salt thereof.

According to a further aspect of the invention, a method is provided for the treatment of psychoses and/or psychotic disorders in a patient, characterized in that the patient is administered an effective amount of at least one compound of general formula (I) as defined above or according to one of Claims 1 to 21 or of a physiologically acceptable salt thereof.

According to a further aspect of the invention, a method is provided for the treatment of Cushing syndrome in a patient, characterized in that the patient is administered an effective amount of at least one compound of general formula (I) as defined above or according to one of Claims 1 to 21 or of a physiologically acceptable salt thereof.

According to a further aspect of the invention, a method is provided for the treatment of sleep disorders in a patient, characterized in that the patient is administered an effective amount of at least one compound of general formula (I) as defined above or according to one of Claims 1 to 21 or of a physiologically acceptable salt thereof.

According to a preferred embodiment, the use of at least one compound of general formula (I) as defined above or according to one of Claims 1 to 21 or of a physiologically acceptable salt thereof is provided for inhibiting the development of tolerance to analgesic effects that are produced by the administration of analgesics, such as morphines.

According to a further aspect of the invention, a method is provided for inhibiting the development of tolerance to analgesic effects that are produced by the administration of analgesics, such as morphines, in a patient, characterized in that the patient is administered an effective amount of at least one compound of general formula (I) according to one of Claims 1 to 21 or of a physiologically acceptable salt thereof.

The aforementioned patients are preferably mammals, and quite especially humans and non-human mammals (non-human animals).

According to a further embodiment, the following compounds of the aforementioned general formula (I) are especially preferred: Compounds of Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121 and 122 and the physiologically acceptable salts thereof.

According to a further embodiment, the following compounds of the aforementioned general formula (I) are especially preferred: Compounds of Examples 123 to 242 and the physiologically acceptable salts thereof.

According to a further embodiment, the following compounds of the aforementioned general formula (I) are especially preferred: Compounds of Examples 243 to 362 and the physiologically acceptable salts thereof.

According to a further embodiment, the following compounds of the aforementioned general formula (I) are especially preferred: Compounds of Examples 363 to 482 and the physiologically acceptable salts thereof.

According to a further embodiment, the following compounds of the aforementioned general formula (I) are especially preferred: Compounds of Examples 483 to 602 and the physiologically acceptable salts thereof.

According to a further embodiment, the following compounds of the aforementioned general formula (I) are especially preferred: Compounds of Examples 603 to 722 and the physiologically acceptable salts thereof.

According to a further embodiment, the following compounds of the aforementioned general formula (I) are especially preferred: Compounds of Examples 723 to 842 and the physiologically acceptable salts thereof.

According to a further embodiment, the following compounds of the aforementioned general formula (I) are especially preferred: Compounds of Examples 843 to 962 and the physiologically acceptable salts thereof.

According to a further embodiment, the following compounds of the aforementioned general formula (I) are especially preferred: Compounds of Examples 963 to 1082 and the physiologically acceptable salts thereof.

The compounds according to the invention can be in the form of racemates or as enantiomerically pure or diastereomerically pure compounds. Preferably the compounds are in the form of enantiomerically pure or diastereomerically pure compounds.

Physiologically compatible salts can be formed for example with the following anions:

Chloride, bromide, phosphate, carbonate, nitrate, perchlorate, sulphate, citrate, lactate, tartrate, maleate, fumarate, mandelate, benzoate, ascorbate, cinnamate, glycolate, methanesulphonate, formate, malonate, naphthalene-2-sulphonate, tosylates, salicylate and/or acetate. Other suitable acids are listed for example in "Fortschritte der Arzneimittelforschung", 1966, Birkhäuser Verlag, Vol. 10, p. 224-285.

In the sense of the present description, the terms "alkyl" or "alkylene" always comprise linear or branched "alkyl" or "alkylene".

$C_1$-$C_4$-alkyl is, in the sense of the description, preferably methyl, ethyl, n-propyl, i-propyl, n-butyl, sec-butyl or t-butyl.

$C_0$-alkylene or $(CH_2)_0$ denote, in the sense of the description, a single bond or hydrogen.

The terms alkyl, $C_1$-$C_6$-alkyl, $C_1$-$C_5$-alkyl and $C_1$-$C_4$-alkyl denote, in the sense of the description, a linear or branched saturated hydrocarbon chain with the number of carbon atoms stated in each case, preferably 1 to 6, more preferably 1 to 4 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 1,2-dimethylpropyl, 1,1-dimethylpropyl, 2,2-dimethylpropyl, 1-ethylpropyl, n-hexyl, 1-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl or 1-ethyl-2-methylpropyl, preferably methyl, ethyl, propyl, n-butyl or i-butyl.

The terms alkylene, $C_1$-$C_6$-alkylene and $C_1$-$C_4$-alkylene denote, in the sense of the description, an alkyl group, as defined above, in which a hydrogen atom is replaced with a bond. In particular we may mention for example methylene, eth-1,2-ylene, prop-1,2-ylene, prop-1,3-ylene, but-1,2-ylene, but-1,3-ylene, but-2,3-ylene, but-1,4-ylene, 2-methylprop-1,3-ylene, pent-1,2-ylene, pent-1,3-ylene, pent-1,4-ylene, pent-1,5-ylene, pent-2,3-ylene, pent-2,4-ylene, 1-methylbut-1,4-ylene, 2-methylbut-1,4-ylene, 2-methylbut-1,3-ylene, 2-ethylprop-1,3-ylene, hex-3,4-ylene, 3-methylpent-2,4-ylene, hept-3,5-ylene, 2-ethylpent-1,3-ylene, 3-ethylhept-3,5-ylene, etc., preferably methylene, eth-1,2-ylene and prop-1,2-ylene.

The terms aryl, $C_6$-$C_{20}$-aryl and $C_6$-$C_{10}$-aryl denote, in each case in the sense of the description, an aromatic mono-, bi- or polycyclic residue preferably with 6 to 20 carbon atoms, more preferably 6 to 10 carbon atoms and preferably selected from phenyl, biphenyl, naphthyl, tetrahydronaphthyl, fluorenyl, indenyl and phenanthrenyl, more preferably from phenyl and naphthyl, such as 1-naphthyl or 2-naphthyl. Phenyl is the most preferred.

The terms hetaryl, $C_6$-$C_{20}$-hetaryl, $C_6$-$C_{10}$-hetaryl, $C_1$-$C_{10}$-hetaryl, $C_2$-$C_{10}$-hetaryl, $C_3$-$C_{10}$-hetaryl, $C_1$-$C_6$-hetaryl and $C_1$-$C_5$-hetaryl denote, unless stated otherwise in the sense of the description, an aromatic ring containing at least one heteroatom, preferably 1 or 2 heteroatoms, selected from the group O, N or S and 1 to 10, preferably 2 to 10, more preferably 3 to 10, especially preferably 1 to 6, and even more preferably 1 to 5 carbon atoms. The aromatic ring is preferably 5- or 6-membered. Hetaryl additionally comprises the derivatives thereof fused with aryl, namely an aromatic residue with preferably 6 to 20 carbon atoms, more preferably 6 to 10 carbon atoms, most preferably phenyl, which is fused with this aromatic ring, containing at least one heteroatom. Hetaryl can also be selected from an aromatic residue with preferably 6 to 20, more preferably 6 to 10 carbon atoms, most preferably phenyl, with a heterocycloalkyl group, which is fused to it. The heterocycloalkyl group is then as defined above. Hetaryl is preferably selected from 2-furyl, 3-furyl, 2-pyrrolyl, 3-pyrrolyl, 2-thienyl, 3-thienyl, 2-pyridyl, 3-pyridyl, 4-pyridyl, 2-thiazolyl, 4-thiazolyl, 5-thiazolyl, 2-oxazolyl, 4-oxazolyl, 5-oxazolyl, 2-pyrimidyl, 4-pyrimidyl, 5-pyrimidyl, 6-pyrimidyl, 3-pyrazolyl, 4-pyrazolyl, 5-pyrazolyl, 3-isothiazolyl, 4-isothiazolyl, 5-isothiazolyl, 2-imidazolyl, 4-imidazolyl, 5-imidazolyl, 3-pyridazinyl, 4-pyridazinyl, 5-pyridazinyl, 6-pyridazinyl, 3-isoxazolyl, 4-isoxazolyl, 5-isoxazolyl, thiadiazolyl, oxadiazolyl, triazinyl, indolynyl, benzothienyl, naphthothienyl, benzofuranyl, chromenyl, indolyl, isoindolyl, indazolyl, quinolyl, isoquinolyl, phthalazinyl, quinoxalinyl, benzimidazolyl and benzoxazolyl, 2,3-dihydro-1,4-benzodioxinyl, 1,3-benzodioxolyl, 2,1,3-benzothiadiazolyl.

The terms cycloalkyl, $C_3$-$C_7$-cycloalkyl and $C_3$-$C_6$-cycloalkyl denote, in the sense of the description, a saturated hydrocarbon ring with 3 to 7, preferably 3 to 6 carbon atoms, such as cyclopropyl, cyclobutyl, cyclopentyl, cyclohexyl or cycloheptyl.

$C_3$-$C_7$-cycloalkenyl is, in the sense of the description, a $C_3$-$C_7$-cycloalkyl, as defined above, which has one, two, three, four or more double bonds.

$C_3$-$C_7$-heterocycloalkyl is, in the sense of the description, a $C_3$-$C_7$-cycloalkyl, as defined above, with 1, 2, 3 or 4 identical or different heteroatoms selected from the group comprising N, O and S.

$C_3$-$C_7$-heterocycloalkenyl is, in the sense of the description, a $C_3$-$C_7$-cycloalkenyl, as defined above, with 1, 2, 3 or 4 identical or different heteroatoms selected from the group comprising N, O and S.

$C_1$-$C_6$-haloalkyl is, in the sense of the description, a $C_1$-$C_6$-alkyl, as defined above, in which one, several or all hydrogen atoms have been replaced with identical or different halogen atoms, as defined below.

$C_1$-$C_6$-haloalkoxy is, in the sense of the description, a $C_1$-$C_6$-alkoxy, as defined above, in which one, several or all hydrogen atoms have been replaced with identical or different halogen atoms, as defined below.

The terms acyl and $C_1$-$C_6$-acyl denote, in the sense of the description, a linear or branched residue —C(=O)—X, where unsubstituted or substituted residue can denote $C_1$-$C_5$-alkyl, $C_2$-$C_5$-alkenyl or $C_2$-$C_5$-alkynyl, which are as defined above.

The terms alkenyl, $C_2$-$C_6$-alkenyl, $C_2$-$C_5$-alkenyl and $C_2$-$C_4$-alkenyl denote, in the sense of the description, a linear or branched hydrocarbon chain, containing at least one double bond, with 2 to 6, preferably 2 to 4 carbon atoms.

Preferably alkenyl contains one or two double bonds, most preferably one double bond. Examples of the alkenyl groups are those as stated above for alkyl, where these groups contain one or two double bonds, for example vinyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl, 2-butenyl, 3-methyl-2-butenyl or 3-methyl-2-pentenyl.

The terms alkynyl, $C_2$-$C_6$-alkynyl, $C_2$-$C_5$-alkynyl and $C_2$-$C_4$-alkynyl denote, in the sense of the description, a linear or branched hydrocarbon chain, containing at least one triple bond with 2 to 6, preferably 2 to 4 carbon atoms. Preferably alkynyl contains one or two triple bonds, most preferably one triple bond. Examples of the alkynyl groups are those as stated above for alkyl, where these groups contain one or two triple bonds, for example ethynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl, preferably ethynyl, 2-propynyl, 2-butynyl, 1-methyl-2-propynyl or 1-methyl-2-butynyl.

$C_2$-$C_6$-alkenyloxy is, in the sense of the description, a $C_2$-$C_6$-alkenyl bound via oxygen, as defined above.

$C_2$-$C_6$-alkynyloxy is, in the sense of the description, a $C_2$-$C_6$-alkynyl bound via oxygen, as defined above.

The terms alkylthio, $C_1$-$C_6$-alkylthio, $C_1$-$C_4$-alkylthio and $C_1$-$C_2$-alkylthio denote, in the sense of the description, a linear or branched alkylenesulphanyl chain, which contains 1 to 6 carbon atoms and a sulphur atom. Preferably the alkylene residue contains 1 to 4, more preferably 1 or 2 carbon atoms, where alkylene is as defined above. Examples of thioalkyl include thiomethyl or thio-tert-butyl.

$C_1$-$C_6$-alkylamino is, in the sense of the description, a $C_1$-$C_6$-alkyl bound via nitrogen, as defined above.

$C_1$-$C_6$-acylamino is, in the sense of the description, a $C_1$-$C_6$-acyl bound via nitrogen, as defined above.

Aryloxy or —O-aryl is an aryl bound via oxygen, as defined above, in particular —O-phenyl.

The term 3- to 10-membered carbon ring denotes, in the sense of the description, a saturated or partially unsaturated hydrocarbon ring with 3 to 10 carbon atoms, for example cyclopropyl, cyclobutyl, cyclopentyl, cyclohexyl, cycloheptyl, cyclooctyl, cyclononyl or cyclodecanyl.

Alkylenaryl is an aryl bound via $C_1$-$C_6$-, more preferably $C_1$-$C_4$-alkylene, optionally substituted in the aryl residue, with alkylene and aryl as defined previously. Alkylenaryl is in particular benzyl or phenethyl optionally substituted in the aryl residue.

The terms aryloxy, $C_1$-$C_6$-aryloxy or —O-aryl denote, in the sense of the description, an aryl bound via oxygen, as defined above, in particular —O-phenyl.

Alkylenehetaryl is a hetaryl bound via $C_1$-$C_6$-, more preferably $C_1$-$C_4$-alkylene, optionally substituted in the hetaryl residue, where alkylene and hetaryl are as defined here. Alkylenehetaryl is preferably optionally substituted —$CH_2$-2-pyridyl, —$CH_2$-3-pyridyl, —$CH_2$-4-pyridyl, —$CH_2$-2-thienyl, —$CH_2$-3-thienyl, —$CH_2$-2-thiazolyl, —$CH_2$-4-thiazolyl, —$CH_2$-5-thiazolyl, —$CH_2$—$CH_2$-2-pyridyl, —$CH_2$—$CH_2$-3-pyridyl, —$CH_2$—$CH_2$-4-pyridyl, —$CH_2$—$CH_2$-2-thienyl, —$CH_2$—$CH_2$-3-thienyl, —$CH_2$—$CH_2$-2-thiazolyl, —$CH_2$—$CH_2$-4-thiazolyl or —$CH_2$—$CH_2$-5-thiazolyl.

A bi- or tricyclic, saturated hydrocarbon residue is a bicycloalkyl- or tricycloalkyl residue and has 5 to 18 carbon atoms. In a bicycloalkyl residue the ring system preferably contains 5 to 12, more preferably 6 to 10 carbon atoms, and in a tricycloalkyl residue the ring system preferably contains 6 to 16, more preferably 6 to 12 carbon atoms. Examples of a bicycloalkyl residue include indanyl, camphyl and norbornyl. Examples of a tricycloalkyl residue include adamantyl.

Halogen is a halogen atom selected from fluorine, chlorine, bromine or iodine, preferably fluorine, chlorine or bromine, more preferably fluorine or chlorine.

Halogen-substituted alkyl denotes an alkyl residue, as defined above, which is substituted partially or fully with fluorine, chlorine, bromine and/or iodine, i.e. for example $CH_2F$, $CHF_2$, $CH_2Cl$, 2-fluoroethyl, 2-chloroethyl, 2,2,2-trifluoroethyl.

The expression "substituted $C_1$-$C_4$-alkyl" in the sense of the present invention denotes that some or all hydrogen atoms of the "$C_1$-$C_4$-alkyl" residue have been replaced with identical, different or partly identical and partly different substituents other than hydrogen. The maximum possible number of substituents is predetermined by the number of hydrogen atoms. The preferred number of substituents is one, two, three or four substituents. Preferred substituents are halogen, $C_1$-$C_6$-alkyl, O—$C_1$-$C_6$-alkyl, $C_3$-$C_7$-cycloalkyl, $C_1$-$C_6$-haloalkyl, O—$C_1$-$C_6$-haloalkyl or $C_6$-$C_{10}$-aryl.

What is said above regarding the expression "substituted $C_1$-$C_4$-alkyl" shall also apply analogously to the expressions "substituted $C_3$-$C_6$-cycloalkyl", "substituted phenyl".

If mentioned, the residues and groups can preferably be substituted singly or multiply, more preferably singly, doubly or triply, most preferably singly or doubly. The expression "in each case optionally substituted" is to denote that not only the immediately following residue, but all residues stated in the particular group, can be substituted.

Examples of the substituents comprise: halogen, CN, $CF_3$, $CHF_2$, $OCF_3$, $OCHF_2$, $NO_2$, $NH_2$, OH, COOH, linear or branched in each case, optionally substituted $C_1$-$C_6$-alkyl, $C_3$-$C_7$-cycloalkyl, $C_1$-$C_6$-alkylene-O—$C_1$-$C_6$-alkyl or $C_1$-$C_6$-thioalkyl, O—$C_1$-$C_4$-alkyl, N($C_1$-$C_4$-alkyl)$_2$, NH($C_1$-$C_4$-alkyl), aryl, —O-aryl, $C_1$-$C_4$-alkylene-O-aryl, NHCO—$C_1$-$C_4$-alkyl, NH—$SO_2$—$C_1$-$C_4$-alkyl, CO—$C_{1\text{-}4}$-alkyl, $SO_2$—$C_1$-$C_4$-alkyl, and NHCO-aryl, $NHSO_2$-aryl, $CONH_2$, $SO_2NH_2$, $SO_2$-aryl, SO—$C_1$-$C_4$-alkyl, SO-aryl, n-pyrrolidinyl, n-piperidynyl, and n-morpholinyl optionally substituted in the aryl residue. Preferred substituents are F, Cl, $CF_3$, $OCF_3$, $NH_2$, $NO_2$, OH, COOH, $C_1$-$C_4$-alkyl, methoxy, acetyl, NH-acetyl and $SO_2NH_2$.

Expressions in parentheses with superscript integers are to be understood, in the sense of the description, in the way that the meanings of the residues in parentheses can in each case be identical or different. For example, in the sense of the description $N(C_1-C_4\text{-alkyl})_2$ stands for $N(C_1-C_4\text{-alkyl})(C_1-C_4\text{-alkyl})$, where the two residues ($C_1-C_4$-alkyl) can be identical or different. $C_0-C_6$-alkyl stands for hydrogen or $C_1-C_6$-alkyl.

The symbol ≠) in the chemical formulae of $R^Y$ and Z represents the points of attachment of $R^Y$ at position 3 of the oxindole ring structure or the points of attachment of $R^Y$ and Z, respectively.

The expressions "compounds" and "at least one compound" in the sense of the invention are equivalent and denote that one or more of the stated compounds are referred to.

The compounds according to the invention are effective after administration by various routes (for example intravenous, intramuscular, oral), in particular oral.

The compounds according to the invention show good affinity for vasopressin receptors, for example the vasopressin receptor subtypes V1a and V1b. As the various vasopressin receptors transmit very varied effects of vasopressin (M. Thibonnier, Exp. Opin. Invest. Drugs 1998, 7(5), 729-740; Serradeil-Le Gal, C, et al.; Prog Brain Res. 2002; 139: 197-210), it is especially important to obtain effects selectively on for example a vasopressin receptor, in order to achieve the desired effect without at the same time causing appreciable side effects. Thus, vasopressin exerts effects, for example via the V2 receptor, on the kidneys and their function, and this would be undesirable if, say, CNS disorders were being treated. Accordingly, as well as the actual affinity at the target receptor, selectivity with respect to the other vasopressin receptors is also particularly important. The compounds according to the invention offer the advantage of having very good affinities for the desired receptors such as the vasopressin receptors V1b and V1a and at the same time displaying improved selectivity with respect to the other receptors such as V2.

Preferred compounds of the general formula (I), their salts, their prodrugs or their N-oxides are distinguished by a binding affinity Ki for the vasopressin V1b receptor subtype of less than about 500 nM, in particular <50 nM. Compounds of the formula (I) with a Ki of less than or equal to 20 nM are particularly preferred.

Preferred compounds of the general formula (I), their salts, their prodrugs or their N-oxides are further distinguished by having a selectivity for the vasopressin V1b receptor subtype vis-a-vis at least one of the closely related vasopressin/oxytocin receptor subtypes (for example vasopressin V1a, vasopressin V2 and/or oxytocin). The selectivity, expressed as the ratio of the Ki values, e.g. Ki(V1a)/Ki(V1b) or Ki(V2)/Ki(V1b) is usually >1, often >5, in particular >10 and specifically >20.

Preferred compounds of the general formula (I), their salts, their prodrugs or their N-oxides are further distinguished by having an improved metabolic stability.

The metabolic stability of a compound can be determined for example by incubating a solution of this compound with liver microsomes from particular species (for example rat, dog or human) and determining the half-life of the compound under these conditions (R S Obach, Curr Opin Drug Discov Devel. 2001, 4, 36-44). It is possible to conclude from larger half-lives that the metabolic stability of the compound is improved. The stability in the presence of human liver microsomes is of particular interest since it makes it possible to predict the metabolic degradation of the compound in the human liver. Compounds with increased metabolic stability are therefore probably also degraded more slowly in the liver. The slower metabolic degradation in the liver usually leads to higher and/or longer-lasting concentrations (effective levels) of the compound in the body and specifically in the brain, so that the elimination half-life of the compounds of the invention is increased. Increased and/or longer-lasting effective levels may lead to a better efficacy of the compound in the treatment or prophylaxis of various vasopressin-dependent or oxytocin-dependent diseases. An improved metabolic stability may additionally lead to an increased bioavailability after oral administration, because the compound is subjected, after being absorbed in the intestine, to less metabolic degradation in the liver (so-called first pass effect). An increased oral bioavailability may, because the concentration (effective level) of the compound is increased, lead to a better efficacy of the compound of the formula I after oral administration.

The present invention also provides the use of the compounds according to the invention for the treatment and/or prophylaxis of diseases in which the course of the disease depends at least partly on vasopressin, i.e. diseases that display a raised vasopressin or oxytocin level, which can contribute indirectly or directly to the clinical picture.

Furthermore, the present invention provides the use of the compounds according to the invention for the treatment and/or prophylaxis of diseases such as diabetes insipidus, enuresis nocturna, incontinence, diseases in which disturbances of blood clotting occur and/or for delaying micturition.

The present invention also makes the use of the compounds according to the invention available for the treatment and/or prophylaxis of the following diseases: hypertension, pulmonary hypertension, heart failure, myocardial infarction, coronary spasm, unstable angina, PTCA (percutaneous transluminal coronary angioplasty), ischaemic heart diseases, disorders of the renal system, oedema, renal vasospasm, necrosis of the renal cortex, hyponatraemia, hypokalaemia, Schwartz-Bartter syndrome, disorders of the gastrointestinal tract, gastritis-associated vasospasm, hepatic cirrhosis, gastrointestinal ulcer, vomiting, vomiting associated with chemotherapy, and travel sickness.

The compounds according to the invention can also be used for the treatment of various vasopressin-dependent or oxytocin-dependent disorders, which have central-nervous causes or changes in the HPA axis (hypothalamic pituitary adrenal axis), for example in affective disorders, such as depressive disorders and bipolar disorders. These include for example dysthymic disorders, phobias, posttraumatic stress disorders, general anxiety disorders, panic disorders, seasonal depressions and sleep disorders.

The compounds according to the invention can also be used for the treatment of anxiety disorders and stress-related anxiety disorders, for example generalized anxiety disorders, phobias, posttraumatic anxiety disorders, panic anxiety disorders, obsessive-compulsive anxiety disorders, acute stress-related anxiety disorders and social phobia. Furthermore, the compounds according to the invention are also used for the treatment of memory disorders, Alzheimer's disease, psychoses, psychotic disorders, sleep disorders and/or Cushing syndrome.

The present invention also relates to pharmaceutical compositions that contain an effective dose of a compound according to the invention or of a pharmaceutically compatible salt thereof and suitable excipients.

These excipients are selected according to the pharmaceutical form and the desired route of administration.

The compounds according to the invention of general formula (I) or optionally suitable salts of these compounds can be used for the production of pharmaceutical compositions for oral, sublingual, subcutaneous, intramuscular, intravenous, topical, intratracheal, intranasal, transdermal or rectal administration and are administered to animals or humans in unitary dosage forms, mixed with conventional pharmaceutical excipients, for the prophylaxis or treatment of the above disorders or diseases.

The suitable unitary dosage forms include forms for oral administration, such as tablets, gelatin capsules, powder, granules, and oral solutions or suspensions, forms for sublingual, buccal, intratracheal or intranasal administration, aerosols, implants, forms for subcutaneous, intramuscular or intravenous administration and forms for rectal administration.

For topical administration, the compounds according to the invention can be used in creams, ointments or lotions.

In order to achieve the desired prophylactic or therapeutic effect, the dose of the active ingredient can vary between 0.01 and 50 mg per kg body weight and per day.

Each unit dose can contain 0.05 to 5000 mg, preferably 1 to 1000 mg, of the active ingredient in combination with a pharmaceutical excipient. This unit dose can be administered 1 to 5 times daily, so that a daily dose from 0.05 to 25000 mg, preferably 1 to 5000 mg, is administered.

If a solid composition in the form of tablets is prepared, the main ingredient is mixed with an excipient, such as gelatin, starch, lactose, magnesium stearate, talc, silica or the like.

The tablets can be coated with sucrose, a cellulose derivative or some other suitable substance or can be treated in some other way, in order to display continuous or delayed activity and in order to release a predetermined amount of the active ingredient continuously.

A preparation in the form of gelatin capsules is obtained by mixing the active ingredient with a diluent and filling the resultant mixture in soft or hard gelatin capsules.

A preparation in the form of a syrup or elixir or for administration in the form of drops can contain active ingredients together with a sweetener, which is preferably calorie-free, methylparaben or propylparaben as antiseptics, a flavouring agent and a suitable colorant.

The water-dispersible powder or granules can contain the active ingredients, mixed with dispersants, wetting agents or suspending agents, such as polyvinylpyrrolidones, and sweeteners or taste-modifying agents.

Rectal administration is achieved by using suppositories, which are prepared with binders that melt at rectal temperature, for example cocoa butter or polyethylene glycols. Parenteral administration is accomplished using aqueous suspensions, isotonic salt solutions or sterile and injectable solutions, which contain pharmacologically compatible dispersants and/or wetting agents, for example propylene glycol or polyethylene glycol.

The active ingredient can also be formulated as microcapsules or centrosomes, if suitable with one or more excipients or additives.

In addition to the compounds of general formula (I) or their pharmaceutically compatible salts, the compositions according to the invention can contain other active ingredients that can be used for the treatment of the aforementioned disorders or diseases.

The present invention thus further relates to pharmaceutical compositions in which several active ingredients are present together, with at least one of these being a compound according to the invention.

The compounds according to the invention are antagonists of the so-called receptors of the vasopressin-oxytocin class. Such compounds can be investigated in suitable tests that determine the affinity for a receptor, where the affinity constant Ki represents a measure for the potency of the compounds, with a smaller value corresponding to greater potency. The compounds according to the invention were tested for example for their receptor affinity with respect to the vasopressin receptor subtypes V1b, V1a, V2 and/or the oxytocin receptor.

PRODUCTION OF THE COMPOUNDS ACCORDING TO THE INVENTION

Examples of synthetic routes for production of the compounds according to the invention are described below.

Production of the oxindoles according to the invention can for example take place by the route depicted in synthesis scheme 1. In synthesis scheme 1, the variables have the same meanings as in general formula (I).

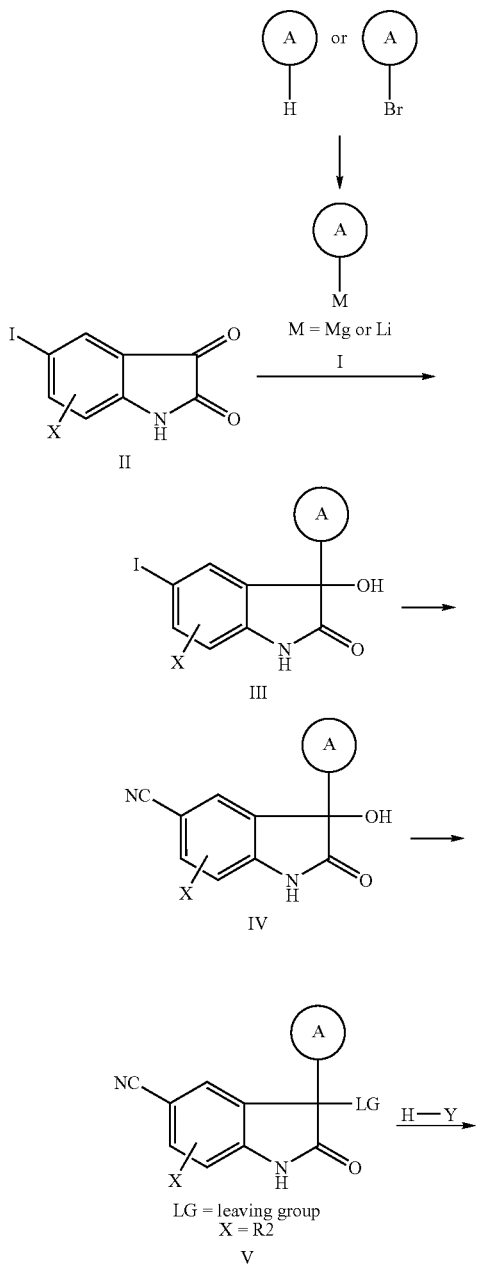

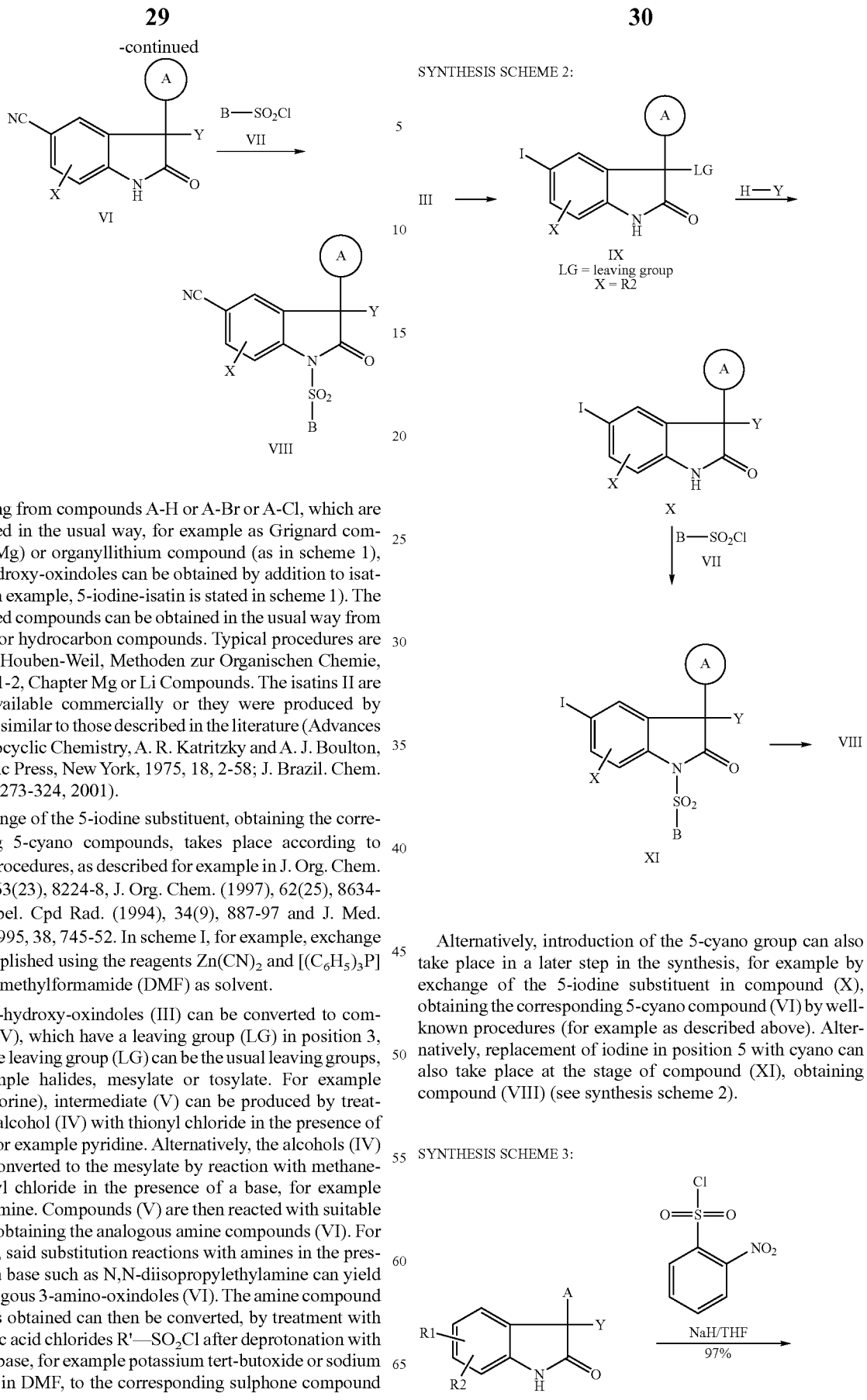

Starting from compounds A-H or A-Br or A-Cl, which are metallated in the usual way, for example as Grignard compound (Mg) or organyllithium compound (as in scheme 1), the 3-hydroxy-oxindoles can be obtained by addition to isatins (as an example, 5-iodine-isatin is stated in scheme 1). The metallated compounds can be obtained in the usual way from halogen or hydrocarbon compounds. Typical procedures are given in Houben-Weil, Methoden zur Organischen Chemie, Vol. 13, 1-2, Chapter Mg or Li Compounds. The isatins II are either available commercially or they were produced by methods similar to those described in the literature (Advances in Heterocyclic Chemistry, A. R. Katritzky and A. J. Boulton, Academic Press, New York, 1975, 18, 2-58; J. Brazil. Chem. Soc. 12, 273-324, 2001).

Exchange of the 5-iodine substituent, obtaining the corresponding 5-cyano compounds, takes place according to known procedures, as described for example in J. Org. Chem. (1998), 63(23), 8224-8, J. Org. Chem. (1997), 62(25), 8634-9, J. Label. Cpd Rad. (1994), 34(9), 887-97 and J. Med. Chem. 1995, 38, 745-52. In scheme I, for example, exchange is accomplished using the reagents $Zn(CN)_2$ and $[(C_6H_5)_3P]_4Pd$ in dimethylformamide (DMF) as solvent.

The 3-hydroxy-oxindoles (III) can be converted to compounds (V), which have a leaving group (LG) in position 3, where the leaving group (LG) can be the usual leaving groups, for example halides, mesylate or tosylate. For example (LG=chlorine), intermediate (V) can be produced by treatment of alcohol (IV) with thionyl chloride in the presence of a base, for example pyridine. Alternatively, the alcohols (IV) can be converted to the mesylate by reaction with methanesulphonyl chloride in the presence of a base, for example triethylamine. Compounds (V) are then reacted with suitable amines, obtaining the analogous amine compounds (VI). For example, said substitution reactions with amines in the presence of a base such as N,N-diisopropylethylamine can yield the analogous 3-amino-oxindoles (VI). The amine compound (VI) thus obtained can then be converted, by treatment with sulphonic acid chlorides R'—$SO_2Cl$ after deprotonation with a strong base, for example potassium tert-butoxide or sodium hydride, in DMF, to the corresponding sulphone compound (VII).

Alternatively, introduction of the 5-cyano group can also take place in a later step in the synthesis, for example by exchange of the 5-iodine substituent in compound (X), obtaining the corresponding 5-cyano compound (VI) by well-known procedures (for example as described above). Alternatively, replacement of iodine in position 5 with cyano can also take place at the stage of compound (XI), obtaining compound (VIII) (see synthesis scheme 2).

-continued

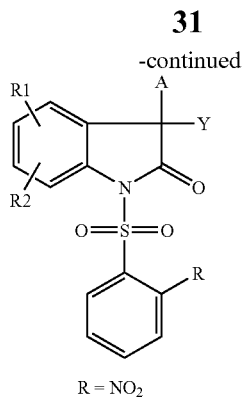

R = NO₂

H₂, Pd/C
42%

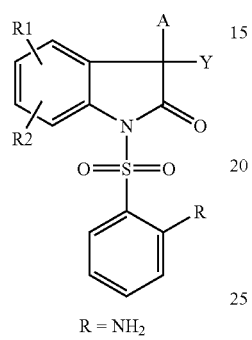

R = NH₂

Compounds I in which B is 2-aminophenylsulphonyl can be prepared for example starting from compound X by reacting X with 2-nitrobenzenesulphonyl chloride, which can be purchased, and reducing (e.g. by catalytic hydrogenation) the nitro group in the compound I obtained in this way.

Phenylsulphonyl chlorides can be prepared in analogy to the methods shown in schemes 4, 4a and 4b:

SYNTHESIS SCHEME 4:

a) B—H  $\xrightarrow{\text{bistrimethylsilyl sulfate}}$  B—SO₂Cl
VIII b) B—Br  $\xrightarrow[\text{2. SO}_2]{\text{1. butyllithium}}$  B—SO₂Li  $\xrightarrow{\text{SO}_2Cl_2}$  B—SO₂Cl
VIII Reaction a) takes place in analogy to the method described in J. Med. Chem. 2001, 36, 809-828.

Reaction b) takes place in analogy to the method described in Synthesis 1986, 852. The reactions are shown by way of example in schemes 4a and 4b.

SYNTHESIS SCHEME 4a:

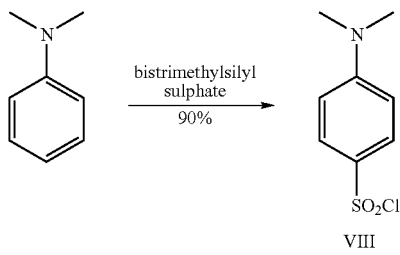

VIII

SYNTHESIS SCHEME 4b:

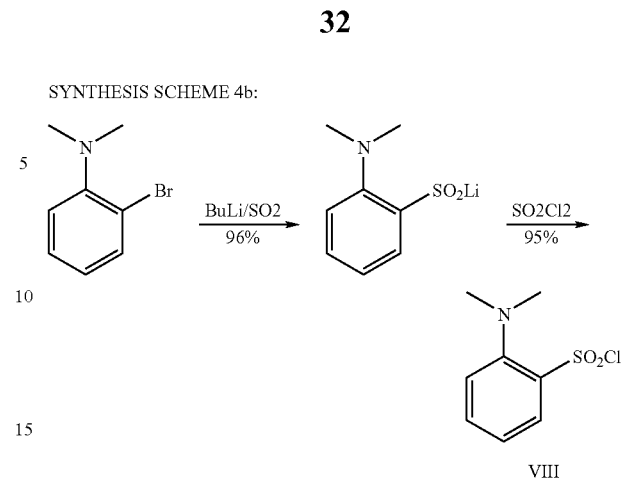

VIII

One of the preferred Y residues is an optionally substituted pyridin-4-ylpiperazin-1-yl. The corresponding optionally substituted pyridin-4-ylpiperazine and its N-oxide can be prepared by the method described in Chem. Pharm. Bull. 2001, 41, 1314-1320. Synthesis of the pyridin-4-ylpiperazine is depicted in scheme 5:

SYNTHESIS SCHEME 5:

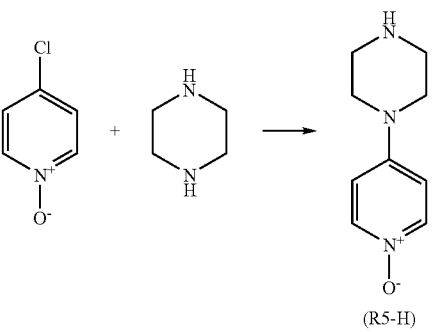

(R5-H)

Reaction takes place according to the reaction conditions described in Chem. Pharm. Bull. 2001, 41, 1314-20, page 1319.

Other compounds Y—H can also be prepared in an analogous manner. A further synthesis of compounds I is depicted in scheme 6 below:

SYNTHESIS SCHEME 6:

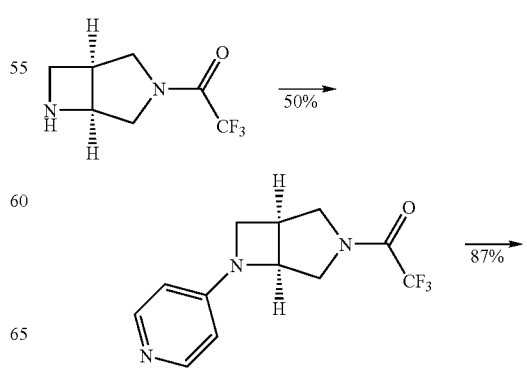

SYNTHESIS SCHEME 7:

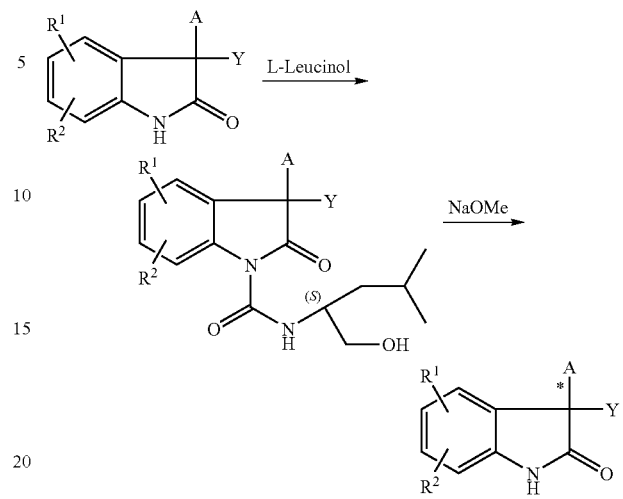

Chiral separation of the enantiomers with L-leucinol can be carried out for example as described in WO 03/008407, pages 26 and 27 and 79 and 80. Alternatively the enantiomers can be separated by HPLC on chiral separating columns, e.g. separating column: Chiracel OD 250×4.6×10 mm; eluate: hexane:EtOH:NEt3 850:150:1.

The invention is explained in more detail below on the basis of examples, but is not restricted to the examples.

EXPERIMENTAL SECTION

Example 1

5-Chloro-3-(2-methoxyphenyl)-3-(4-pyridin-3-yl-piperazin-1-yl)-1,3-dihydro-indol-2-one Pyridine (0.18 mL, 2.24 mmol) and thionyl chloride (0.16 mL, 2.24 mmol) were added to a solution of 5-chloro-3-hydroxy-3-(2-methoxyphenyl)-1,3-dihydro-indol-2-one (WO 2005/030755, 0.50 g, 1.73 mmol) in dichloromethane (40 mL) with ice cooling, and stirred for 45 min at 0° C. The reaction solution was quenched with water, while stirring, and the preparation was extracted with dichloromethane. The organic phase was washed with water and saturated sodium chloride solution, dried over sodium sulphate and concentrated at reduced pressure. N,N-diisopropylethylamine (0.81 mL, 4.66 mmol) and 1-pyridin-3-yl-piperazine, HCl salt (0.34 g, 1.73 mmol) were added to a solution of the 3-chloro-oxindole intermediate thus obtained in dichloromethane/THF (20 mL) and the reaction mixture was stirred for 12 h at room temperature. The reaction mixture was concentrated at reduced pressure and the residue was distributed between ethyl acetate and water. The aqueous phase was extracted with ethyl acetate again. The combined organic phase was dried over sodium sulphate and concentrated at reduced pressure, and was used further without additional purification. Yield: 0.62 g.

ESI-MS: $[M+H^+]$=435.20;

5-Chloro-1-(2,4-dimethoxy-benzenesulphonyl)-3-(2-methoxyphenyl)-3-(4-pyridin-3-yl-piperazin-1-yl)-1,3-dihydro-indol-2-one Sodium hydride (10.8 mg, 60% dispersion in mineral oil, 0.27 mmol) was added to a solution of 5-chloro-3-(2-meth-

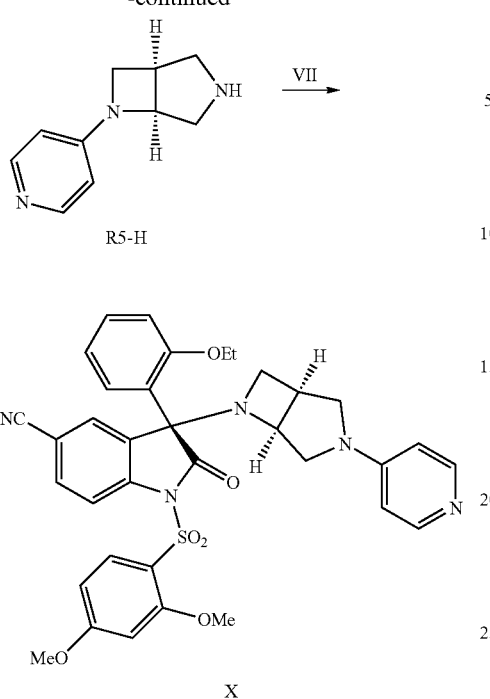

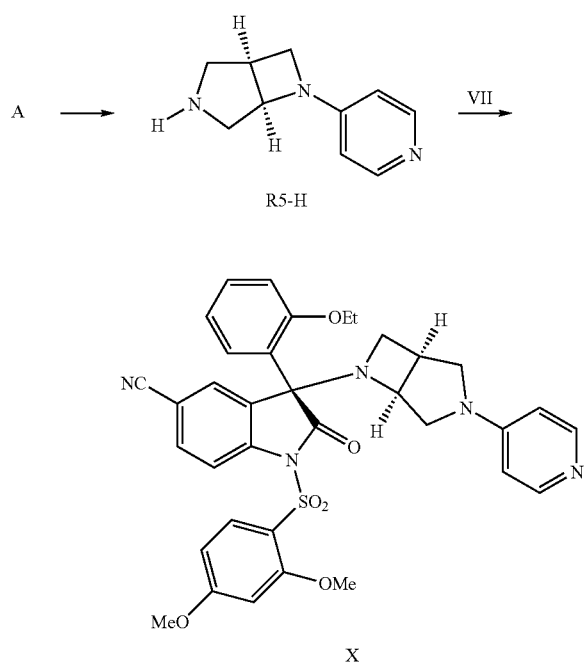

Preparation of the bicyclic 4-pyridyl derivative R5—H takes place according to the method described in Chem. Pharm. Bull. 2001, 41, 1314-1320, in particular page 1319.

The compounds according to the invention have, as already explained, a chirality centre in position 3 of the oxindole structure. Separation of the enantiomers can take place at the stage of the final products or else, as shown in scheme 7, at a preceding stage, e.g. of the compound VI. For this purpose, the compound VI is converted into an optically active urea compound.

oxyphenyl)-3-(4-pyridin-3-yl-piperazin-1-yl)-1,3-dihydro-indol-2-one (1494-71) (90.0 mg, 0.21 mmol) in THF (7 mL) at 0° C. After 1 hour, 2,4-dimethoxybenzenesulphonic acid chloride (49.0 mg, 0.21 mmol) was added to the reaction solution, with ice cooling, and stirred for 12 h at room temperature. Water was carefully added to the preparation and it was then extracted twice with ethyl acetate. The combined organic phase was washed with water and saturated sodium chloride solution, dried over sodium sulphate and concentrated at reduced pressure. The residue was purified by silica-gel chromatography (solvent gradient 0-7% methanol in dichloromethane).

Yield: 99.0 mg.

ESI-MS: 638.15; 637.15; [M+H$^+$]=636.15; 635.15; 472.10;

The following compounds 2 to 122 were prepared in a manner similar to that described in Example 1 using the synthesis steps described in the synthesis schemes. In some cases the compounds were purified by preparative reversed-phase HPLC (solvent: gradient from 10% to 80% acetonitrile in water, 0.1% trifluoroacetic acid or 0.2% acetic acid as modulator) and, provided they contain a basic nitrogen in the molecule, are obtained as salts of trifluoroacetic acid or salts of acetic acid.

Example 2

5-Cyano-1-(2,4-dimethoxy-benzenesulphonyl)-3-(2-ethoxyphenyl)-3-(4-pyridin-3-yl-piperazin-1-yl)-2,3-dihydro-1H-indol-2-one ESI-MS: 642.20; 641.25; [M+H$^+$]=640.25;
$^1$H-NMR (400 MHz, CDCl$_3$) δ (ppm): 8.20 (1H, s br.), 8.15 (1H, d), 8.08 (1H, d), 7.84 (1H, d), 7.63 (1H, d), 7.34-7.10 (4H, m+CHCl$_3$), 7.04 (1H, t), 6.80 (1H, d), 6.61 (1H, d), 6.42 (1H, s), 4.03-3.72 (5H, m), 3.64 (3H, s), 3.2 (s br.), 2.5 (s br.), 1.16 (3H, t).

Example 3

5-Chloro-1-(2,4-dimethoxy-benzenesulphonyl)-3-(2-methoxyphenyl)-3-(4-pyridin-4-yl-piperazin-1-yl)-1,3-dihydro-indol-2-one

ESI-MS: 637.15, [M+H$^+$]=636.15, 635.15;

Example 4

4-[5-Chloro-3-(2-methoxyphenyl)-2-oxo-3-(4-pyridin-4-yl-piperazin-1-yl)-2,3-dihydro-indole-1-sulphonyl]-benzonitrile ESI-MS: 603.0, 602.2, [M+H$^+$]=600.2;
$^1$H-NMR (500 MHz, CDCl$_3$) δ (ppm): 8.34 (2H, d), 8.26 (2H, s br.), 7.92-7.80 (4H, m), 7.30 (2H, t), 7.08 (1H, t), 6.89 (1H, s), 6.78 (1H, d), 6.60 (2H, m), 3.19 (3H, s), 2.6 (s br.).

Example 5

5-Chloro-1-(2-methoxy-benzenesulphonyl)-3-(2-methoxyphenyl)-3-(4-pyridin-4-yl-piperazin-1-yl)-1,3-dihydro-indol-2-one ESI-MS: 608.2, 607.2, [M+H$^+$]=606.2, 605.2, 119.2, 101.1;
$^1$H-NMR (500 MHz, CDCl$_3$) δ (ppm): 8.29-8.17 (3H, m), 7.90 (1H, d), 7.83 (1H, d), 7.57 (1H, t), 7.32-7.22 (m+CHCl$_3$), 7.14 (1H, t), 7.06 (1H, t), 6.97 (1H, d), 6.92 (1H, s), 6.81 (1H, d), 6.57 (2H, m), 3.73 (3H, s), 3.46 (3H, s), 3.0 (s br.), 2.6 (s br.).

Example 6

5-Chloro-1-(2-methoxy-4-methyl-benzenesulphonyl)-3-(2-methoxyphenyl)-3-(4-pyridin-4-yl-piperazin-1-yl)-1,3-dihydro-indol-2-one ESI-MS: 619.2;
$^1$H-NMR (500 MHz, CDCl$_3$) δ (ppm): 8.24 (2H, m), 8.08 (1H, d), 7.90 (1H, d), 7.84 (1H, d), 7.33-7.24 (2H, m+CHCl$_3$), 7.08 (1H, t), 6.97-6.89 (2H, m), 6.81 (1H, d), 6.75 (1H, s), 6.57 (2H, m), 3.70 (3H, s), 3.47 (3H, s), 3.0 (s br.), 2.6 (s br.), 2.40 (3H, s).

Example 7

5-Cyano-1-(4-cyano-benzenesulphonyl)-3-(2-ethoxyphenyl)-3-(4-pyridin-4-yl-piperazin-1-yl)-2,3-dihydro-1H-indol-2-one ESI-MS: [M+H$^+$]=602.25, 101.15;
$^1$H-NMR (400 MHz, CDCl$_3$) δ (ppm): 8.31 (2H, d), 8.26 (2H, m sym.), 8.02 (1H, d), 7.86 (2H, d), 7.81 (1H, d), 7.66 (1H, d), 7.31 (1H, t), 7.18 (1H, s), 7.08 (1H, t), 6.78 (1H, d), 6.61 (2H, m), 3.70 (2H, m sym.), 3.50-3.17 (2H, m), 2.46 (s br.).

(1494-39) ESI-MS: [M+H$^+$]=440.5;

Example 8

5-Cyano-3-(2-ethoxyphenyl)-1-(2-methoxy-benzenesulphonyl)-3-(4-pyridin-4-yl-piperazin-1-yl)-2,3-dihydro-1H-indol-2-one ESI-MS: [M+H$^+$]=610.2;
$^1$H-NMR (400 MHz, CDCl$_3$) δ (ppm): 8.23 (3H, t), 8.10 (1H, d), 7.83 (1H, d), 7.65 (1H, d), 7.57 (1H, t), 7.34 (m+CHCl$_3$), 7.20 (1H, s), 7.14 (1H, t), 7.05 (1H, t), 6.94 (1H, d), 6.80 (1H, d), 6.55 (2H, m sym.), 4.03-3.73 (2H, m), 3.69 (3H, s), 3.1 (s br.), 2.4 (s br.), 1.13 (3H, t).

Example 9

5-Cyano-3-(2-ethoxyphenyl)-1-(2-methoxy-4-methyl-benzenesulphonyl)-3-(4-pyridin-4-yl-piperazin-1-yl)-2,3-dihydro-1 H-indol-2-one

ESI-MS: [M+H$^+$]=624.20;

Example 10

5-Cyano-1-(2,4-dimethoxy-benzenesulphonyl)-3-(2-ethoxyphenyl)-3-(4-pyridin-4-yl-piperazin-1-yl)-2,3-dihydro-1H-indol-2-one ESI-MS: [M+H$^+$]=640.3;
$^1$H-NMR (400 MHz, CDCl$_3$) δ (ppm): 8.21 (2H, s br.), 8.14 (1H, d), 8.08 (1H, d), 7.82 (1H, d), 7.62 (1H, d), 7.31-7.22

(m+CHCl₃), 7.17 (1H, s), 7.04 (1H, t), 6.81 (1H, d), 6.58 (3H, m), 6.40 (1H, s), 4.03-3.72 (5H, m), 3.64 (3H, s), 3.2 (s br.), 2.5 (s br.), 1.14 (3H, t).

Example 11

5-Chloro-1-(2-fluoro-benzenesulphonyl)-3-(2-methoxyphenyl)-3-(4-pyridin-4-yl-piperazin-1-yl)-1,3-dihydro-indol-2-one ESI-MS: 593.15;
¹H-NMR (400 MHz, CDCl₃) δ (ppm): 8.26 (2H, d), 8.23 (1H, t), 7.91 (1H, d), 7.77 (1H, d), 7.66 (1H, q), 7.43-7.25 (m+CHCl₃), 7.20 (1H, t), 7.08 (1H, t), 6.91 (1H, s), 6.81 (1H, d), 6.74 (2H, d), 3.8 (s br.), 3.41 (3H, s), 3.3 (s br.), 2.72-2.60 (2H, m).

Example 12

5-Chloro-1-(3,4-dimethoxy-benzenesulphonyl)-3-(2-methoxyphenyl)-3-(4-pyridin-4-yl-piperazin-1-yl)-1,3-dihydro-indol-2-one ESI-MS: 635.25;
¹H-NMR (400 MHz, CDCl₃) δ (ppm): 8.29 (2H, d), 7.86 (1H, d), 7.79 (2H, d), 7.70 (1H, s), 7.30 (2H, t), 7.08 (1H, t), 6.96 (1H, d), 6.87 (1H, s), 6.76 (3H, d), 3.90 (6H, s), 3.10 (3H, s), 2.4 (s br.).

Example 13

5-Cyano-3-(2-ethoxyphenyl)-1-(2-fluoro-benzenesulphonyl)-3-(4-pyridin-4-yl-piperazin-1-yl)-2,3-dihydro-1H-indol-2-one

ESI-MS: 598.20;

Example 14

5-Cyano-1-benzenesulphonyl-3-(2-ethoxyphenyl)-3-(4-pyridin-4-yl-piperazin-1-yl)-2,3-dihydro-1H-indol-2-one

ESI-MS: [M+H⁺]=580.25;

¹H-NMR (400 MHz, DMSO) δ (ppm): 8.27 (2H, d), 8.13 (2H, d), 8.05 (1H, d), 7.96 (1H, d), 7.87 (1H, d), 7.70 (1H, t), 7.63 (2H, t), 7.40-7.27 (2H, m), 7.12 (1H, t), 7.04 (2H, d), 6.93 (1H, d), 3.96 (2H, q), 2.35-2.16 (2H, m), 0.71 (3H, t).

Example 15

5-Cyano-3-(2-ethoxyphenyl)-1-(4-fluoro-benzenesulphonyl)-3-(4-pyridin-4-yl-piperazin-1-yl)-2,3-dihydro-1H-indol-2-one

ESI-MS: [M+H+] =598.25;

Example 16

1-Benzenesulphonyl-5-chloro-3-(2-methoxyphenyl)-3-(4-pyridin-4-yl-piperazin-1-yl)-1,3-dihydro-indol-2-one ESI-MS: 578.15; 577.15; [M+H⁺]=576.15; 575.15;
¹H-NMR (400 MHz, DMSO) δ (ppm): 8.26 (2H, m sym.), 8.15 (2H, d), 7.88 (2H, t), 7.79 (1H, t), 7.71 (2H, t), 7.53 (1H, d), 7.34 (1H, t), 7.14 (1H, t), 7.09 (2H, m sym.), 6.91-6.84 (2H, m), 4.33-3.93 (m), 2.89 (3H, s), 2.4 (m).

Example 17

5-Chloro-1-(4-fluoro-benzenesulphonyl)-3-(2-methoxyphenyl)-3-(4-pyridin-4-yl-piperazin-1-yl)-1,3-dihydro-indol-2-one ESI-MS: 593.10;
¹H-NMR (400 MHz, DMSO) δ (ppm): 8.26 (2H, m sym.), 8.16 (2H, m sym.), 7.93-7.83 (2H, m), 7.58 (2H, t), 7.50 (1H, d), 7.33 (1H, t), 7.13 (1H, t), 6.92 (1H, d), 6.87 (1H, s), 6.71 (2H, m sym.), 3.03 (3H, t), 2.45-2.29 (m).

Example 18

5-Chloro-1-(4-chloro-benzenesulphonyl)-3-(2-methoxyphenyl)-3-(4-pyridin-4-yl-piperazin-1-yl)-1,3-dihydro-indol-2-one ESI-MS: 611.05; 609.05;
¹H-NMR (400 MHz, DMSO) δ (ppm): 8.25-8.12 (4H, m), 7.87 (2H, t), 7.80 (2H, d), 7.51 (1H, d), 7.33 (1H, t), 7.13 (1H, t), 6.92 (1H, d), 6.88 (1H, s), 6.73 (2H, m sym.), 3.04 (3H, s), 2.45-2.30 (m).

Example 19

5-Chloro-1-(2,4-dimethoxy-benzenesulphonyl)-3-(2-methoxyphenyl)-3-(5-pyridin-4-yl-hexahydro-pyrrolo[3,4-c]pyrrol-2-yl)-1,3-dihydro-indol-2-one Example 20

5-Chloro-1-(4-methoxy-benzenesulphonyl)-3-(2-methoxyphenyl)-3-(4-pyridin-4-yl-piperazin-1-yl)-1,3-dihydro-indol-2-one ESI-MS: 608.15; 607.15; [M+H⁺]=606.15; 605.15;
¹H-NMR (400 MHz, CDC₃) δ (ppm): 8.27 (2H, d), 8.11 (2H, d), 7.90 (1H, d), 7.78 (1H, d), 7.35-7.22 (2H, m+CHCl₃), 7.08 (1H, t), 7.01 (2H, d), 6.87 (1H, s), 6.76 (1H, s), 6.73 (2H, d), 3.84 (3H, s), 3.14 (3H, s).

Example 21

5-Chloro-1-(2,4-dimethoxy-benzenesulphonyl)-3-(2-methoxyphenyl)-3-((1R,5S)-3-pyridin-4-yl-3,6-diaza-bicyclo[3.2.0]hept-6-yl)-1,3-dihydro-indol-2-one (1494-101) ESI-MS: [M-ᵗBu+H⁺]=277.15; [M-Boc+H⁺]=233.15;

Example 22

5-Chloro-1-(2,4-dimethoxy-benzenesulphonyl)-3-(2-methoxyphenyl)-3-((1R,5S)-6-pyridin-4-yl-3,6-diaza-bicyclo[3.2.0]hept-3-yl)-1,3-dihydro-indol-2-one Example 23

1-(2,4-Dimethoxy-benzenesulphonyl)-3-(2-methoxyphenyl)-6-methyl-3-(4-pyridin-4-yl-piperazin-1-yl)-1,3-dihydro-indol-2-one ESI-MS: [M+H⁺]=615.35;
¹H-NMR (500 MHz, CDCl₃) δ (ppm): 8.21 (3H, m), 7.86-7.76 (2H, m), 7.05 (1H, t), 6.89 (1H, d), 6.81 (2H, t), 6.71 (2H, d), 6.60 (1H, d), 6.45 (1H, s), 3.86 (3H, s), 3.70 (3H, s), 3.39 (3H, s), 2.67 (s br.), 2.41 (3H, s).

Example 24

5-Chloro-3-(2-chloro-phenyl)-1-(2,4-dimethoxy-benzenesulphonyl)-3-(4-pyridin-4-yl-piperazin-1-yl)-1,3-dihydro-indol-2-one ESI-MS: 639.3; 119.2; 101.2;
$^1$H-NMR (500 MHz, CDCl$_3$) δ (ppm): 8.16 (2H, t), 8.10 (1H, d), 7.99 (2H, d), 7.40 (3H, t), 7.20 (1H, d), 6.80 (1H, s), 6.76 (2H, d), 6.62 (1H, d), 6.42 (1H, m), 3.9 [5H, m incl. 3.89 (3H, s)], 3.64 (3H, s), 3.45-3.14 (3H, m), 2.80-2.59 (3H, m).

Example 25

5-Chloro-1-(2,4-dimethoxy-benzenesulphonyl)-3-(5-dimethylaminomethyl-2-methoxyphenyl)-3-(4-pyridin-4-yl-piperazin-1-yl)-1,3-dihydro-indol-2-one

ESI-MS: 695.25; 694.25; [M+H$^+$]=693.25, 692.25; 347.40; 346.65;

Example 26

5-Cyano-1-(2,4-dimethoxy-benzenesulphonyl)-3-(2-methoxyphenyl)-3-(4-pyridin-4-yl-piperazin-1-yl)-2,3-dihydro-1H-indol-2-one ESI-MS: 628.15; 627.25; [M+H$^+$]=626.20;
$^1$H-NMR (400 MHz, CDCl$_3$) δ (ppm): 8.21 (2H, d), 8.14 (1H, d), 8.09 (1H, d), 7.83 (1H, d), 7.63 (1H, d), 7.30 (1H, t), 7.22 (1H, s), 7.09 (1H, t), 6.82 (1H, d), 6.61 (3H, m), 6.44 (1H, s), 3.85 (3H, s), 3.68 (3H, s), 3.48 (3H, s), 3.2 (m br.), 2.6 (m br.), 2.1 (m br.).

Example 27

5-Chloro-1-(2,4-dimethoxy-benzenesulphonyl)-3-(2-methoxyphenyl)-3-((1R,4R)-5-pyridin-4-yl-2,5-diaza-bicyclo[2.2.1]hept-2-yl)-1,3-dihydro-indol-2-one

ESI-MS: 650.15; 649.15; [M+H$^+$]=648.15; 647.15;

Example 28

1-(2,4-Dimethoxy-benzenesulphonyl)-3-(2,5-dimethoxyphenyl)-5-methoxy-3-(4-pyridin-4-yl-piperazin-1-yl)-1,3-dihydro-indol-2-one

ESI-MS: [M+H$^+$]=661.55;

Example 29

5-Chloro-1-(2,4-dimethoxy-benzenesulphonyl)-3-(3,4-dimethoxyphenyl)-3-(4-pyridin-4-yl-piperazin-1-yl)-1,3-dihydro-indol-2-one, trifluoroacetic acid salt ESI-MS: 667.15, [M+H$^+$]=666.15, 665.15;
$^1$H-NMR (400 MHz, DMSO) δ (ppm): 13.33 (1H, s br.), 8.24 (2H, d), 7.93 (1H, d), 7.81 (1H, d), 7.55 (1H, d), 7.50 (1H, s), 7.14-7.05 (3H, m), 6.90 (1H, d), 6.76 (1H, d), 6.69 (1H, s), 6.54 (1H, d), 3.87 (3H, s), 3.72 (6H, d), 3.64 (4H, s br.), 3.48 (3H, s), 2.42-2.29 (2H, m br.).

Example 30

5-Chloro-1-(2,4-dimethoxy-benzenesulphonyl)-3-(2,4-dimethoxyphenyl)-3-(4-pyridin-4-yl-piperazin-1-yl)-1,3-dihydro-indol-2-one, HCl salt ESI-MS: 667.15, [M+H$^+$]=666.20, 665.15;
$^1$H-NMR (400 MHz, DMSO) δ (ppm): 13.41 (1H, s br.), 8.22 (2H, d), 7.91 (1H, d), 7.80 (1H, d), 7.76 (1H, d), 7.49 (1H, d), 7.09 (2H, d), 6.90 (1H, s), 6.73-6.66 (3H, m), 6.52 (1H, s), 3.81 (3H, s), 3.76 (3H, s), 3.67 (3H, s), 3.35 (3H, s), 2.40-2.27 (2H, m br.).

Example 31

5-Chloro-1-(2,4-dimethoxy-benzenesulphonyl)-3-(2,3-dimethoxyphenyl)-3-(4-pyridin-4-yl-piperazin-1-yl)-1,3-dihydro-indol-2-one, HCl salt ESI-MS: 667.15, [M+H$^+$]=666.15, 665.15;
$^1$H-NMR (400 MHz, DMSO) δ (ppm): 13.39 (1H, s br.), 8.24 (2H, d), 7.91 (1H, d), 7.83 (1H, d), 7.53 (1H, d), 7.48 (1H, d), 7.21 (1H, t), 7.13-7.03 (3H, m), 6.88 (1H, s), 6.73-6.65 (2H, m), 3.80 (3H, s), 3.74 (3H, s), 3.64 (3H, s), 3.23 (3H, s), 2.43-2.28 (2H, m br.).

Example 32

5-Chloro-1-(2,4-dimethoxy-benzenesulphonyl)-3-(2-methoxymethylphenyl)-3-(4-pyridin-4-yl-piperazin-1-yl)-1,3-dihydro-indol-2-one

ESI-MS: 649.25;

Example 33

5-Cyano-1-(2,4-dimethoxy-benzenesulphonyl)-3-(2-ethoxyphenyl)-3-[4-(2-ethoxy-pyridin-4-yl)-piperazin-1-yl]-2,3-dihydro-1H-indol-2-one ESI-MS: [M+H$^+$]=684.25;
$^1$H-NMR (400 MHz, CDCl$_3$) δ (ppm): 8.16 (1H, d), 8.07 (1H, d), 7.84 (2H, m), 7.64 (1H, d), 7.28 (m+CHCl$_3$), 7.18 (1H, s), 7.05 (1H, t), 6.81 (1H, d), 6.58 (1H, d), 6.40 (1H, s), 6.25 (1H, m), 5.93 (1H, s), 4.32 (2H, q), 3.97 (1H, quint.), 3.8 [4H, m incl. 3.83 (3H, s)], 3.64 (3H, s), 2.4 (m br.), 1.36 (3H, t), 1.16 (3H, t).

Example 34

5-Cyano-3-[4-(2-chloro-pyridin-4-yl)-piperazin-1-yl]-1-(2,4-dimethoxy-benzenesulphonyl)-3-(2-ethoxyphenyl)-2,3-dihydro-1H-indol-2-one ESI-MS: 674.05;
$^1$H-NMR (400 MHz, CDCl$_3$) δ (ppm): 8.15 (1H, d), 8.09 (1H, d), 8.00 (1H, d), 7.82 (1H, d), 7.64 (1H, d), 7.34-7.21 (m+CHCl$_3$), 7.18 (1H, s), 7.05 (1H, t), 6.81 (1H, d), 6.60 (1H, d), 6.53 (1H, s), 6.46 (1H, m), 6.40 (1H, s), 4.03-3.90 (1H, m), 3.90-3.75[4H, m incl. 3.83 (3H, s)], 3.65 (3H, s), 3.1 (m br.), 2.4 (m br.), 1.14 (3H, t).

Example 35

5-Cyano-1-(2,4-dimethoxy-benzenesulphonyl)-3-(2-ethoxyphenyl)-3-[4-(2-methyl-pyridin-4-yl)-piperazin-1-yl]-2,3-dihydro-1H-indol-2-one

ESI-MS: 656.35, 655.25, [M+H⁺]=654.25;

Example 36

5-Cyano-1-(2-dimethylamino-benzenesulphonyl)-3-(2-ethoxyphenyl)-3-(4-pyridin-4-yl-piperazin-1-yl)-2,3-dihydro-1H-indol-2-one (A-943559.0, 1544-83)

ESI-MS: [M+H⁺]=623.25, 312.15;

Example 37

5-Cyano-3-(2-ethoxyphenyl)-3-(4-pyridin-4-yl-[1.4]diazepan-1-yl)-2,3-dihydro-1H-indol-2-one

ESI-MS: [M+H⁺]=454.45;

Example 38

5-Cyano-3-(2-ethoxyphenyl)-3-(4-pyridin-4-yl-piperazin-1-yl)-2,3-dihydro-1H-indol-2-one ESI-MS: [M+H⁺]=440.15;
¹H-NMR (400 MHz, DMSO) δ (ppm): 10.87 (1H, s), 8.13 (2H, d), 7.93 (1H, d), 7.67 (1H, d), 7.28 (1H, t), 7.15-7.04 (2H, m), 6.98 (1H, d), 6.92 (1H, d), 6.74 (2H, m), 3.76 (2H, m), 3.19 (1H, t), 2.77 (1H, t), 2.55 (m br.), 1.05 (3H, t).

Example 39

5-Cyano-1-(2,4-dimethoxy-benzenesulphonyl)-3-(2-ethoxyphenyl)-3-[4-(3-fluoro-pyridin-4-yl)-piperazin-1-yl]-2,3-dihydro-1H-indol-2-one ESI-MS: [M+H⁺]=658.20;
¹H-NMR (400 MHz, CDCl₃) δ (ppm): 8.23-8.02 (4H, m), 7.83 (1H, d), 7.62 (1H, d), 7.33-7.20 (m+CHCl₃), 7.16 (1H, s), 7.04 (1H, t), 6.80 (1H, d), 6.60 (2H, t), 6.41 (1H, s), 3.96 (1H, quint.), 3.90-3.75 (5H, m), 3.64 (3H, s), 2.42 (1H, s br.), 1.18 (3H, t).

Example 40

5-Cyano-1-(2,4-dimethoxy-benzenesulphonyl)-3-(2-ethoxyphenyl)-3-[4-(2-fluoro-pyridin-4-yl)-piperazin-1-yl]-2,3-dihydro-1H-indol-2-one

ESI-MS: [M+H⁺]=658.15;

Example 41

5-Cyano-3-(2-ethoxyphenyl)-1-(naphthalene-1-sulphonyl)-3-(4-pyridin-4-yl-piperazin-1-yl)-2,3-dihydro-1H-indol-2-one ESI-MS: [M+H⁺]=630.15;
¹H-NMR (400 MHz, CDCl₃) δ (ppm): 8.66 (1H, d), 8.58 (1H, d), 8.30-8.19 (3H, m), 8.06 (1H, d), 7.87 (1H, d), 7.70 (2H, t), 7.60 (1H, t), 7.52 (2H, m sym.), 7.34-7.20 (1H, m), 7.12 (1H, s), 7.01 (1H, t), 6.77 (1H, d), 6.33 (2H, d), 3.88 (1H, quint.), 3.71 (1H, quint.), 3.47-2.46 (m br. incl. 2.82 (1H, t)), 2.11-1.77 (m br.), 1.16 (3H, t).

Example 42

5-Cyano-3-(2-ethoxyphenyl)-1-(2-nitro-benzenesulphonyl)-3-(4-pyridin-4-yl-piperazin-1-yl)-2,3-dihydro-1H-indol-2-one

ESI-MS: [M+H⁺]=625.15;

Example 43

5-Cyano-1-(2-amino-benzenesulphonyl)-3-(2-ethoxyphenyl)-3-(4-pyridin-4-yl-piperazin-1-yl)-2,3-dihydro-1H-indol-2-one

ESI-MS: [M+H⁺]=595.25;

Example 44

5-Cyano-1-(4-dimethylamino-benzenesulphonyl)-3-(2-ethoxyphenyl)-2-oxo-3-(4-pyridin-4-yl-piperazin-1-yl)-2,3-dihydro-1H-indol-2-one ESI-MS: [M+Na⁺]=645.10, 624.25, [M+H⁺]=623.15;

Example 45

5-Cyano-3-(2-ethoxyphenyl)-1-(3-nitro-benzenesulphonyl)-3-(4-pyridin-4-yl-piperazin-1-yl)-2,3-dihydro-1H-indol-2-one ESI-MS: [M+H⁺]=625.25;
¹H-NMR (400 MHz, CDCl₃) δ (ppm): 8.92 (1H, s), 8.54 (1H, d), 8.44 (1H, d), 8.27 (2H, d), 8.09 (1H, d), 7.82 (1H, d), 7.74 (1H, t), 7.70 (1H, d), 7.30 (1H, t), 7.17 (1H, s), 7.08 (1H, t), 6.80 (1H, d), 6.50 (2H, d), 3.83 (1H, quint.), 3.72 (1H, quint.), 3.54-2.65 (4H, m br.), 2.35 (2H, s br.), 1.66 (2H, s br.), 1.00 (3H, t).

Example 46

N-{4-[5-Cyano-3-(2-ethoxyphenyl)-2-oxo-3-(4-pyridin-4-yl-piperazin-1-yl)-2,3-dihydro-indole-1-sulphonyl]-phenyl}-acetamide ESI-MS: [M+H⁺]=637.25;
¹H-NMR (400 MHz, CDCl₃) δ (ppm): 8.21 (2H, d), 8.09 (1H, d), 8.03 (2H, d), 7.95 (1H, s), 7.80 (1H, d), 7.63 (3H, t), 7.29 (1H, t), 7.14 (1H, s), 7.05 (1H, t), 6.79 (1H, d), 6.48 (2H, d), 3.85 (1H, quint.), 3.74 (1H, quint.), 3.70-2.28 (m br.), 2.15 (3H, s), 1.40 (3H, t).

Example 47

1-(2,4-Dimethoxy-benzenesulphonyl)-3-(2-ethoxyphenyl)-5-furan-2-yl-3-(4-pyridin-4-yl-piperazin-1-yl)-1,3-dihydro-indol-2-one ESI-MS: [M+H⁺]=681.35;
¹H-NMR (500 MHz, DMSO) δ (ppm): 8.13 (2H, d), 7.94 (2H, t), 7.88 (1H, d), 7.76 (1H, d), 7.67 (1H, s), 7.29 (1H, t), 7.17-7.10 (2H, m), 6.92 (1H, d), 6.84 (1H, s), 6.70 (4H, s), 6.53 (1H, s), 3.85 (1H, quint.), 3.80 (3H, s), 3.72 (1H, quint.), 3.64 (3H, s), 3.10-2.62 (3H, m br.), 2.32 (2H, s br.), 1.68 (1H, s br.), 1.05 (3H, t).

Example 48

5-Cyano-1-(3-amino-benzenesulphonyl)-3-(2-ethoxyphenyl)-3-(4-pyridin-4-yl-piperazin-1-yl)-2,3-dihydro-1H-indol-2-one ESI-MS: [M+H⁺]=595.25;
¹H-NMR (400 MHz, CDCl₃) δ (ppm): 8.26 (2H, d), 8.06 (1H, d), 7.83 (1H, d), 7.64 (1H, d), 7.38 (2H, s), 7.33-7.19 (m+CHCl₃), 7.14 (1H, s), 7.06 (1H, t), 6.79 (2H, t), 6.52 (2H, d), 3.88 (2H, s), 3.77 (1H, quint.), 3.70 (1H, quint.), 3.46-2.08 (m br.), 1.68 (s br.), 1.06 (3H, t).

Example 49

3-(2-Ethoxyphenyl)-5-furan-2-yl-3-(4-pyridin-4-yl-piperazin-1-yl)-1,3-dihydro-indol-2-one

ESI-MS: [M+H⁺]=481.15;

Example 50

5-Cyano-1-(2,4-dimethoxy-benzenesulphonyl)-3-(2-ethoxy-5-methoxyphenyl)-3-[4-(2-methyl-pyridin-4-yl)-piperazin-1-yl]-2,3-dihydro-1H-indol-2-one ESI-MS: [M+H⁺]=684.15;
¹H-NMR (500 MHz, CDCl₃) δ (ppm): 8.13 (2H, d), 8.07 (1H, d), 7.63 (1H, d), 7.44 (1H, s), 7.20 (1H, s), 6.80 (1H, d), 6.73 (1H, d), 6.59 (1H, d), 6.47-6.36 (3H, m), 3.88 (1H, quint.), 3.82 (3H, s), 3.80 (3H, s), 3.72 (1H, quint.), 3.65 (3H, s), 2.44 (3H, s), 1.12 (3H, t).

Example 52

5-Cyano-1-(2,4-dimethoxy-benzenesulphonyl)-3-(2-ethoxy-5-methoxyphenyl)-3-((1S,4S)-5-pyridin-4-yl-2,5-diaza-bicyclo[2.2.1]hept-2-yl)-2,3-dihydro-1H-indol-2-one

ESI-MS: [M+H⁺]=682.15;

Example 53

5-Cyano-1-(2,4-dimethoxy-benzenesulphonyl)-3-(2-isopropoxy-5-methoxyphenyl)-3-(4-pyridin-4-yl-piperazin-1-yl)-2,3-dihydro-1H-indol-2-one ESI-MS: [M+H⁺]=684.25;
¹H-NMR (500 MHz, CDCl₃) δ (ppm): 8.25 (2H, d), 8.14 (1H, d), 8.08 (1H, d), 7.63 (1H, d), 7.44 (1H, s), 7.17 (1H, s), 6.81 (1H, d), 6.73 (1H, d), 6.55 (1H, d), 6.52 (2H, d), 6.36 (1H, s), 4.37 (1H, quint.), 3.80 (3H, s), 3.78 (3H, s), 3.61 (3H, s), 3.45-2.74 (m br.), 2.35 (2H, s br.), 1.77 (1H, s br.), 1.25 (3H, d), 0.87 (3H, d).

Example 54

5-Cyano-1-(2-chloro-4-cyano-benzenesulphonyl)-3-(2-ethoxyphenyl)-3-(4-pyridin-4-yl-piperazin-1-yl)-2,3-dihydro-1H-indol-2-one ESI-MS: 642.3; 641.3; [M⁺]=639.2;
¹H-NMR (500 MHz, DMSO) δ (ppm): 8.47 (1H, d), 8.36 (1H, s), 8.25 (2H, d), 8.13 (1H, d), 8.03 (1H, d), 7.97 (1H, d), 7.90 (1H, d), 7.40 (1H, s), 7.34 (1H, t), 7.12 (1H, t), 7.08 (2H, d), 6.98 (1H, d), 4.04 (s br.), 4.90 (1H, quint.), 3.78 (1H, quint.), 3.00 (s br.), 2.14 (1H, s br.), 1.75 (1H, s br.), 0.94 (3H, t).

Example 55

5-Cyano-1-(2,4-dimethoxy-benzenesulphonyl)-3-(2-ethoxy-5-methoxyphenyl)-3-(4-pyridin-4-yl-piperazin-1-yl)-2,3-dihydro-1H-indol-2-one ESI-MS: [M+H⁺]=670.50;
¹H-NMR (500 MHz, DMSO) δ (ppm): 8.12 (2H, d), 8.01-7.85 (3H, m), 7.44 (2H, s), 6.88 (2H, m), 6.71 (4H, s), 3.84-3.59 [m incl. 3.80 (3H, s), 3.77 (3H, s), 3.63 (3H, s)], 3.10-2.72 (3H, m br.), 2.25 (2H, d Br.), 1.65 (1H, s br.), 0.98 (3H, t).

Example 56

5-Cyano-1-(2,4-dimethoxy-benzenesulphonyl)-3-(2-ethoxyphenyl)-3-(4-pyridin-4-yl-[1.4]diazepan-1-yl)-2,3-dihydro-1H-indol-2-one

ESI-MS: [M+H⁺]=674.15;

Example 57

5-Cyano-1-(2,4-dimethoxy-benzenesulphonyl)-3-(2-ethoxy-4-fluorophenyl)-3-(4-pyridin-4-yl-piperazin-1-yl)-2,3-dihydro-1H-indol-2-one ESI-MS: [M+H⁺]=658.35;
¹H-NMR (500 MHz, CDCl₃) δ (ppm): 8.24 (2H, d), 8.13 (1H, d), 8.08 (1H, d), 7.70 (1H, t), 7.65 (1H, d), 7.16 (1H, s), 6.76 (1H, t), 6.59 (1H, d), 6.55-6.47 (3H, m), 6.38 (1H, s), 3.92 (1H, quint.), 3.82 (3H, s), 3.78 (1H, quint.), 3.64 (3H, s), 2.41 (2H, s br.), 2.08 (2H, s br.), 1.16 (3H, t).

Example 58

5-Cyano-1-(2,4-dimethoxy-benzenesulphonyl)-3-(2-ethoxy-5-methoxyphenyl)-3-(5-pyridin-4-yl-hexahydro-pyrrolo[3,4-c]pyrrol-2-yl)-2,3-dihydro-1H-indol-2-one

ESI-MS: [M+H⁺]=696.25;

Example 59

5-Cyano-1-(2,4-dimethoxy-benzenesulphonyl)-3-(2,5-dimethoxyphenyl)-3-(4-pyridin-4-yl-piperazin-1-yl)-2,3-dihydro-1H-indol-2-one ESI-MS: [M+H⁺]=656.25;
¹H-NMR (500 MHz, CDCl₃) δ (ppm): 8.25 (2H, d), 8.16 (1H, d), 8.10 (1H, d), 7.65 (1H, d), 7.44 (1H, s), 7.25 (1H, d), 6.82 (1H, m), 6.76 (1H, d), 6.62 (1H, d), 6.55 (2H, d), 6.44 (1H, s), 3.86 (3H, s), 3.82 (3H, s), 3.67 (3H, s), 3.52 (1H, s br.), 3.42 (3H, s), 3.23 (1H, s br.), 2.98 (1H, s br.), 2.88 (1H, s br.), 2.65 (1H, s br.), 2.40 (1H, s br.), 2.08 (3H, s br.).

Example 60

5-Cyano-1-(2,4-dimethoxy-benzenesulphonyl)-3-(2-ethoxy-5-methoxyphenyl)-3-(4-pyridin-4-yl-[1.4]diazepan-1-yl)-2,3-dihydro-1H-indol-2-one

ESI-MS: [M+H$^+$]=684.20;

Example 61

5-Cyano-1-(4-cyano-benzenesulphonyl)-3-(2-ethoxy-5-methoxyphenyl)-3-(4-pyridin-4-yl-piperazin-1-yl)-2,3-dihydro-1H-indol-2-one ESI-MS: [M+H$^+$]=635.20;
$^1$H-NMR (500 MHz, CDCl$_3$) δ (ppm): 8.31 (2H, d), 8.25 (2H, d), 8.02 (1H, d), 7.87 (2H, d), 7.67 (1H, d), 7.42 (1H, s), 6.82 (1H, d), 6.71 (1H, d), 6.57 (2H, d), 3.72 (3H, s), 3.67 (1H, quint.), 3.55 (1H, quint.), 3.44 (1H, s br.), 3.26 (1H, s br.), 3.00 (1H, s br.), 2.84 (2H, m br.), 2.54 (1H, s br.), 2.27 (1H, s br.), 1.75 (1H, s b r.), 0.87 (3H, t).

Example 62

5-Cyano-3-(2-ethoxy-5-methoxyphenyl)-1-(4-methoxy-benzenesulphonyl)-3-(4-pyridin-4-yl-piperazin-1-yl)-2,3-dihydro-1H-indol-2-one ESI-MS: [M+H$^+$]=640.25;
$^1$H-NMR (500 MHz, CDCl$_3$) δ (ppm): 8.24 (2H, m), 8.07 (3H, d), 7.64 (1H, d), 7.42 (1H, s), 7.18 (1H, s), 6.97 (2H, d), 6.80 (1H, d), 6.70 (1H, d), 6.53 (2H, d), 3.82 (3H, s), 3.75 (3H, s), 3.69 (1H, quint.), 3.60 (1H, quint.), 3.36 (1H, s br.), 3.24 (1H, s br.), 2.97 (1H, s br.), 2.77 (1H, s br.), 2.53 (1H, s br.), 2.18 (1H, s br.), 1.53 (1H, s br.), 0.99 (3H, t).

Example 63

5-Cyano-3-(2,5-dimethoxyphenyl)-1-(4-methoxy-benzenesulphonyl)-3-(4-pyridin-4-yl-piperazin-1-yl)-2,3-dihydro-1H-indol-2-one ESI-MS: [M+H$^+$]=626.15;
$^1$H-NMR (500 MHz, CDCl$_3$) δ (ppm): 8.25 (2H, m), 8.11 (2H, d), 8.05 (1H, d), 7.63 (1H, d), 7.41 (1H, s), 7.20 (1H, s), 7.01 (2H, d), 6.81 (1H, d), 6.70 (1H, d), 6.55 (2H, d), 3.84 (3H, s), 3.81 (3H, s), 3.17 (3H, s).

Example 64

5-Cyano-3-(5-fluoro-2-methoxyphenyl)-3-(4-pyridin-4-yl-piperazin-1-yl)-2,3-dihydro-1H-indol-2-one

ESI-MS: [M+H$^+$]=444.15;

Example 65

(±)-5-Cyano-1-(2,4-dimethoxy-benzenesulphonyl)-3-(5-fluoro-2-methoxyphenyl)-3-(4-pyridin-4-yl-piperazin-1-yl)-2,3-dihydro-1H-indol-2-one ESI-MS: [M+H$^+$]=644.15;
$^1$H-NMR (500 MHz, CDCl$_3$) δ (ppm): 8.23 (2H, m), 8.14 (2H, d), 8.10 (2H, d), 7.64 (1H, d), 7.60 (1H, d), 7.22 (1H, s), 7.00 (1H, m), 6.77 (1H, m), 6.62 (1H, d), 6.55 (2H, d), 6.43 (1H, s), 3.83 (3H, s), 3.68 (3H, s), 3.47 (3H, s), 3.25-2.20 (8H, m br.).

Example 66

(±)-5-Cyano-1-(3-dimethylaminomethyl-benzenesulphonyl)-3-(2-ethoxyphenyl)-3-(4-pyridin-4-yl-piperazin-1-yl)-2,3-dihydro-1H-indol-2-one

ESI-MS: [M+H$^+$]=637.25;

Example 67

(±)-5-Cyano-1-(2,4-dimethoxy-benzenesulphonyl)-3-(2-methoxy-5-methylphenyl)-3-(4-pyridin-4-yl-piperazin-1-yl)-2,3-dihydro-1H-indol-2-onextrifluoroacetic acid

Example 68

(±)-5-Cyano-1-(4-cyano-2-fluoro-benzenesulphonyl)-3-(2-ethoxyphenyl)-3-(4-pyridin-4-yl-piperazin-1-yl)-2,3-dihydro-1H-indol-2-one

ESI-MS: [M+H$^+$]=623.25;

Example 69

(±)-5-Cyano-3-[4-(3,5-dichloro-pyridin-4-yl)-piperazin-1-yl]-1-(2,4-dimethoxy-benzenesulphonyl)-3-(2-ethoxyphenyl)-2,3-dihydro-1H-indol-2-one ESI-MS: 710.25, 708.25;
$^1$H-NMR (400 MHz, DMSO) δ (ppm): 8.40 (2H, s), 7.98 (2H, d), 7.90 (2H, d), 7.37-7.28 (2H, m), 7.11 (1H, t), 6.95 (1H, d), 6.78 (1H, d), 6.67 (1H, s), 3.97-3.83 [4H, m incl. 3.86 (3H, s)], 3.77 (1H, quint), 3.62-3.43 [4H, m incl. 3.57 (3H, s)], 3.43-2.86 (m+H$_2$O), 2.39-2.13 (2H, m), 1.77 (1H, s br.), 1.10 (3H, t).

Example 70

(±)-5-Cyano-1-(2,4-dimethoxy-benzenesulphonyl)-3-(2-ethoxy-5-methoxyphenyl)-3-[4-(2-trifluoromethyl-pyridin-4-yl)-piperazin-1-yl]-2,3-dihydro-1H-indol-2-onextrifluoroacetic acid ESI-MS: [M+H$^+$]=738.15;
$^1$H-NMR (500 MHz, CDCl$_3$) δ (ppm): 8.35 (1H, d), 8.12 (1H, d), 8.10 (1H, d), 7.65 (1H, d), 7.42 (1H, s), 7.22 (1H, s), 6.92 (1H, s), 6.82 (1H, d), 6.73 (1H, d), 6.68 (1H, m), 6.57 (1H, d), 6.41 (1H, s), 5.71 (1H, m br.), 3.94-2.87 [17H, m incl. 3.80 (3H, d), 3.71 (1H, quint.), 3.65 (3H, s)], 2.47 (2H, s br.), 1.98 (1H, s br.), 1.09 (3H, t).

Example 71

(±)-5-Cyano-1-(2,4-dimethoxy-benzenesulphonyl)-3-(2-ethoxyphenyl)-3-[4-(2-trifluoromethyl-pyridin-4-yl)-piperazin-1-yl]-2,3-dihydro-1H-indol-2-one×trifluoroacetic acid ESI-MS: [M+H$^+$]=708.15;
$^1$H-NMR (500 MHz, CDCl$_3$) δ (ppm): 8.36 (1H, d), 8.12 (1H, d), 8.09 (1H, d), 7.82 (1H, d), 7.65 (1H, d), 7.29 (1H, t), 7.19 (1H, s), 7.04 (1H, t), 6.93 (1H, s), 6.81 (1H, d), 6.71 (1H, m), 6.58 (1H, d), 6.41 (1H, s), 3.97-2.96 [12H, m br. incl. 3.93 (1H, quint.), 3.80 (4H, m sym.), 3.66 (3H, s)], 2.47 (2H, s br.), 1.13 (3H, t).

Example 72

(±)-5-Cyano-1-(2,4-difluoro-benzenesulphonyl)-3-(2-ethoxyphenyl)-3-(4-pyridin-4-yl-piperazin-1-yl)-2,3-dihydro-1H-indol-2-one trifluoroacetate ESI-MS: [M+H$^+$]=616.15;
$^1$H-NMR (500 MHz, DMSO) δ (ppm): 8.27 (2H, d), 8.22 (1H, m sym.), 7.97 (2H, s), 7.91 (1H, d), 7.61 (1H, t), 7.40-7.30 (3H, m), 7.13 (1H, t), 7.08 (2H, d), 6.96 (1H, d), 4.22-3.91 (2H, m br.), 3.82 (1H, quint.), 3.73 (1H, quint.), 3.57-2.94 (m Br., incl. H$_2$O), 2.52-2.08 (2H, m br.), 1.65 (1H, s br.), 0.94 (3H, t).

Example 73

(±)-5-Cyano-1-(2,4-dichloro-benzenesulphonyl)-3-(2-ethoxyphenyl)-3-(4-pyridin-4-yl-piperazin-1-yl)-2,3-dihydro-1H-indol-2-one×trifluoroacetic acid ESI-MS: 650.05, 648.05;
$^1$H-NMR (500 MHz, DMSO) δ (ppm): 8.34-8.23 (3H, m), 8.02 (1H, d), 7.99-7.88 [3H, m incl. 7.96 (1H, d)], 7.73 (1H, d), 7.38 (1H, s), 7.35 (1H, t), 7.13 (1H, t), 7.10 (2H, d), 6.99 (1H, d), 4.23-3.98 (2H, m br.), 3.91 (1H, quint.), 3.80 (1H, quint.), 3.59-2.90 (3H, m br.), 2.50 (1H, s), 2.13 (1H, s br.), 1.75 (1H, s), 0.95 (3H, t).

Example 74

(±)-5-Cyano-1-(2-chloro-4-trifluoromethyl-benzenesulphonyl)-3-(2-ethoxyphenyl)-3-(4-pyridin-4-yl-piperazin-1-yl)-2,3-dihydro-1H-indol-2-one×trifluoroacetic acid ESI-MS: 682.15;
$^1$H-NMR (500 MHz, DMSO) δ (ppm): 8.53 (1H, d), 8.23 (2H, d), 8.20 (1H, s), 8.04 (2H, t), 7.96 (1H, d), 7.91 (1H, d), 7.41 (1H, s), 7.34 (1H, t), 7.12 (1H, t), 7.08 (2H, d), 6.97 (1H, d), 4.20-2.92 [13H, m br. incl. 3.97 (1H, quint.), 3.79 (1H, quint.)], 2.12 (1H, s br.), 1.73 (1H, s br.), 0.92 (3H, t).

Example 75

(±)-5-Cyano-1-(2-chloro-4-fluoro-benzenesulphonyl)-3-(2-ethoxyphenyl)-3-(4-pyridin-4-yl-piperazin-1-yl)-2,3-dihydro-1H-indol-2-one×trifluoroacetic acid ESI-MS: 632.20;
$^1$H-NMR (500 MHz, DMSO) δ (ppm): 8.38 (1H, m sym.), 8.28 (2H, d), 8.03 (1H, d), 7.96 (1H, d), 7.92 (1H, d), 7.77 (1H, d), 7.52 (1H, t), 7.38 (1H, s), 7.33 (1H, t), 7.16-7.06 (3H, m), 6.96 (1H, d), 4.20-2.90 [12H, m br. incl. 3.90 (1H, quint.), 3.77 (1H, quint.)], 2.14 (1H, s br.), 1.74 (1H, s br.), 0.95 (3H, t).

Example 76

(±)-5-Cyano-1-(2,4-dimethoxy-benzenesulphonyl)-3-(2-ethoxyphenyl)-3-[4-(1-methyl-piperidin-4-yl)-piperazin-1-yl]-2,3-dihydro-1H-indol-2-one ESI-MS: [M+H$^+$]=660.25;
$^1$H-NMR (500 MHz, DMSO) δ (ppm): 7.96 (2H, m sym.), 7.86 (1H, d), 7.78 (1H, d), 7.28 (1H, t), 7.22 (1H, s), 7.06 (1H, t), 6.92 (1H, d), 6.78 (1H, d), 6.73 (1H, s), 3.88 (3H, s), 3.80 (1H, quint.), 3.70 (1H, quint.), 3.60 (3H, s), 2.74 (2H, d Br.), 2.21-2.10 (6H, m), 2.02 (1H, t), 1.83 (2H, t), 1.60 (2H, t), 1.32 (2H, quint.), 0.95 (3H, t).

Example 77

(±)-5-Cyano-1-(4-ethoxy-2-methoxy-benzenesulphonyl)-3-(2-ethoxyphenyl)-3-(4-pyridin-4-yl-piperazin-1-yl)-2,3-dihydro-1H-indol-2-one hydrochloride ESI-MS: [M+H$^+$]=654.30;
$^1$H-NMR (500 MHz, DMSO) δ (ppm): 8.22 (2H, d), 8.01-7.85 (4H, m), 7.35-7.27 (2H, m), 7.18-7.06 (3H, m), 6.95 (1H, d), 6.68-6.61 (2H, m), 4.18-4.00 (3H, m), 3.84 (1H, quint.), 3.74 (1H, m), 3.63 (3H, s), 3.52-2.95 (m+H$_2$O), 2.37-2.13 (2H, m br.), 1.56 (1H, s br.), 1.27 (3H, t), 1.00 (3H, t).

Example 78

(±)-5-Cyano-1-(4-chloro-2-fluoro-benzenesulphonyl)-3-(2-ethoxyphenyl)-3-(4-pyridin-4-yl-piperazin-1-yl)-2,3-dihydro-1H-indol-2-one

ESI-MS: 632.29;

Example 79

(±)-5-Cyano-3-(2-ethoxyphenyl)-1-(4-fluoro-2-methyl-benzenesulphonyl)-3-(4-pyridin-4-yl-piperazin-1-yl)-2,3-dihydro-1H-indol-2-one

ESI-MS: [M+H$^+$]=612.31;

Example 80

(±)-5-Cyano-1-(4-tert-butyl-benzenesulphonyl)-3-(2-ethoxyphenyl)-3-(4-pyridin-4-yl-piperazin-1-yl)-2,3-dihydro-1H-indol-2-one ESI-MS: [M+H$^+$]=636.35;
$^1$H-NMR (500 MHz, CDCl$_3$) δ (ppm): 8.24 (2H, d), 8.08 (3H, m), 7.83 (1H, d), 7.64 (1H, d), 7.56 (2H, d), 7.27 (1H, t), 7.13 (1H, s), 7.05 (1H, t), 6.76 (1H, d), 6.50 (2H, d), 3.67 (2H, m sym.), 3.32-2.16 (5H, m br.), 1.22 (3H, s), 0.98 (3H, t).

Example 81

(±)-5-Cyano-3-(2-ethoxyphenyl)-1-(4-isopropyl-benzenesulphonyl)-3-(4-pyridin-4-yl-piperazin-1-yl)-2,3-dihydro-1H-indol-2-one ESI-MS: [M+H$^+$]=622.31;
$^1$H-NMR (500 MHz, CDCl$_3$) δ (ppm): 8.24 (2H, d), 8.07 (3H, m), 7.81 (1H, d), 7.63 (1H, d), 7.40 (2H, d), 7.27 (1H, t), 7.13 (1H, s), 7.06 (1H, t), 6.76 (1H, d), 6.52 (2H, d), 3.66 (2H, m sym.), 3.55-2.11 [m br. incl. 2.90 (1H, quint)], 1.56 (1H, s br.), 1.14 (6H, t), 0.98 (3H, t).

Example 82

(±)-5-Cyano-3-(2-ethoxyphenyl)-3-(4-pyridin-4-yl-piperazin-1-yl)-1-(4-trifluoromethoxy-benzenesulphonyl)-2,3-dihydro-1H-indol-2-one ESI-MS: [M+H$^+$]=664.35;
$^1$H-NMR (500 MHz, CDCl$_3$) δ (ppm): 8.31-8.20 (4H, m), 8.05 (1H, d), 7.83 (1H, d), 7.67 (1H, d), 7.40 (2H, d), 7.27

(1H, t), 7.16 (1H, s), 7.06 (1H, t), 6.78 (1H, d), 6.54 (1H, d), 3.77-1.60 [10H, m br. incl. 3.70 (1H, quint), 3.65 (1H, quint)], 0.92 (3H, t).

Example 83

(±)-5-Cyano-3-(2-ethoxyphenyl)-3-(4-pyridin-4-yl-piperazin-1-yl)-1-(4-trifluoromethyl-benzenesulphonyl)-2,3-dihydro-1H-indol-2-one

ESI-MS: [M+H$^+$]=648.25;

Example 84

(±)-5-Cyano-1-(4-amino-benzenesulphonyl)-3-(2-ethoxyphenyl)-3-(4-pyridin-4-yl-piperazin-1-yl)-2,3-dihydro-1H-indol-2-one ESI-MS: [M+H$^+$]=595.25;
$^1$H-NMR (500 MHz, DMSO) δ (ppm): 8.15 (2H, s br.), 7.98 (1H, t), 7.85 (2H, m), 7.72 (2H, d), 7.30 (1H, t), 7.24 (1H, s), 7.09 (1H, t), 6.91 (1H, d), 6.70 (2H, s), 6.64 (2H, d), 6.42 (2H, s), 3.90-2.18 [m br.+H$_2$O+DMSO incl. 3.53 (2H, t), 2.30 (2H, s br.), 0.78 (3H, t).

Example 85

(±)-5-Cyano-3-(2-ethoxyphenyl)-3-(4-pyridin-4-yl-piperazin-1-yl)-1-(toluene-4-sulphonyl)-2,3-dihydro-1H-indol-2-one ESI-MS: [M+H$^+$]=594.30;
$^1$H-NMR (500 MHz, CDCl$_3$) δ (ppm): 8.25 (2H, s), 8.08 (1H, d), 8.03 (2H, d), 7.82 (1H, d), 7.63 (1H, d), 7.32 (2H, d), 7.13 (1H, s), 7.05 (1H, t), 6.76 (1H, d), 6.51 (2H, s), 3.83-2.10 [9H, m br. incl. 3.83 (1H, quint), 3.68 (1H, quint)], 1.80-0.74 [6H, m br. incl. 1.01 (3H, t)].

Example 86

(±)-5-Cyano-3-(2-ethoxyphenyl)-1-(4-methane-sulphonyl-benzenesulphonyl)-3-(4-pyridin-4-yl-piperazin-1-yl)-2,3-dihydro-1H-indol-2-one

ESI-MS: [M+H$^+$]=658.30;

Example 87

(±)-5-Cyano-1-(4-difluoromethoxy-benzenesulphonyl)-3-(2-ethoxyphenyl)-3-(4-pyridin-4-yl-piperazin-1-yl)-2,3-dihydro-1H-indol-2-one

ESI-MS: [M+H$^+$]=646.20;

Example 88

(±)-5-Cyano-1-(4-acetyl-benzenesulphonyl)-3-(2-ethoxyphenyl)-3-(4-pyridin-4-yl-piperazin-1-yl)-2,3-dihydro-1H-indol-2-one

ESI-MS: [M+H$^+$]=622.20;

Example 89

(±)-5-Cyano-1-(4-ethoxy-benzenesulphonyl)-3-(2-ethoxyphenyl)-3-(4-pyridin-4-yl-piperazin-1-yl)-2,3-dihydro-1H-indol-2-one

ESI-MS: [M+H$^+$]=624.25;

Example 90

(±)-5-Cyano-3-(2-ethoxyphenyl)-1-(4-ethyl-benzenesulphonyl)-3-(4-pyridin-4-yl-piperazin-1-yl)-2,3-dihydro-1H-indol-2-one

ESI-MS: [M+H$^+$]=608.25;

Example 91

(±)-5-Cyano-3-(2-ethoxyphenyl)-1-(2-methoxy-4-nitro-benzenesulphonyl)-3-(4-pyridin-4-yl-piperazin-1-yl)-2,3-dihydro-1H-indol-2-one $^1$H-NMR (500 MHz, CDCl$_3$) δ (ppm): 8.43 (1H, d), 8.26 (2H, d), 8.08 (1H, d), 8.00 (1H, d), 7.84 (1H, d), 7.80 (1H, s), 7.68 (1H, d), 7.30 (1H, t), 7.22 (1H, s), 7.08 (1H, t), 6.83 (1H, d), 6.54 (2H, d), 3.98 (1H, quint.), 3.89-3.79 (4H, m sym.), 2.44 (1H, s br.), 2.25 (1H, s br.), 1.11 (3H, t).

Example 92

(±)-5-Cyano-1-(2,4-dimethoxy-benzenesulphonyl)-3-(2-ethoxy-5-methoxyphenyl)-3-[4-(2-isopropyl-pyridin-4-yl)-piperazin-1-yl]-2,3-dihydro-1H-indol-2-one ESI-MS: [M+H$^+$]=712.80;
$^1$H-NMR (500 MHz, CDCl$_3$) δ (ppm): 8.20 (1H, d), 8.14 (1H, d), 8.08 (1H, d), 7.63 (1H, d), 7.44 (1H, s), 7.21 (1H, s), 6.81 (1H, d), 6.73 (1H, d), 6.60 (1H, d), 6.48-6.36 (3H, m), 3.87 (1H, quint.), 3.84 (3H, s), 3.82 (3H, s), 3.72 (1H, quint.), 3.65 (3H, s), 3.54-2.84 [5H, m br. incl. 2.93 (2H, m sym.)], 2.44 (2H, s br.), 1.94 (1H, s br.), 1.71 (2H, s br.), 1.25 (6H, d), 1.12 (3H, t).

Example 93

(±)-5-Cyano-1-(2,4-dimethoxy-benzenesulphonyl)-3-(2-ethoxyphenyl)-3-[4-(2-ethyl-pyridin-4-yl)-piperazin-1-yl]-2,3-dihydro-1H-indol-2-one ESI-MS: [M+H$^+$]=668.75;
$^1$H-NMR (500 MHz, CDCl$_3$) δ (ppm): 8.20 (1H, d), 8.15 (1H, d), 8.10 (1H, d), 7.84 (1H, d), 7.65 (1H, d), 7.30 (1H, t), 7.20 (1H, s), 7.06 (1H, t), 6.80 (1H, d), 6.60 (1H, d), 6.49-6.40 (3H, m), 3.95 (1H, quint.), 3.83 (3H, s), 3.80 (1H, quint.), 3.72-3.58 [4H, m incl. 3.64 (3H, s)], 2.51-2.84 (m br.), 2.74 (2H, q), 2.57-2.29 (2H, m br.), 1.92 (1H, s br.), 1.27 (3H, t), 1.15 (3H, t).

Example 94

(±)-5-Cyano-1-(2,4-dimethoxy-benzenesulphonyl)-3-(2-ethoxy-5-methoxyphenyl)-3-[4-(2-ethyl-pyridin-4-yl)-piperazin-1-yl]-2,3-dihydro-1H-indol-2-one

ESI-MS: [M+H$^+$]=698.80;

Example 95

(±)-5-Cyano-1-(2,4-dimethoxy-benzenesulphonyl)-3-(2-ethoxy-5-methoxyphenyl)-3-[4-(2-methyl-pyridin-4-yl)-[1.4]diazepan-1-yl]-2,3-dihydro-1H-indol-2-one

ESI-MS: [M+H$^+$]=698.80;

Example 96

(+)-5-Cyano-1-(2,4-dimethoxy-benzenesulphonyl)-3-(2-ethoxy-5-methoxyphenyl)-3-(4-pyridin-4-yl-piperazin-1-yl)-2,3-dihydro-1H-indol-2-one ESI-MS: [M+H$^+$]=670.25;
$^1$H-NMR (500 MHz, CDCl$_3$) δ (ppm): 8.24 (2H, d), 8.13 (1H, d), 8.08 (1H, d), 7.63 (1H, d), 7.44 (1H, s), 7.21 (1H, s), 6.81 (1H, d), 6.73 (1H, d), 6.58 (1H, d), 6.54 (2H, d), 6.40 (1H, s), 3.87 (1H, quint.), 3.81 (6H, s), 3.72 (1H, quint.), 3.65 (3H, s), 2.43 (2H, s br.), 1.11 (3H, t).
α (20° C., c=1 mg/ml, CHCl$_3$, I=1 dm): +105°;

Example 97

(−)-5-Cyano-1-(2,4-dimethoxy-benzenesulphonyl)-3-(2-ethoxy-5-methoxyphenyl)-3-(4-pyridin-4-yl-piperazin-1-yl)-2,3-dihydro-1H-indol-2-one ESI-MS: [M+H$^+$]=670.25;
$^1$H-NMR (500 MHz, CDCl$_3$) δ (ppm): 8.23 (2H, d), 8.13 (1H, d), 8.07 (1H, d), 7.63 (1H, d), 7.44 (1H, s), 7.21 (1H, s), 6.80 (1H, d), 6.73 (1H, d), 6.58 (1H, d), 6.53 (2H, d), 6.39 (1H, s), 3.87 (1H, quint.), 3.81 (6H, s), 3.71 (1H, quint.), 3.65 (3H, s), 2.42 (2H, s br.), 1.11 (3H, t).
α (20° C., c=1 mg/ml, CHCl$_3$, I=1 dm): −116°;

Example 98

(±)-5-Cyano-1-(4-chloro-naphthalene-1-sulphonyl)-3-(2-ethoxyphenyl)-3-(4-pyridin-4-yl-piperazin-1-yl)-2,3-dihydro-1H-indol-2-one ESI-MS: [M+H$^+$]=664.15;
$^1$H-NMR (500 MHz, CDCl$_3$) δ (ppm): 8.64 (1H, d), 8.59 (1H, d), 8.36 (1H, d), 8.23 (2H, d), 8.20 (1H, d), 7.81-7.54 (5H, m), 7.31-7.22 (m+CHCl$_3$), 7.12 (1H, s), 7.03 (1H, t), 6.77 (1H, d), 6.26 (2H, d), 3.86 (1H, quint.), 3.69 (1H, quint.), 3.16-2.50 (4H, m br.), 2.20-1.82 (2H, m br.), 1.23-0.92 [4H, m incl. 1.12 (3H, t)].

Example 99

(±)-5-Cyano-3-(2-ethoxyphenyl)-1-(4-fluoro-naphthalene-1-sulphonyl)-3-(4-pyridin-4-yl-piperazin-1-yl)-2,3-dihydro-1H-indol-2-one ESI-MS: [M+H$^+$]=648.25;
$^1$H-NMR (500 MHz, CDCl$_3$) δ (ppm): 8.66 (1H, m sym.), 8.57 (1H, m), 8.30-8.10 (4H, m), 7.82-7.68 (2H, m sym.), 7.61 (2H, d), 7.35-7.21 (m+CHCl$_3$), 7.14 (1H, s), 7.03 (1H, t), 6.78 (1H, d), 6.36 (2H, m), 3.87 (1H, quint.), 3.70 (1H, quint.), 3.45 (2H, s br.), 3.12-2.52 (5H, m br.), 2.20-1.68 (5H, m br.), 1.20-0.86 [4H, m incl. 1.12 (3H, t)].

Example 100

(±)-5-Cyano-1-(2,4-dimethoxy-benzenesulphonyl)-3-(2-ethoxy-5-methoxyphenyl)-3-(4-piperidin-4-yl-piperazin-1-yl)-2,3-dihydro-1H-indol-2-one hydrochloride

ESI-MS: [M+H$^+$]=676.25;

Example 101

(±)-5-Cyano-1-(2,4-dimethoxy-benzenesulphonyl)-3-(2-ethoxy-5-methylphenyl)-3-(4-pyridin-4-yl-piperazin-1-yl)-2,3-dihydro-1H-indol-2-one ESI-MS: [M+H$^+$]=654.20;
$^1$H-NMR (500 MHz, CDCl$_3$) δ (ppm): 8.25 (2H, d), 8.14 (1H, d), 8.08 (1H, d), 7.66-7.60 (2H, m), 7.21 (1H, s), 7.07 (1H, d), 6.69 (1H, d), 6.58 (1H, d), 6.55 (2H, d), 6.40 (1H, s), 3.90 (1H, quint.), 3.83 (3H, s), 3.76 (1H, quint.), 3.64 (3H, s), 2.50-2.33 [4H, m incl. 2.36 (3H, s)], 2.01-1.61 [4H, m br. incl. 1.14 (3H, t)].

Example 102

(±)-5-Cyano-1-(2,4-dimethoxy-benzenesulphonyl)-3-(2-ethoxy-5-methoxyphenyl)-3-[4-(1-methyl-piperidin-4-yl)-piperazin-1-yl]-2,3-dihydro-1H-indol-2-one ESI-MS: [M+H$^+$]=690.30;
$^1$H-NMR (500 MHz, CDCl$_3$) δ (ppm): 8.13 (1H, d), 8.04 (1H, d), 7.60 (1H, d), 7.42 (1H, s), 7.16 (1H, s), 6.77 (1H, d), 6.70 (1H, d), 6.62 (1H, d), 6.41 (1H, s), 3.91-3.79 [7H, m incl. 2.33 (3H, s), 2.19 (1H, t), 2.07 (2H, m br.)], 1.77 (2H, t br.), 1.60 (2H, quint br.), 1.08 (3H, t).

Example 103

(±)-5-Cyano-1-(2,4-dimethoxy-benzenesulphonyl)-3-(2-isobutoxy-5-methoxyphenyl)-3-(4-pyridin-4-yl-piperazin-1-yl)-2,3-dihydro-1H-indol-2-one ESI-MS: [M+H$^+$]=698.30;
$^1$H-NMR (500 MHz, CDCl$_3$) δ (ppm): 8.23 (2H, d), 8.12 (1H, d), 8.07 (1H, d), 7.61 (1H, d), 7.46 (1H, s), 7.23 (1H, s), 6.80 (1H, d), 6.73 (1H, d), 6.57 (1H, d), 6.53 (2H, d), 6.40 (1H, s), 3.80 (6H, s), 3.64 (1H, m), 3.61 (3H, s), 3.45 (1H, t), 3.23-2.76 (3H, m br.), 2.53-2.27 (2H, m br.), 0.74 (6H, m sym.).

Example 104

(±)-5-Cyano-1-(2,4-dimethoxy-benzenesulphonyl)-3-(2-ethoxy-4-methoxyphenyl)-3-(4-pyridin-4-yl-piperazin-1-yl)-2,3-dihydro-1H-indol-2-one ESI-MS: [M+H$^+$]=670.20;
$^1$H-NMR (500 MHz, CDCl$_3$) δ (ppm): 8.23 (2H, d), 8.13 (1H, d), 8.06 (1H, d), 7.71 (1H, d), 7.62 (1H, d), 7.18 (1H, s), 6.62-6.52 (4H, m), 6.40 (1H, s), 6.35 (1H, s), 3.91 (1H, quint.), 3.85-3.72 [7H, m incl. 3.81 (3H, s), 3.80 (3H, s)], 3.63 (3H, s), 2.42 (2H, s br.), 1.93 (2H, s br.), 1.15 (3H, t).

Example 105

(±)-5-Cyano-1-(2,4-dimethoxy-benzenesulphonyl)-3-(2-ethoxy-5-ethyl-phenyl)-3-[4-(2-isopropyl-pyridin-4-yl)-piperazin-1-yl]-2,3-dihydro-1H-indol-2-one ESI-MS: [M+H$^+$]=710.30;
$^1$H-NMR (500 MHz, CDCl$_3$) δ (ppm): 8.20 (1H, d), 8.13 (1H, d), 8.08 (1H, d), 7.67 (1H, s), 7.62 (1H, d), 7.19 (1H, s), 7.10 (1H, d), 6.71 (1H, d), 6.60 (1H, d), 6.56 (1H, s), 6.41 (2H, s), 3.91 (1H, quint.), 3.82 (3H, s), 3.76 (1H, quint.), 3.65 (3H, s), 2.90 (1H, quint.), 2.66 (2H, sept.), 2.57-2.14 (2H, m br.), 1.32-1.21 (10H, m), 1.13 (3H, t).

Example 106

(+)-5-Cyano-1-(2,4-dimethoxy-benzenesulphonyl)-3-(2-ethoxy-5-methoxyphenyl)-3-[4-(2-methyl-pyridin-4-yl)-piperazin-1-yl]-2,3-dihydro-1H-indol-2-one ESI-MS: [M+H$^+$]=684.00;
$^1$H-NMR (500 MHz, CDCl$_3$) δ (ppm): 8.12 (2H, m sym.), 8.07 (1H, d), 7.62 (1H, d), 7.44 (1H, s), 7.21 (1H, s), 6.80 (1H, d), 6.73 (1H, d), 6.59 (1H, d), 6.46-6.37 (3H, m), 3.86 (1H, quint.), 3.80 (6H, s), 3.72 (1H, quint.), 3.65 (3H, s), 2.43 (5H, sbr.), 1.11 (3H, t).
α (20° C., c=1 mg/ml, CHCl$_3$, I=1 dm): +106°;

Example 107

(±)-5-Cyano-1-(2,4-dimethoxy-benzenesulphonyl)-3-(2-ethoxy-5-ethyl-phenyl)-3-[4-(2-methyl-pyridin-4-yl)-piperazin-1-yl]-2,3-dihydro-1H-indol-2-one ESI-MS: [M+H$^+$]=682.25;
$^1$H-NMR (500 MHz, CDCl$_3$) δ (ppm): 8.14 (2H, m sym.), 8.07 (1H, d), 7.66 (1H, s), 7.63 (1H, d), 7.20 (1H, s), 7.10 (1H, d), 6.70 (1H, d), 6.60 (1H, d), 6.44 (1H, s), 6.40 (2H, m), 3.92 (1H, quint.), 3.82 (3H, s), 3.76 (1H, quint.), 3.65 (3H, s), 2.66 (2H, sept.), 2.44 (4H, s br.), 2.08 (1H, s br.), 1.25 (3H, t), 1.11 (3H, t).

Example 108

(±)-5-Cyano-1-(2-ethoxy-4-methoxy-benzenesulphonyl)-3-(2-ethoxyphenyl)-3-(4-pyridin-4-yl-piperazin-1-yl)-2,3-dihydro-1H-indol-2-one×trifluoroacetic acid ESI-MS: [M+H$^+$]=654.25;
$^1$H-NMR (500 MHz, DMSO) δ (ppm): 8.22 (2H, d), 8.01 (1H, d), 7.92 (2H, d), 7.88 (1H, d), 7.36-7.28 (2H, m), 7.15-7.06 (3H, m), 6.95 (1H, d), 6.64 (1H, d), 6.57 (1H, s), 4.03 (1H, quint.), 3.91 (1H, quint.), 3.85 (1H, quint.), 3.77-3.68 (4H, m), 2.42-2.06 (m br.), 1.55 (1H, s br.), 1.03 (3H, t), 0.97 (3H, t).

Example 109

(±)-5-Cyano-1-(5-chloro-2-ethoxy-4-methoxy-benzenesulphonyl)-3-(2-ethoxyphenyl)-3-(4-pyridin-4-yl-piperazin-1-yl)-2,3-dihydro-1H-indol-2-one×trifluoroacetic acid ESI-MS: 688.15;
$^1$H-NMR (500 MHz, DMSO) δ (ppm): 8.23 (2H, d), 8.00 (1H, d), 7.93 (1H, d), 7.91-7.85 (2H, m), 7.36-7.30 (2H, m), 7.12 (1H, d), 7.10 (2H, d), 6.96 (1H, d), 6.85 (1H, s), 4.16 (1H, quint.), 4.06 (1H, quint.), 3.90 (3H, s), 3.83 (1H, m), 3.72 (1H, quint.), 2.28 (m br.), 1.02 (3H, t), 0.97 (3H, t).

Example 110

5-Cyano-1-(2,4-dimethoxybenzenesulphonyl)-3-(2-ethoxy-3-methoxyphenyl)-3-[4-(2-isopropylpyridin-4-yl)-piperazin-1-yl]-2,3-dihydro-1H-indol-2-one× trifluoroacetic acid

ESI-MS: [M+H$^+$]=712.25

Example 111

5-Cyano-1-(2,4-dimethoxybenzenesulphonyl)-3-(2-ethoxy-4-methoxyphenyl)-3-[4-(2-isopropylpyridin-4-yl)-piperazin-1-yl]-2,3-dihydro-1H-indol-2-one× trifluoroacetic acid

ESI-MS: [M+H$^+$]=712.25

Example 112

5-Cyano-3-(2-ethoxyphenyl)-1-(4-fluoro-2-trifluoromethylbenzenesulphonyl)-3-(4-pyridin-4-yl-piperazin-1-yl)-2,3-dihydro-1H-indol-2-one×trifluoroacetic acid

ESI-MS: [M+H$^+$]=666.15

Example 113

5-Cyano-3-(2-ethoxyphenyl)-1-(4-isopropoxybenzenesulphonyl)-3-(4-pyridin-4-yl-piperazin-1-yl)-2,3-dihydro-1H-indol-2-one×trifluoroacetic acid

ESI-MS: [M+H$^+$]=638.25

Example 114

5-Cyano-3-(2-ethoxyphenyl)-3-(4-pyridin-4-yl-piperazin-1-yl)-1-(toluene-2-sulphonyl)-2,3-dihydro-1H-indol-2-one

ESI-MS: [M+H$^+$]=594.20

Example 115

5-Cyano-3-(2-ethoxyphenyl)-1-(2-fluoro-4-methylbenzenesulphonyl)-3-(4-pyridin-4-yl-piperazin-1-yl)-2,3-dihydro-1H-indol-2-one

ESI-MS: [M+H$^+$]=612.20

Example 116

5-Cyano-1-(2,4-dimethylbenzenesulphonyl)-3-(2-ethoxyphenyl)-3-(4-pyridin-4-yl-piperazin-1-yl)-2,3-dihydro-1H-indol-2-one×trifluoroacetic acid

ESI-MS: [M+H$^+$]=608.25

Example 117

5-Cyano-1-(2-chlorobenzenesulphonyl)-3-(2-ethoxyphenyl)-3-(4-pyridin-4-yl-piperazin-1-yl)-2,3-dihydro-1H-indol-2-one×trifluoroacetic acid ESI-MS: M 614.15 (Cl)

Example 118

5-Cyano-3-(2-ethoxyphenyl)-3-(4-pyridin-4-yl-piperazin-1-yl)-1-(2-trifluoromethoxybenzenesulphonyl)-2,3-dihydro-1H-indol-2-one×trifluoroacetic acid

ESI-MS: [M+H$^+$]=664.25

Example 119

5-Cyano-1-(2-cyanobenzenesulphonyl)-3-(2-ethoxyphenyl)-3-(4-pyridin-4-yl-piperazin-1-yl)-2,3-dihydro-1H-indol-2-one×trifluoroacetic acid

ESI-MS: [M+H$^+$]=605.20

Example 120

5-Cyano-3-(2-ethoxyphenyl)-3-(4-pyridin-4-yl-piperazin-1-yl)-1-(2-trifluoromethylbenzenesulphonyl)-2,3-dihydro-1H-indol-2-one

ESI-MS: [M+H$^+$]=648.15

Example 121

5-Cyano-3-(2-ethoxyphenyl)-1-(2-methanesulphonylbenzenesulphonyl)-3-(4-pyridin-4-yl-piperazin-1-yl)-2,3-dihydro-1H-indol-2-one

ESI-MS: [M+H$^+$]=658.10

Example 122

5-Cyano-1-(2,4-dimethoxybenzenesulphonyl)-3-(2-ethoxy-5-methoxyphenyl)-3-[2-(pyridin-4-ylamino)-ethylamino]-2,3-dihydro-1H-indol-2-one

ESI-MS: [M+H$^+$]=644.25

In a similar way, the following compounds (see Tables 1 to 8) can be prepared, using the synthesis steps described in synthesis scheme 1 and using the correspondingly substituted starting compounds:

Further examples of compounds according to the invention are compounds of general formula (I)

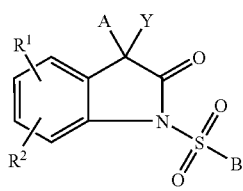

(I)

in which the variables R$^1$, R$^2$, A, B and Y, each independently of one another, are selected from the group comprising R$^1$=CN in position 5 (CN; see Tables 1 and 8), methoxy in position 5 (OMe; see Tables 2 and 5), methyl in position 5 (Me; see Tables 3 and 6) and chlorine in position 5 (Cl; see Tables 4 and 7);

R$^2$=hydrogen

A=2-ethoxyphenyl (2-OEt-Ph), 2-ethoxy-5-methoxyphenyl (2-OEt-5-OMe-Ph), 2-ethoxy-5-methylphenyl (2-OEt-5-Me-Ph) and 2-ethoxy-4-fluoro-phenyl (2-OEt-4-F-Ph);

B=4-methoxyphenyl (4-OCH$_3$-Ph), 4-cyanophenyl (4-CN-Ph) and 2,4-dimethoxyphenyl (2,4-Di-OMe-Ph).

Y=Y1, Y2, Y3, Y4, Y5, Y6, Y14, Y15, Y16 and Y17, having the following meanings:

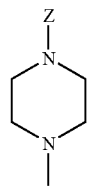

Y1

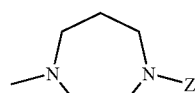

Y2

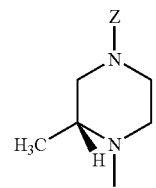

Y 5/6 or enantiomer

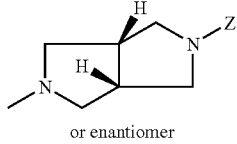

Y14/15 or enantiomer

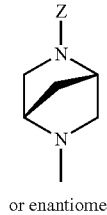

Y16/17 or enantiomer

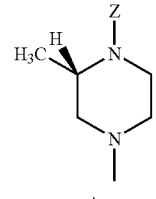

Y 3/4 or enantiomer where Z in each case denotes 4-pyridinyl (in Tables 1 to 4) and 2-methyl-pyridin-4-yl (in Tables 5 to 8).

As examples of the aforementioned compounds according to the invention, compounds of the above general formula (I) are listed below in Table 1, where the residues A, B, X and Y are in each case to have the individual meanings given in one line in Table 1.

TABLE 1

(with Z = 4-pyridinyl and $R^1$ = 5-CN)

| Example | A | B | X | Y |
|---|---|---|---|---|
| 123 | 2-OEt—Ph | 4-CN—Ph | H | Y1 |
| 124 | 2-OEt—Ph | 4-OMe—Ph | H | Y1 |
| 125 | 2-OEt-5-OMe—Ph | 4-CN—Ph | H | Y1 |
| 126 | 2-OEt-5-OMe—Ph | 4-OMe—Ph | H | Y1 |
| 127 | 2-OEt-4-F—Ph | 4-CN—Ph | H | Y1 |
| 128 | 2-OEt-4-F—Ph | 4-OMe—Ph | H | Y1 |
| 129 | 2-OEt—Ph | 4-CN—Ph | H | Y2 |
| 130 | 2-OEt—Ph | 4-OMe—Ph | H | Y2 |
| 131 | 2-OEt-5-OMe—-Ph | 4-CN—Ph | H | Y2 |
| 132 | 2-OEt-5-OMe—Ph | 4-OMe—Ph | H | Y2 |
| 133 | 2-OEt-4-F—Ph | 4-CN—Ph | H | Y2 |
| 134 | 2-OEt-4-F—Ph | 4-OMe—Ph | H | Y2 |
| 135 | 2-OEt—Ph | 4-CN—Ph | H | Y3 |
| 136 | 2-OEt—Ph | 4-OMe—Ph | H | Y3 |
| 137 | 2-OEt-5-OMe—Ph | 4-CN—Ph | H | Y3 |
| 138 | 2-OEt-5-OMe—Ph | 4-OMe—Ph | H | Y3 |
| 139 | 2-OEt-4-F—Ph | 4-CN—Ph | H | Y3 |
| 140 | 2-OEt-4-F—Ph | 4-OMe—Ph | H | Y3 |
| 141 | 2-OEt—Ph | 4-CN—Ph | H | Y4 |
| 142 | 2-OEt—Ph | 4-OMe—Ph | H | Y4 |
| 143 | 2-OEt-5-OMe—Ph | 4-CN—Ph | H | Y4 |
| 144 | 2-OEt-5-OMe—Ph | 4-OMe—Ph | H | Y4 |
| 145 | 2-OEt-4-F—Ph | 4-CN—Ph | H | Y4 |
| 146 | 2-OEt-4-F—Ph | 4-OMe—Ph | H | Y4 |
| 147 | 2-OEt—Ph | 4-CN—Ph | H | Y5 |
| 148 | 2-OEt—Ph | 4-OMe—Ph | H | Y5 |
| 149 | 2-OEt-5-OMe—Ph | 4-CN—Ph | H | Y5 |
| 150 | 2-OEt-5-OMe—Ph | 4-OMe—Ph | H | Y5 |
| 151 | 2-OEt-4-F—Ph | 4-CN—Ph | H | Y5 |
| 152 | 2-OEt-4-F—Ph | 4-OMe—Ph | H | Y5 |
| 153 | 2-OEt—Ph | 4-CN—Ph | H | Y6 |
| 154 | 2-OEt—Ph | 4-OMe—Ph | H | Y6 |
| 155 | 2-OEt-5-OMe—Ph | 4-CN—Ph | H | Y6 |
| 156 | 2-OEt-5-OMe—Ph | 4-OMe—Ph | H | Y6 |
| 157 | 2-OEt-4-F—Ph | 4-CN—Ph | H | Y6 |
| 158 | 2-OEt-4-F—Ph | 4-OMe—Ph | H | Y6 |
| 159 | 2-OEt—Ph | 4-CN—Ph | H | Y14 |
| 160 | 2-OEt—Ph | 4-OMe—Ph | H | Y14 |
| 161 | 2-OEt-5-OMe—Ph | 4-CN—Ph | H | Y14 |
| 162 | 2-OEt-5-OMe—Ph | 4-OMe—Ph | H | Y14 |
| 163 | 2-OEt-4-F—Ph | 4-CN—Ph | H | Y14 |
| 164 | 2-OEt-4-F—Ph | 4-OMe—Ph | H | Y14 |
| 165 | 2-OEt—Ph | 4-CN—Ph | H | Y15 |
| 166 | 2-OEt—Ph | 4-OMe—Ph | H | Y15 |
| 167 | 2-OEt-5-OMe—Ph | 4-CN—Ph | H | Y15 |
| 168 | 2-OEt-5-OMe—Ph | 4-OMe—Ph | H | Y15 |
| 169 | 2-OEt-4-F—Ph | 4-CN—Ph | H | Y15 |
| 170 | 2-OEt-4-F—Ph | 4-OMe—Ph | H | Y15 |
| 171 | 2-OEt—Ph | 4-CN—Ph | H | Y16 |
| 172 | 2-OEt—Ph | 4-OMe—Ph | H | Y16 |
| 173 | 2-OEt-5-OMe—Ph | 4-CN—Ph | H | Y16 |
| 174 | 2-OEt-5-OMe—Ph | 4-OMe—Ph | H | Y16 |
| 175 | 2-OEt-4-F—Ph | 4-CN—Ph | H | Y16 |
| 176 | (2-OEt-4-F—Ph | 4-OMe—Ph | H | Y16 |
| 177 | 2-OEt—Ph | 4-CN—Ph | H | Y17 |
| 178 | 2-OEt—Ph | 4-OMe—Ph | H | Y17 |
| 179 | 2-OEt-5-OMe—Ph | 4-CN—Ph | H | Y17 |
| 180 | 2-OEt-5-OMe—Ph | 4-OMe—Ph | H | Y17 |
| 181 | 2-OEt-4-F—Ph | 4-CN—Ph | H | Y17 |
| 182 | 2-OEt-4-F—Ph | 4-OMe—Ph | H | Y17 |
| 183 | 2-OEt—Ph | 2,4-Di-OMe—Ph | H | Y1 |
| 184 | 2-OEt-5-OMe—Ph | 2,4-Di-OMe—Ph | H | Y1 |
| 185 | 2-OEt-4-F—Ph | 2,4-Di-OMe—Ph | H | Y1 |
| 186 | 2-OEt-5-Me—Ph | 2,4-Di-OMe—Ph | H | Y1 |
| 187 | 2-OEt-5-Me—Ph | 4-CN—Ph | H | Y1 |
| 188 | 2-OEt-5-Me—Ph | 4-OMe—Ph | H | Y1 |
| 189 | 2-OEt—Ph | 2,4-Di-OMe—Ph | H | Y2 |
| 190 | 2-OEt-5-OMe—Ph | 2,4-Di-OMe—Ph | H | Y2 |
| 191 | 2-OEt-4-F—Ph | 2,4-Di-OMe—Ph | H | Y2 |
| 192 | 2-OEt-5-Me—Ph | 2,4-Di-OMe—Ph | H | Y2 |
| 193 | 2-OEt-5-Me—Ph | 4-CN—Ph | H | Y2 |
| 194 | 2-OEt-5-Me—Ph | 4-OMe—Ph | H | Y2 |
| 195 | 2-OEt—Ph | 2,4-Di-OMe—Ph | H | Y3 |
| 196 | 2-OEt-5-OMe—Ph | 2,4-Di-OMe—Ph | H | Y3 |
| 197 | 2-OEt-4-F—Ph | 2,4-Di-OMe—Ph | H | Y3 |
| 198 | 2-OEt-5-Me—Ph | 2,4-Di-OMe—Ph | H | Y3 |
| 199 | 2-OEt-5-Me—Ph | 4-CN—Ph | H | Y3 |
| 200 | 2-OEt-5-Me—Ph | 4-OMe—Ph | H | Y3 |
| 201 | 2-OEt—Ph | 2,4-Di-OMe—Ph | H | Y4 |
| 202 | 2-OEt-5-OMe—Ph | 2,4-Di-OMe—Ph | H | Y4 |
| 203 | 2-OEt-4-F—Ph | 2,4-Di-OMe—Ph | H | Y4 |
| 204 | 2-OEt-5-Me—Ph | 2,4-Di-OMe—Ph | H | Y4 |
| 205 | 2-OEt-5-Me—Ph | 4-CN—Ph | H | Y4 |
| 206 | 2-OEt-5-Me—Ph | 4-OMe—Ph | H | Y4 |
| 207 | 2-OEt—Ph | 2,4-Di-OMe—Ph | H | Y5 |
| 208 | 2-OEt-5-OMe—Ph | 2,4-Di-OMe—Ph | H | Y5 |
| 209 | 2-OEt-4-F—Ph | 2,4-Di-OMe—Ph | H | Y5 |
| 210 | 2-OEt-5-Me—Ph | 2,4-Di-OMe—Ph | H | Y5 |
| 211 | 2-OEt-5-Me—Ph | 4-CN—Ph | H | Y5 |
| 212 | 2-OEt-5-Me—Ph | 4-OMe—Ph | H | Y5 |
| 213 | 2-OEt—Ph | 2,4-Di-OMe—Ph | H | Y6 |
| 214 | 2-OEt-5-OMe—Ph | 2,4-Di-OMe—Ph | H | Y6 |
| 215 | 2-OEt-4-F—Ph | 2,4-Di-OMe—Ph | H | Y6 |
| 216 | 2-OEt-5-Me—Ph | 2,4-Di-OMe—Ph | H | Y6 |
| 217 | 2-OEt-5-Me—Ph | 4-CN—Ph | H | Y6 |
| 218 | 2-OEt-5-Me—Ph | 4-OMe—Ph | H | Y6 |
| 219 | 2-OEt—Ph | 2,4-Di-OMe—Ph | H | Y14 |
| 220 | 2-OEt-5-OMe—Ph | 2,4-Di-OMe—Ph | H | Y14 |
| 221 | 2-OEt-4-F—Ph | 2,4-Di-OMe—Ph | H | Y14 |
| 222 | 2-OEt-5-Me—Ph | 2,4-Di-OMe—Ph | H | Y14 |
| 223 | 2-OEt-5-Me—Ph | 4-CN—Ph | H | Y14 |
| 224 | 2-OEt-5-Me—Ph | 4-OMe—Ph | H | Y14 |
| 225 | 2-OEt—Ph | 2,4-Di-OMe—Ph | H | Y15 |
| 226 | 2-OEt-5-OMe—Ph | 2,4-Di-OMe—Ph | H | Y15 |
| 227 | 2-OEt-4-F—Ph | 2,4-Di-OMe—Ph | H | Y15 |
| 228 | 2-OEt-5-Me—Ph | 2,4-Di-OMe—Ph | H | Y15 |
| 229 | 2-OEt-5-Me—Ph | 4-CN—Ph | H | Y15 |
| 230 | 2-OEt-5-Me—Ph | 4-OMe—Ph | H | Y15 |
| 231 | 2-OEt—Ph | 2,4-Di-OMe—Ph | H | Y16 |
| 232 | 2-OEt-5-OMe—Ph | 2,4-Di-OMe—Ph | H | Y16 |
| 233 | 2-OEt-4-F—Ph | 2,4-Di-OMe—Ph | H | Y16 |
| 234 | 2-OEt-5-Me—Ph | 2,4-Di-OMe—Ph | H | Y16 |
| 235 | 2-OEt-5-Me—Ph | 4-CN—Ph | H | Y16 |
| 236 | 2-OEt-5-Me—Ph | 4-OMe—Ph | H | Y16 |
| 237 | 2-OEt—Ph | 2,4-Di-OMe—Ph | H | Y17 |
| 238 | 2-OEt-5-OMe—Ph | 2,4-Di-OMe—Ph | H | Y17 |
| 239 | 2-OEt-4-F—Ph | 2,4-Di-OMe—Ph | H | Y17 |
| 240 | 2-OEt-5-Me—Ph | 2,4-Di-OMe—Ph | H | Y17 |
| 241 | 2-OEt-5-Me—Ph | 4-CN—Ph | H | Y17 |
| 242 | 2-OEt-5-Me—Ph | 4-OMe—Ph | H | Y17 |

Table 2: as Table 1 but with Z=4-pyridinyl and $R^1$=5-OMe: Examples 243 to 362 in the order from top to bottom as in Table 1.

Table 3: as Table 1 but with Z=4-pyridinyl and $R^1$=5-Me Examples 363 to 482 in the order from top to bottom as in Table 1.

Table 4: as Table 1 but with Z=4-pyridinyl and $R^1$=5-Cl Examples 483 to 602 in the order from top to bottom as in Table 1.

Table 5: as Table 1 but with Z=2-methyl-pyridin-4-yl and $R^1$=6-OMe Examples 603 to 722 in the order from top to bottom as in Table 1.

Table 6: as Table 1 but with Z=2-methyl-pyridin-4-yl and $R^1$=5-Me Examples 723 to 842 in the order from top to bottom as in Table 1.

Table 7: as Table 1 but with Z=2-methyl-pyridin-4-yl and $R^1$=5-Cl Examples 843 to 962 in the order from top to bottom as in Table 1.

Table 8: as Table 1 but with Z=2-methyl-pyridin-4-yl and $R^1$=5-CN Examples 962 to 1082 in the order from top to bottom as in Table 1.

Methods for Determining Biological Activity
Vasopressin V1b Receptor Binding Test:
Substances:
The test substances were dissolved at a concentration of $10^{-2}$ M in DMSO and diluted further in DMSO to $5 \times 10^{-4}$ M to 5×10$^{-9}$ M. These DMSO solutions were diluted 1:10 with test buffer. The concentration of substance was again diluted 1:5 in the test preparation.

Membrane Preparation:

CHO-K1 cells with stably expressed human vasopressin V1b receptor (clone 3H2) were harvested and homogenized in 50 mM Tris-HCl and in the presence of protease inhibitors (Roche complete Mini #1836170) with a Polytron Homogenizer at medium setting for 2×10 seconds, and then centrifuged for 1 h at 40 000×g. The membrane pellet was homogenized and centrifuged again as described, and then taken up in 50 mM Tris-HCl, pH 7.4, homogenized and, frozen in aliquots, stored at −190° C. in liquid nitrogen.

Binding Test:

The binding test was carried out on the basis of the method of Tahara et al. (Tahara A et al., Brit. J. Pharmacol. 125, 1463-1470 (1998)).

The incubation buffer was: 50 mM Tris, 10 mM MgCl$_2$, 0.1% BSA, pH 7.4. In the test preparation (250 μl), membranes (50 μg/ml protein in incubation buffer) of CHO-K1 cells with stably expressed human V1b receptors (cell line hV1b__3H2_CHO) were incubated with 1.5 nM $^3$H-AVP (8-Arg-vasopressin, PerkinElmer #18479) in incubation buffer (50 mM Tris, 10 mM MgCl$_2$, 0.1% BSA, pH 7.4) (total binding) or in addition with increasing concentrations of test substance (displacement experiment). The nonspecific binding was determined with 1 μM AVP (Bachem #H1780). All determinations were performed in triplicate. After incubation (60 minutes at room temperature), the free radioligand was filtered off by vacuum filtration (Skatron cell harvester 7000) on Whatman GF/B glass-fibre filter mats and the filters were transferred to scintillation vessels. Liquid scintillation measurement was performed in a Tricarb instrument, Model 2000 or 2200CA (Packard). Conversion of the measured cpm to dpm was performed with the aid of a standard quench series.

Evaluation:

The binding parameters were calculated by nonlinear regression in SAS. The algorithms of the program work similarly to the LIGAND evaluation program (Munson P J and Rodbard D, Analytical Biochem. 107, 220-239 (1980)). The Kd value of $^3$H-AVP to the recombinant hV2 receptors is 0.4 nM and was employed for determining the Ki value.

Vasopressin V1a Receptor Binding Test:

Substances:

The test substances were dissolved at a concentration of 10$^{-2}$ M in DMSO. These DMSO solutions were further diluted in incubation buffer (50 mM Tris, 10 mM MgCl$_2$, 0.1% BSA, pH 7.4).

Membrane Preparation:

CHO-K1 cells with stably expressed human vasopressin V1a receptor (clone 5) were harvested and homogenized in 50 mM Tris-HCl and in the presence of protease inhibitors (Roche complete Mini #1836170) with a Polytron homogenizer at medium setting for 2×10 seconds and then centrifuged for 1 h at 40 000×g. The membrane pellet was homogenized and centrifuged again as described, and then taken up in 50 mM Tris-HCl, pH 7.4, homogenized and, frozen in aliquots, stored at −190° C. in liquid nitrogen.

Binding Test:

The binding test was carried out on the basis of the method of Tahara et al. (Tahara A et al., Brit. J. Pharmacol. 125, 1463-1470 (1998)).

The incubation buffer was: 50 mM Tris, 10 mM MgCl$_2$, 0.1% BSA, pH 7.4. In the test preparation (250 μl), membranes (20 μg/ml protein in incubation buffer) of CHO-K1 cells with stably expressed human V1a receptors (cell line hV1a__5_CHO) were incubated with 0.04 nM $^{125}$I-AVP (8-Arg-vasopressin, NEX 128) in incubation buffer (50 mM Tris, 10 mM MgCl$_2$, 0.1% BSA, pH 7.4) (total binding) or in addition with increasing concentrations of test substance (displacement experiment). The nonspecific binding was determined with 1 μM AVP (Bachem #H1780). The determinations were performed in triplicate. After incubation (60 minutes at room temperature), the free radioligand was filtered off by vacuum filtration (Skatron cell harvester 7000) on Whatman GF/B glass-fibre filter mats and the filters were transferred to scintillation vessels. Liquid scintillation measurement was performed in a Tricarb instrument, Model 2000 or 2200CA (Packard). Conversion of the measured cpm to dpm was performed with the aid of a standard quench series.

Evaluation:

The binding parameters were calculated by nonlinear regression in SAS. The algorithms of the program work similarly to the LIGAND evaluation program (Munson P J and Rodbard D, Analytical Biochem. 107, 220-239 (1980)). The Kd value of $^{125}$I-AVP to the recombinant hV1a-receptors was determined in saturation experiments. A Kd value of 1.33 nM was employed for determining the Ki value.

Vasopressin V2 Receptor Binding Test:

Substances:

The test substances were dissolved at a concentration of 10$^{-2}$ M in DMSO and further diluted in DMSO to 10$^{-3}$ M to 5×10$^{-9}$ M. These DMSO solutions were diluted further in incubation buffer (50 mM Tris, 10 mM MgCl$_2$, 0.1% BSA, pH 7.4).

Membrane Preparation:

CHO-K1 cells with stably expressed human vasopressin V2 receptor (clone 23) were harvested and homogenized in 50 mM Tris-HCl and in the presence of protease inhibitors (Roche complete Mini #1836170) with a Polytron Homogenizer at medium setting for 2×10 seconds and then centrifuged for 1 h at 40 000×g. The membrane pellet was homogenized and centrifuged again as described, and then taken up in 50 mM Tris-HCl, pH 7.4, homogenized and, frozen in aliquots, stored at −190° C. in liquid nitrogen.

Binding Test:

The binding test was performed on the basis of the method of Tahara et al. (Tahara A et al., Brit. J. Pharmacol. 125, 1463-1470 (1998)).

The incubation buffer was: 50 mM Tris, 10 mM MgCl$_2$, 0.1% BSA, pH 7.4. In the test preparation (250 μl), membranes (50 μg/ml protein in incubation buffer) of CHO-K1 cells with stably expressed human V2 receptors (cell line hV2__23_CHO) were incubated with 1-2 nM $^3$H-AVP (8-Arg-vasopressin, PerkinElmer #18479) in incubation buffer (50 mM Tris, 10 mM MgCl$_2$, 0.1% BSA, pH 7.4) (total binding) or in addition with increasing concentrations of test substance (displacement experiment). The nonspecific binding was determined with 1 μM AVP (Bachem #H1780). The determinations were performed in triplicate.

After incubation (60 minutes at room temperature), the free radioligand was filtered off by vacuum filtration (Skatron cell harvester 7000) on Whatman GF/B glass-fibre filter mats and the filters were transferred to scintillation vessels. The liquid scintillation measurement was performed in a Tricarb instrument, Model 2000 or 2200CA (Packard). Conversion of the measured cpm to dpm was performed with the aid of a standard quench series.

Evaluation:

The binding parameters were calculated by nonlinear regression in SAS. The algorithms of the program work similarly to the LIGAND evaluation program (Munson P J and Rodbard D, Analytical Biochem. 107, 220-239 (1980)). The Kd value of ³H-AVP to the recombinant hV1b-receptors is 2.4 nM and was employed for determining the Ki value.
Oxytocin-Receptor Binding Test
Substances:
The substances were dissolved at a concentration of $10^{-2}$ M or $10^{-3}$ M in DMSO and diluted with incubation buffer (50 mM Tris, 10 mM $MgCl_2$, 0.1% BSA, pH 7.4).
Cell Preparation:
Confluent HEK-293 cells with transiently expressing recombinant human oxytocin receptors were centrifuged at 750×g for 5 minutes at room temperature. The residue was taken up in ice-cold lysis buffer (50 mM Tris-HCl, 10% glycerin, pH 7.4 and Roche Complete Protease-Inhibitor) and submitted to osmotic shock for 20 minutes at 4° C. Then the lysed cells were centrifuged at 750×g for 20 minutes at 4° C., the residue was taken up in incubation buffer and aliquots of $10^7$ cells/ml were prepared. The aliquots were stored frozen at −80° C. until use.
Binding Test:
On the day of the test, the cells were thawed, diluted with incubation buffer and homogenized with a Multipette Combitip (Eppendorf, Hamburg). The reaction charge of 0.250 ml was composed of 2 to 5×10⁴ recombinant cells, 3-4 nM ³H-oxytocin (PerkinElmer, NET 858) in the presence of test substance (inhibition curve) or incubation buffer only (total binding). The nonspecific binding was determined with $10^{-6}$ M oxytocin (Bachem A G, H2510). Determinations were performed in triplicate. Bound and free radioligand were separated by filtration under vacuum with Whatman GF/B glass-fibre filter using a Skatron Cell Harvester 7000. The bound radioactivity was determined by liquid scintillation measurement in a Tricarb Beta-Counter, Model 2000 or 2200CA (Packard).
Evaluation:
The binding parameters were calculated by nonlinear regression analysis (SAS), similarly to the LIGAND program of Munson and Rodbard (Analytical Biochem 1980; 107: 220-239). The Kd value of ³H-oxytocin to the recombinant hOT-receptors is 7.6 nM and was employed for determining the Ki value.
Effect on Vasopressin-Induced Calcium Increase in Cells Bearing a Cloned Human Vasopressin Receptor The functional activity of the test substances was investigated on CHO-K1 cells that were stably transfected with the human V1b receptor. Each well of a 96-well microtitre plate was seeded with 50 000 cells and incubated in a culture medium overnight at 37° C. in a saturated water vapour atmosphere with 5% $CO_2$. The culture medium comprised DMEM/Nut mix F12 with Glutamax I (from Invitrogen), 10% fetal calf serum, 100 units/ml penicillin, 100 μg/ml streptomycin and 800 μg/ml Geneticin. On the next day the cells were washed with culture medium and charged with a fluorescence dye for calcium in accordance with the manufacturer's instructions ($Ca^{++}$-Plus-Assay Kit, Molecular Devices). The cells were charged in the presence of probenecid (1 vol. %). The test substances were diluted with culture medium (final concentration $10^{-10}$ to $10^{-5}$ M) and incubated at room temperature for 15 minutes with the dye-charged cells. Then Arg-vasopressin ($10^{-8}$ M) was added and the maximum fluorescence signal was determined with an FLIPR-96 instrument (Molecular Devices). Concentration-effect curves were constructed using nonlinear regression algorithms (GraphPad Prism 3.0). Kb values were calculated from IC50 values according to Cheng and Prusoff (Kb=IC50/1+L/EC50).

For the compounds according to the invention, the affinities for the human vasopressin receptor V1b were measured according to the above test and the affinity constant (Ki) was determined. The following Table 2 shows the V1b receptor affinity of selected compounds (+++ denotes <50 nM, ++ denotes 50-500 nM).

TABLE 2

| Example No. | V1b Ki |
|---|---|
| 2 | ++ |
| 3 | +++ |
| 4 | ++ |
| 5 | +++ |
| 6 | +++ |
| 7 | ++ |
| 8 | ++ |
| 9 | ++ |
| 10 | +++ |
| 12 | ++ |
| 14 | ++ |
| 15 | ++ |
| 16 | ++ |
| 18 | ++ |
| 19 | +++ |
| 20 | ++ |
| 21 | +++ |
| 23 | ++ |
| 24 | +++ |
| 25 | ++ |
| 26 | ++ |
| 27 | ++ |
| 28 | +++ |
| 30 | +++ |
| 31 | +++ |
| 32 | ++ |
| 35 | ++ |
| 46 | ++ |
| 47 | ++ |
| 48 | ++ |
| 50 | +++ |
| 52 | +++ |
| 53 | ++ |
| 55 | +++ |
| 56 | ++ |
| 57 | +++ |
| 58 | +++ |
| 59 | +++ |
| 60 | +++ |
| 61 | ++ |
| 62 | +++ |
| 63 | +++ |
| 65 | ++ |
| 67 | +++ |
| 68 | ++ |
| 72 | ++ |
| 76 | ++ |
| 77 | ++ |
| 78 | ++ |
| 80 | ++ |
| 81 | ++ |
| 84 | ++ |
| 85 | ++ |
| 86 | ++ |
| 87 | ++ |
| 88 | ++ |
| 89 | ++ |
| 90 | ++ |
| 91 | ++ |
| 92 | +++ |
| 93 | +++ |
| 94 | +++ |
| 95 | +++ |
| 96 | +++ |
| 100 | +++ |
| 101 | +++ |
| 102 | +++ |
| 105 | +++ |
| 106 | +++ |
| 107 | +++ |
| 110 | +++ |

TABLE 2-continued

| Example No. | V1b Ki |
|---|---|
| 111 | +++ |
| 113 | ++ |
| 115 | ++ |
| 122 | +++ |

The invention claimed is:

1. A compound of general formula (I),

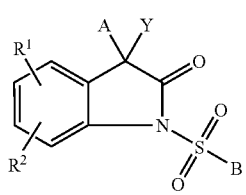

in which

A is $C_6$-$C_{10}$-aryl, which can be substituted with one, two, three or four residues selected from the group consisting of $R_A^1$, $R_A^2$, $R_A^3$ and/or $R_A^4$, in which $R_A^1$, $R_A^2$, $R_A^3$ and $R_A^4$ independently of one another and regardless of their respective occurrence, are selected from the group consisting of hydrogen, chlorine, bromine, iodine, fluorine, CN, in each case optionally substituted $OR_A^5$, $COR_A^5$, $COOR_A^5$, $SR_A^5$, $C_3$-$C_7$-cycloalkyl, $OCOR_A^5$, $SO_2NR_A^6R_A^7$, $CONR_A^6R_A^7$, $C_0$-$C_4$-alkylene-CN, $C_1$-$C_6$-haloalkyl, $C_1$-$C_6$-haloalkoxy, $NO_2$, $C_0$-$C_4$-alkylene-$OR_A^5$, $C_1C_6$-alkyl, $C_2$-$C_6$-alkenyl, $C_2$-$C_6$-alkynyl, $C_2$-$C_6$-alkenyloxy, $C_2$-$C_6$-alkynyloxy, $C_1$-$C_4$-alkylthio, $C_0$-$C_4$-alkylene-$COR_A^5$, $SO_2R_A^5$, $C_0$-$C_4$-alkylene-$COOR_A^5$, O—$C_1$-$C_4$-alkylene-$COOR_A^5$, $C_0$-$C_4$-alkylene-$SR_A^5$, $C_0$-$C_4$-alkylene-$C_3$-$C_7$-cycloalkyl, $C_0$-$C_4$-alkylene -$OCOR_A^5$, $C_0$-$C_4$-alkylene-$NR_A^6R_A^7$, $C_0$-$C_4$-alkylene-$SO_2NR_A^6R_A^7$, $C_0$-$C_4$-alkylene-$CONR_A^6R_A^7$, $C_1$-$C_4$-alkylene-$OCONR_A^6R_A^7$, $C_1$-$C_4$-alkylene-$SOR_A^5$, $C_1$-$C_4$-alkylene-$SO_2R_A^5$, NHCOO—$C_0$-$C_4$-alkylene-aryl, NHCOOH, $NH_2$, $NH(C_1$-$C_4$-alkyl), $N(C_1$-$C_4$-alkyl)$_2$, NHCHO, NHCONH$_2$, $N(C_0$-$C_4$-alkylene)CONH$_2$, $N(C_0$-$C_4$-alkylene)CONH($C_1$-$C_4$-alkyl), $NHCOCH_3$, $NO_2$, $(CH_2)_{0-2}$—OH, O—$C_1$-$C_6$-alkyl, $(CH_2)_{0-2}$—O—$C_1$-$C_4$-alkyl, O—$C_0$-$C_4$-alkylene-phenyl, phenyl, where two of the residues $R_A^1$, $R_A^2$, $R_A^3$ and $R_A^4$ positioned adjacent ("ortho") to one another can also form an, optionally substituted, fused saturated, unsaturated and/or aromatic 3- to 10-membered carbon ring or a cyclic acetal —O—$CH_2$—$CH_2$—O— or —O—$CH_2$—O— or a fused furan ring (—O—CH=CH—), and in which $R_A^5$ regardless of its respective occurrence denotes hydrogen, a linear or branched $C_1$-$C_6$-alkyl residue, or a linear or branched, optionally substituted $C_2$-$C_6$-alkenyl-, $C_2$-$C_6$-alkynyl, $C_3$-$C_7$cycloalkyl-, $C_1$-$C_4$-alkylene-$C_3$-$C_7$-cycloalkyl- or $C_1$-$C_4$-alkylene-($C_6$-$C_{10}$)-aryl residue, $R_A^6$ and $R_A^7$ independently of one another and regardless of their respective occurrence, denote hydrogen, a linear or branched, optionally substituted $C_1$-$C_6$-alkyl, $C_2$-$C_6$-alkenyl, $C_2$-$C_6$-alkynyl, $C_1$-$C_5$-alkylene-$C_1$-$C_4$-alkoxy, $C_3$-$C_7$-cycloalkyl, $C_1$-$C_4$-alkylene-$C_3$-$C_7$-cycloalkyl, $C_1$-$C_4$-alkylene-aryl residue, or an —$SO_2R_A^5$, —$CO_2R_A^5$, —CO—$NR_A^5 R_A^5$, or —$COR_A^5$ residue, or together with the nitrogen atom to which they are bonded are a 3-, 4-, 5-, 6- or 7-membered, saturated or unsaturated nitrogen heterocycle which may have a further heteroatom from the group of O, S and $NR_A^{76}$ and which is unsubstituted and/or may have 1, 2, 3 or 4 substituents $R_A^{77}$, where $R_A^{76}$ is selected from $C_1$-$C_6$-alkyl, $C_1$-$C_6$-haloalkyl, $C_1$-$C_6$-alkoxy, $C_1$-$C_6$-haloalkoxy, $C_3$-$C_6$-cycloalkyl, $C_3$-$C_6$-cycloalkoxy, $C_1$-$C_6$-alkylcarbonyl and $C_1$-$C_6$-haloalkylcarbonyl, $R_A^{77}$ has one of the meanings indicated for $R_A^{76}$, or is halogen, and where 2 substituents $R_A^{77}$ bonded to a C atom of the nitrogen heterocycle may also form a carbonyl oxygen, and B is an aromatic or partially aromatic $C_6$-$C_{10}$ single ring or fused double ring, which can be used substituted with at most four residues selected from the group consisting of $R_B^1$, $R_B^2$, $R_B^3$, and $R_B^4$, where $R_B^1$, $R_B^2$, $R_B^3$ and $R_B^4$ independently of one another and regardless of their respective occurrence, are selected from the group consisting of hydrogen, chlorine, bromine, iodine, fluorine, CN, $OR_B^5$, $COR_B^5$, $COOR_B^5$, $SR_B^5$, $C_3$-$C_7$-cycloalkyl, $OCOR_A^5$, $SO_2NR_A^6R_A^7$, $CONR_A^6R_A^7$, ($C_6$-$C_{10}$)-aryl, ($C_3$-$C_{10}$)-hetaryl, $NR_B^6R_B^7$, $C_3$-$C_7$-heterocycloalkyl, $C_3$-$C_7$-heterocycloalkenyl, $OCOR_B^5$, $SO_2NR_B^6R_B^7$, $CONR_B^6R_B^7$, $C_0$-$C_4$-alkylene-CN, $C_1$-$C_6$-haloalkyl, $C_1$-$C_6$-haloalkoxy, $NO_2$, $C_0$-$C_4$-alkylene-$OR_B^5$, O—$C_0$-$C_4$-alkylene-($C_6$-$C_{10}$)-aryl, O—$C_0$-$C_4$-alkylene-($C_2$-$C_{10}$)-hetaryl, $C_0$-$C_4$-alkylene-($C_6$-$C_{10}$)-aryl, $C_0$-$C_4$-alkylene-($C_2$-$C_{10}$)-hetaryl, $C_2$-$C_6$-alkenyl, $C_2$-$C_6$-alkynyl, $C_2$-$C_6$-alkenyloxy, $C_2$-$C_6$-alkynyloxy, $C_1$-$C_4$-alkylthio, $C_0$-$C_4$-alkylene-$NR_B^6R_B^7$, $C_0$-$C_4$-alkylene-$COR_B^5$, $SO_2R_B^5$, $C_0^4$-alkylene-$COOR_B^5$, O—$C_1$-$C_4$-alkylene-$COOR_B^5$, $C_0$-$C_4$-alkylene-$SR_B^5$, $C_0$-$C_4$-alkylene-$C_3$-$C_7$-cycloalkyl, $C_0$-$C_4$-alkylene-$C_3$-$C_7$-heterocycloalkenyl, $C_0$-$C_4$-alkylene-$OCOR_B^5$, $C_0$-$C_4$-alkylene -$SO_2NR_B^6R_B^7$, $C_0$-$C_4$-alkylene-$CONR_B^6R_B^7$, $C_1$-$C_4$-alkylene-$OCONR_B^6R_B^7$, $C_1$-$C_4$-alkylene -$SOR_B^5$, $C_1$-$C_4$-alkylene-$SO_2R_B^5$, NHCOO—$C_0$-$C_4$-alkylene-($C_6$-$C_{10}$)-aryl, NHCOO—($C_6$-$C_{10}$)-aryl, $NH_2$, $NH(C_1$-$C_4$-alkyl), $N(C_1$-$C_4$-alkyl)$_2$, morpholin-4-yl, pyrrolidin-1-yl, piperidin-1-yl, 4-piperazin-1-yl, 4-($C_1$-$C_4$-alkyl)-piperazin-1-yl;

where two of the residues $R_B^1$, $R_B^2$, $R_B^3$, or $R_B^4$ positioned adjacent ("ortho") to one another can also form a fused, unsaturated or aromatic 3- to 10-membered carbon ring, optionally substituted singly or multiply, identically or differently with the residues $C_1$-$C_6$-alkyl-, $OCH_3$ or halogen, in which $R_B^5$ regardless of its respective occurrence, denotes hydrogen, a linear or branched, optionally substituted $C_1$-$C_6$-alkyl-, $C_2$-$C_6$-alkenyl-, $C_2$-$C_6$-alkynyl, $C_1$-$C_5$-alkylene-$C_1$-$C_4$-alkoxy-, mono- or bis-($C_1$-$C_6$)-alkylamino-($C_1$-$C_4$)-alkylene or ($C_1$-$C_6$)-acylamino-($C_1$-$C_4$)-alkylene residue or an optionally substituted ($C_6$-$C_{10}$)-aryl, $C_3$-$C_7$-heterocycloalkyl, $C_3$-$C_7$-heterocycloalkenyl, ($C_3$-$C_{10}$)-hetaryl, $C_3$-$C_7$-cycloalkyl, $C_1$-$C_4$-alkylene-$C_3$-$C_7$-cycloalkyl, $C_1$-$C_4$-alkylene-($C_6$-$C_{10}$)-aryl, $C_1$-$C_4$-alkylene-$C_3$-$C_7$-heterocyloalkyl, $C_1$-$C_4$-alkylene-$C_3$-$C_7$-heterocycloalkenyl or $C_1$-$C_4$-alkylene-($C_2$-$C_{10}$)-hetaryl, $R_B^6$ and $R_B^7$ independently of one another and regardless of their respective occurrence, denote hydrogen, a linear or branched, optionally substituted $C_1$-$C_6$-alkyl-, $C_2$-$C_6$-alkenyl-, $C_2$-$C_6$-alkynyl, $C_1$-$C_5$-alkylene-$C_1$-$C_4$-alkoxy-, mono- or bis-($C_1$-$C_6$)-alkylamino-($C_1$-$C_4$)-alkylene- or ($C_1$-$C_6$)-acylamino-($C_1$-$C_4$)-alkylene residue or an optionally substituted ($C_6$-$C_{10}$)-aryl, $C_3$-$C_7$-heterocycloalkyl, $C_3$-$C_7$-heterocycloalkenyl, ($C_2$-$C_{10}$)-hetaryl, $C_3$-$C_7$-cycloalkyl, $C_1$-$C_4$-alkylene-$C_3$-$C_7$-cycloalkyl, $C_1$-$C_4$-alkylene-($C_6$-$C_{10}$)-aryl, $C_1$-$C_4$-alkylene-$C_3$-$C_7$-heterocyloalkyl, $C_1$-$C_4$-alkylene-$C_3$-$C_7$-heterocyloalkenyl or $C_1$-$C_4$-alkylene-($C_2$-$C_{10}$)-hetaryl residue, or an —$SO_2R_B^5$, —$CO_2R_B^5$, —CO—$NR_B^5R_B^5$, or $COR_B^5$ residue;

or $R_B^6$ and $R_B^7$ regardless of their respective occurrence, together represent a 3 to 7-membered, optionally substituted, or preferably substituted with $C_1$-$C_6$-alkyl-, OMe, halogen, saturated, unsaturated or aromatic heterocycle, which in addition to the ring nitrogen atom can contain up to three further different or identical heteroatoms selected from the group consisting of O, N and S, and optionally two residues $R^x$ and $R^x$ optionally substituted on this heterocycle together represent a fused, saturated, unsaturated or aromatic carbon ring or heterocycle, which can contain up to three different or identical heteroatoms selected from the group consisting of O, N and S, and the ring can optionally be substituted or a further, optionally substituted ring can be condensed on this ring, $R^1$ and $R^2$ independently of one another, denote one of the residues hydrogen, Br, F, Cl, I, $C_1$-$C_4$-alkylene-CN, CN, $C_1$-$C_6$-haloalkyl, $C_1$-$C_6$-haloalkoxy, $NO_2$, $C_1$-$C_4$-alkylene-$OR_X^1$, $OR_X^1$, O—$C_1$-$C_4$-alkylene-($C_6$-$C_{10}$)-aryl, O—$C_1$-$C_4$-alkylene-hetaryl, O-hetaryl, $C_1$-$C_4$-alkylene-($C_6$-$C_{10}$)-aryl, ($C_6$-$C_{10}$)-aryl, $C_1$-$C_4$-alkylene-hetaryl, ($C_2$-$C_{10}$)-hetaryl, $C_1$-$C_6$-alkyl, $C_2$-$C_6$-alkenyl, $C_2$-$C_6$-alkynyl, $C_2$-$C_6$-alkenyloxy, $C_2$-$C_6$-alkynyloxy, $C_1C_4$-alkylthio, $C_1$-$C_4$-alkylene-$NR_X^2R_X^3$, $NR_X^2R_X^3$, $C_1$-$C_4$-alkylene-$COR_X^1$, $SO_2R_X^1$, $C_1$-$C_4$-alkylene-CO—$OR_X^1$, $COOR_X^1$, O—$C_1$-$C_4$-alkylene-$COOR_X^1$, $C_1$-$C_4$-alkylene-$SR_X^1$, $SR_X^1$, $C_1$-$C_4$-alkylene-$C_3$-$C_7$-cycloalkyl, $C_3$-$C_7$-cycloalkyl, $C_1C_4$-alkylene-$C_3$-$C_7$-heterocycloalkyl, $C_3$-$C_7$-heterocycloalkyl, $C_1$-$C_4$-alkylene-$C_3$-$C_7$-heterocycloalkenyl, $C_3$-$C_7$-heterocycloalkenyl, $C_1$-$C_4$-alkylene-$OCOR_X^1$, $OCOR_X^1$, $C_1$-$C_4$-alkylene-$SO_2NR_X^2R_X^3$, $SO_2NR_X^2R_X^3$, $C_1$-$C_4$-alkylene-$CONR_X^2R_X^3$, $CONR_X^2R_X^3$, $C_1$-$C_4$-alkylene-$OCONR_X^2R_X^3$, $C_1$-$C_4$-alkylene-$SOR_X^1$, $C_1$-$C_4$-alkylene-$SO_2R_X^1$, NHCOO—$C_0$-$C_4$-alkylene-($C_6$-$C_{10}$)-aryl or NHCOO—($C_6$-$C_{10}$)-aryl in which $R_X^1$ regardless of its respective occurrence denotes hydrogen, a linear or branched, optionally substituted $C_1$-$C_6$-alkyl, $C_2$-$C_6$-alkenyl, $C_2$-$C_6$-alkynyl, $C_1$-$C_5$-alkylene-$C_1$-$C_4$-alkoxy, mono or bis-($C_1$-$C_6$)-alkylamino-($C_1$-$C_4$)-alkylene or ($C_1$-$C_6$)-acylamino-($C_1$-$C_4$)-alkylene residue or an optionally substituted ($C_6$-$C_{10}$)-aryl, $C_3$-$C_7$-heterocycloalkyl, $C_3$-$C_7$-heterocycloalkenyl, ($C_2$-$C_{10}$)-hetaryl, $C_3$-$C_7$-cycloalkyl, $C_1$-$C_4$-alkylene-$C_3$-$C_7$cycloalkyl, $C_1$-$C_4$-alkylene-($C_6$-$C_{10}$)-aryl, $C_1$-$C_4$-alkylene-$C_3$-$C_7$-heterocyloalkyl, $C_1$-$C_4$-alkylene $C_3$-$C_7$-heterocyloalkenyl or $C_1$-$C_4$-alkylene-($C_2$-$C_{10}$)-hetaryl, $R_X^2$ and $R_X^3$ independently of one another and regardless of their respective occurrence, denote hydrogen, a linear or branched, optionally substituted $C_1$-$C_6$-alkyl, $C_2$-$C_6$-alkenyl, $C_2$-$C_6$-alkynyl, $C_1$-$C_5$-alkylene-$C_1$-$C_4$-alkoxy, mono or bis-($C_1$-$C_6$)-alkylamino-($C_1$-$C_4$)-alkylene or ($C_1$-$C_6$)-acylamino-($C_1$-$C_4$)-alkylene or an optionally substituted ($C_6$-$C_{10}$)-aryl, $C_3$-$C_7$-heterocycloalkyl, $C_3$-$C_7$-heterocycloalkenyl, ($C_2$-$C_{10}$)-hetaryl, $C_3$-$C_7$-cycloalkyl, $C_1$-$C_4$-alkylene-$C_3$-$C_7$-cycloalkyl, $C_1$-$C_4$-alkylene-($C_6$-$C_{1\,0}$)-aryl, $C_1$-$C_4$-alkylene-$C_3$-$C_7$-heterocycloalkyl, $C_1$-$C_4$-alkylene-$C_3$-$C_7$-heterocyloalkenyl or $C_1$-$C_4$-alkylene-($C_2$--$C_{10}$)-hetaryl residue, or an —$SO_2R_X^1$, —$CO_2R_X^1$, —CO—$NR_X^1R_X^1$, or $COR_X^1$ residue, or $R_X^2$ and $R_X^3$ together can form a 3-, 4-, 5-, 6- or 7-membered saturated, unsaturated or aromatic ($C_2$-$C_{10}$)-heterocycle, optionally substituted, optionally preferably substituted with $C_1$-$C_6$-alkyl-, $OCH_3$, and/or halogen, which in addition to the ring nitrogen atom can contain one, two or three further different or identical heteroatoms selected from the group consisting of O, N, and S, and optionally two residues $R_X^4$ and $R_X^5$ substituted on this heterocycle together can form a single ring, fused double ring or fused triple ring with a total of 3 to 21 ring atoms, each of which can be saturated, unsaturated or aromatic and can optionally be substituted with up to six residues selected from the group consisting of $C_1$-$C_6$-alkyl, $OCH_3$ and halogen, where at least one ring can contain a ring nitrogen atom and in addition each ring, independently of one another, can contain up to three further different or identical heteroatoms selected from the group consisting of O, N, and S, or $R^1$ and $R^2$ independently of one another, denote hydrogen or an unsubstituted or singly, doubly or triply, identically or differently substituted 5- or 6-membered, aromatic heterocycle, which has 1, 2, 3 or 4 heteroatoms, which are selected from the group consisting of N, O and S, where the aromatic heterocycle can have one, two or three substituents $R_X^1$, which, independently of one another and regardless of their respective occurrence, are selected from the group consisting of the residues hydrogen, Br, F, Cl, I, $C_1$-$C_4$-alkylene-CN, CN, $C_1$-$C_6$-haloalkyl, $C_1$-$C_6$-haloalkoxy, $NO_2$, $C_1$-$C_4$-alkylene-$OR_X^1$, $OR_X^1$, O—$C_1$-$C_4$-alkylene-($C_6$-$C_{10}$)-aryl, O—($C_6$-$C_{10}$)-aryl, O—$C_1$-$C_4$-alkylene-hetaryl, O-hetaryl, $C_1$-$C_4$-alkylene-($C_6$-$C_{10}$)-aryl, ($C_6$-$C_{10}$)-aryl, $C_1$-$C_4$-alkylene-hetaryl, ($C_2$-$C_{10}$)-hetaryl, $C_1$-$C_6$-alkyl, $C_2$-$C_6$-alkenyl, $C_2$-$C_6$-alkynyl, $C_2$-$C_6$-alkenyloxy, $C_2$-$C_6$-alkynyloxy, $C_1$-$C_4$-alkylthio, $C_1$-$C_4$-alkylene-$NR_X^2R_X^3$, $NR_X^2R_X^3$, $C_1$-$C_4$-alkylene-$COR_X^1$, $COR_X^1$, $SO_2R_X^1$, $C_1$-$C_4$-alkylene-$COOR_X^1$, $COOR_X^1$, O—$C_1$-$C_4$-alkylene-$COOR_X^1$, $C_1$-$C_4$-alkylene-$SR_X^1$, $SR_X^1$, $C_1$-$C_4$-alkylene-$C_3$-$C_7$-cycloalkyl, $C_3$-$C_7$-cycloalkyl, $C_1$-$C_4$-alkylene-$C_3$-$C_7$-heterocycloalkyl, $C_3$-$C_7$-heterocycloalkyl, $C_1$-$C_4$-alkylene-$C_3$-$C_7$-heterocycloalkenyl, $C_3$-$C_7$-heterocycloalkenyl, $C_1$-$C_4$-alkylene-$OCOR_X^1$, $OCOR_X^1$, $C_1$-$C_4$-alkylene-$SO_2NR_X^2R_X^3$, $SO_2NR_X^2R_X^3$, $C_1$-$C_4$-alkylene-$CONR_X^2R_X^3$, $CONR_X^2R_X^3$, $C_1$-$C_4$-alkylene-$OCONR_X^2R_X^3$, $C_1$-$C_4$-alkylene-$SOR_X^1$, $C_1$-$C_4$-alkylene-$SO_2R_X^1$, NHCOO—$C_0$-$C_4$-alkylene-($C_6$-$C_{10}$)-aryl or NHCOO—($C_6$-$C_{10}$)-aryl, in which the residues $R_X^1$, $R_X^2$ and $R_X^3$ have the meaning stated above;

Y denotes a residue —(R$^y$)—(Z)—, in which R$^y$ denotes the general formula

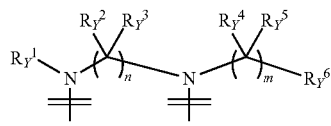

in which

R$_Y^1$, R$_Y^2$ R$_Y^3$ R$_Y^4$, R$_Y^5$ and R$_Y^6$ independently of one another, are selected from the group consisting of H, C$_1$-C$_6$-alkyl and C$_3$-C$_7$-cycloalkyl, n stands for the integer 1, 2 or 3, m stands for the integer 0, 1, 2 or 3, in which the residue R$_Y^1$ plus one of the residues R$_Y^2$ and R$_Y^3$, in each case together with the N or C atom to which they are bound, yield a saturated or unsaturated 4-, 5-, 6- or 7-membered monocyclic ring;

or in which the residue R$_Y^1$ plus one of the residues R$_Y^4$, R$_Y^5$ or R$_Y^6$, in each case together with the N or C atom to which they are bound, yield a saturated or unsaturated 4-, 5-, 6- or 7-membered monocyclic ring;

and/or in which one or two of the residues R$_Y^1$ and R$_Y^2$ with one or two of the residues R$_Y^4$, R$_Y^5$ or R$_Y^6$, in each case together with the N or C atom to which they are bound, yield a saturated or unsaturated mono-, bi- or tricyclic ring structure, which has 4-, 5-, 6- and/or 7-membered ring elements;

or in which the residue R$_Y^1$ plus one of the residues R$_Y^2$ and R$_Y^3$, in each case together with the N or C atom to which they are bound, yield a saturated or unsaturated 4-, 5-, 6- or 7-membered monocyclic ring and in addition one or two of the residues R$_Y^1$ and R$_Y^2$ with one or two of the residues R$_Y^4$, R$_Y^5$ or R$_Y^6$, in each case together with the N or C atom to which they are bound, are joined together in such a way that overall a saturated or unsaturated bi- or tricyclic ring structure is formed, which has 4-, 5-, 6- and/or 7-membered ring members;

or in which the residue R$_Y^1$ plus one of the residues R$_Y^4$ R$_Y^5$ or R$_Y^6$, in each case together with the N or C atom to which they are bound, yield a saturated or unsaturated four-, five-, six- or seven-membered monocyclic ring and in addition one or two of the residues R$_Y^1$ and R$_Y^2$ with one or two of the residues R$_Y^4$ R$_Y^5$ or R$_Y^6$, in each case together with the N or C atom to which they are bound, are joined together in such a way that overall a saturated or unsaturated bi- or tricyclic ring structure is formed, which has 4-, 5-, 6- and/or 7-membered ring members;

where the 4-, 5-, 6- or 7-membered, saturated or unsaturated mono-, bi- or tricyclic ring or the ring structure with 4-, 5-, 6- and/or 7-membered ring members thus formed can in addition have a further heteroatom, selected from the group consisting of O, S and NR$_{YY}^5$, as ring member, where R$_{YY}^5$ regardless of its respective occurrence, can stand for hydrogen, C$_1$-C$_4$-alkyl or C$_3$-C$_7$-cycloalkyl, and where the 4-, 5-, 6- or 7-membered, saturated or unsaturated mono-, bi- or tricyclic ring or the ring structure with 4-, 5-, 6- and/or 7-membered ring members thus formed can have one or two substituents R$_{YY}^6$ and R$_{YY}^7$, which, independently of one another and regardless of their respective occurrence, are selected from the group consisting of the residues C$_1$-C$_6$-alkyl, C$_1$-C$_6$-alkoxy, C$_3$-C$_6$-cycloalkyl, C$_3$-C$_6$-cycloalkoxy, oxo (—C=O), CN, OR$_{YY}^8$, and halogen;

Z is a 5- or 6-membered, saturated or fully or partially unsaturated heterocycle or aromatic heteroaryl ring, which has 1, 2, 3 or 4 heteroatoms, which are selected from the group consisting of N, O and S, where the heterocycle or heteroaryl ring can have one, two or three identical or different substituents R$_Z^1$, which, independently of one another and regardless of their respective occurrence, are selected from the group consisting of the residues C$_1$-C$_6$-alkyl, C$_1$-C$_6$-haloalkyl, C$_1$-C$_6$-alkyloxy, CF$_3$, CHF$_2$, CH$_2$F, C$_1$-C$_6$-haloalkyloxy, OCH$_3$, OCF$_3$, OCHF$_2$, CN, OR$_Z^2$, NR$_Z^3$R$_Z^4$, NSO$_2$—C$_1$-C$_6$-alkyl, NSO$_2$—C$_3$-C$_6$-cycloalkyl, NO$_2$, SR$_Z^5$, SO$_2$R$_Z^5$, SO$_2$NR$_Z^3$R$_Z^4$, CONR$_Z^3$R$_Z^4$, COOR$_Z^5$, COR$_Z^6$, C$_1$-C$_4$-haloalkyloxy, C$_2$-C$_6$-alkenyl, C$_2$-C$_6$-alkynyl, C$_2$-C$_6$-alkenyloxy, C$_2$-C$_6$-alkynyloxy, C$_3$-C$_7$-cycloalkyl, C$_3$-C$_7$-cycloalkyloxy, C$_3$-C$_7$-halocycloalkyloxy and halogen;

in which

R$_Z^1$, R$_Z^2$, R$_Z^3$, R$_Z^4$, R$_Z^5$ and R$_Z^6$ independently of one another and regardless of their respective occurrence, are selected from the group consisting of H, optionally substituted C$_1$-C$_6$-alkyl, optionally substituted C$_3$-C$_7$-cycloalkyl and optionally substituted phenyl, where R$_Z^2$ regardless of its respective occurrence can also be a residue —(CH$_2$)$_p$—COR; or —CO—(CH$_2$)$_p$—CONR$_Z^8$R$_Z^9$, in which R$_Z^7$ regardless of its respective occurrence denotes H, OH, C$_1$-C$_6$-alkyl, C$_1$-C$_6$-alkoxy, C$_3$-C$_7$-cycloalkyl, CH$_2$CH$_2$COOH, NR$_Z^{10}$R$_Z^{11}$, preferably H, CH$_3$, C$_2$H$_5$, isopropyl, cyclohexyl, —CH$_2$CH$_2$COOH, NH$_2$, N(CH$_3$)$_2$; R$_Z^8$ and R$_Z^9$ independently of one another, and their respective occurrence, are selected from the group consisting of H, C$_1$-C$_6$-alkyl and C$_3$-C$_6$-cycloalkyl;

or R$_Z^8$ and R$_Z^9$ regardless of their respective occurrence, together with the nitrogen can form a ring selected from the group consisting of azetidin-1-yl, pyrrolidin-1-yl, piperidin-1-yl, piperazin-1-yl, morpholin-4-yl and thiomorpholin-4-yl;

R$_Z^{10}$ regardless of its respective occurrence denotes H, C$_1$-C$_6$-alkyl, or C$_3$-C$_6$-cycloalkyl;

R$_Z^{11}$ regardless of its respective occurrence denotes H, C$_1$-C$_6$-alkyl, C$_3$-C$_6$-cycloalkyl, —C(CH$_3$)$_2$CH$_2$OH, —C(CH$_3$)(CH$_2$OH)$_2$, or —C(CH$_2$OH)$_3$;

or R$_Z^{10}$ and R$_Z^{11}$ regardless of their respective occurrence, together with the nitrogen can form a ring selected from the group consisting of azetidin-1-yl, pyrrolidin-1-yl, piperidin-1-yl, piperazin-1-yl, morpholin-4-yl and thiomorpholin-4-yl;

R$_Z^3$ regardless of its respective occurrence can also denote a group COR$_Z^{12}$, in which R$_Z^{12}$ regardless of its respective occurrence stands for hydrogen, optionally substituted C$_1$-C$_4$-alkyl or optionally substituted phenyl, or where R$_Z^3$ with R$_Z^4$ regardless of their respective occurrence, can also form jointly a 5- or 6-membered, saturated or unsaturated carbon ring, which can have a heteroatom, selected from the group consisting of O, S, and NR$_Z^{13}$, as ring member, where R$_Z^{13}$ stands for hydrogen or C$_1$-C$_4$-alkyl, p regardless of its respective occurrence, denotes the integer 1 or 2;

a tautomeric, enantiomeric or diastereomeric form thereof, or a physiologically compatible salt thereof.

2. The compound according to claim 1, wherein
B is a phenyl ring, which can be substituted with one or two identical or different residues, which are selected, independently of one another, from the group consisting of chlorine, bromine, iodine, fluorine, CN, $CF_3$, $OCF_3$, $C_1$-$C_6$-alkoxy, $C_1$-$C_6$-haloalkoxy, $C_1$-$C_6$-haloalkyl, $NH_2$, NH—($C_1$-$C_6$-alkyl), N($C_1$-$C_6$-alkyl)($C_1$-$C_6$-alkyl), $C_1$-$C_6$-alkyl, $C_2$-$C_6$-alkenyl, $C_2$-$C_6$-alkynyl, $C_2$-$C_6$-alkenyloxy, $C_2$-$C_6$-alkynyloxy, $C_3$-$C_6$-cycloalkyl, $C_3$-$C_6$-cycloalkoxy, halogenated $C_3$-$C_6$-cycloalkyl and halogenated $C_3$-$C_6$-cycloalkoxy,
a tautomeric, enantiomeric or diastereomeric form thereof, or a physiologically compatible salt thereof.

3. The compound according to claim 1, wherein
B is a phenyl ring, which can be substituted with one or two identical or different residues, which are selected, independently of one another, from the group consisting of hydrogen, chlorine, fluorine, CN, $CH_3$, $OCH_3$, $NH_2$, $NHCH_3$, $N(CH_3)_2$,
a tautomeric, enantiomeric or diastereomeric form thereof, or a physiologically compatible salt thereof.

4. The compound according to claim 1, wherein
B is a residue selected from the group consisting of phenyl, 2-methoxyphenyl, 4-methoxyphenyl, 2,4-dimethoxyphenyl, 3,4-dimethoxyphenyl, 2-methoxy-4-methylphenyl, 2-fluorophenyl, 4-fluorophenyl, 4-chlorophenyl, 2-methoxy-5-fluorophenyl, 2-methoxy-5-methylphenyl, 2-methoxy-4-methoxyphenyl, 2-isobutoxy-5-methoxyphenyl, 2-ethoxy-5-ethylphenyl, 2-ethoxy-4-methoxyphenyl and 4-cyanophenyl,
a tautomeric, enantiomeric or diastereomeric form thereof, or a physiologically compatible salt thereof.

5. The compound according to claim 1, wherein
B is 2,4-dimethoxyphenyl,
a tautomeric, enantiomeric or diastereomeric form thereof, or a physiologically compatible salt thereof.

6. The compound according to claim 1, wherein
$R^1$ and $R^2$, independently of one another, are selected from the group consisting of hydrogen, halogen, F, Cl, Br, I, CN, $C_1$-$C_6$-alkyl, —O—$C_1$-$C_6$-alkyl, $C_3$-$C_6$-cycloalkyl, —O—$C_3$-$C_6$-cycloalkyl, halogenated —O—$C_1$-$C_6$-alkyl, halogenated $C_1$-$C_6$-alkyl, halogenated $C_3$-$C_6$-cycloalkyl, halogenated —O—$C_3$-$C_6$-cycloalkyl and an unsubstituted or singly, doubly or triply, identically or differently substituted 5- or 6-membered, aromatic heterocycle, which has 1, 2, 3 or 4 heteroatoms, which are selected from the group consisting of N, O and S,
a tautomeric, enantiomeric or diastereomeric form thereof, or a physiologically compatible salt thereof.

7. The compound according to claim 1, wherein
$R^1$ and $R^2$, independently of one another, are selected from the group consisting of hydrogen, Cl, CN, $OCH_3$, $CH_3$, and an unsubstituted or singly, doubly or triply, identically or differently substituted 5- or 6-membered, aromatic heterocycle, which has 1, 2, 3 or 4 heteroatoms, which are selected from the group consisting of N, O and S,
a tautomeric, enantiomeric or diastereomeric form thereof, or a physiologically compatible salt thereof.

8. The compound according to claim 1, wherein
$R^1$ is CN and
$R^2$ is hydrogen,
a tautomeric, enantiomeric or diastereomeric form thereof, or a physiologically compatible salt thereof.

9. The compound according to claim 1, wherein
the residue $R^1$ stands in position 5 and is different from hydrogen,
a tautomeric, enantiomeric or diastereomeric form thereof, or a physiologically compatible salt thereof.

10. The compound according to claim 1, wherein
A is a phenyl ring, which is unsubstituted or substituted with one or two identical or different residues, which, independently of one another, are selected from the group consisting of halogen, CN, $NO_2$, $C_1$-$C_4$-alkoxy, $C_1$-$C_6$-alkoxy-$C_1$-$C_6$-alkyl, $C_1$-$C_6$-alkyl, $NH_2$, NH—($C_1$-$C_6$-alkyl), N($C_1$-$C_6$-alkyl)($C_1$-$C_6$-alkyl), ($C_0$-$C_6$-alkyl)-NH—$C_1$-$C_6$-alkylene, ($C_0$-$C_6$-alkyl)($C_1$-$C_6$-alkyl)-N—$C_1$-$C_6$-alkylene, $C_3$-$C_6$-cycloalkyl, $C_3$-$C_6$-cycloalkoxy, $C_1$-$C_6$-haloalkyl, $C_1$-$C_6$-alkylcarbonyl, $C_1$-$C_6$-haloalkylcarbonyl, $C_1$-$C_6$-alkylsulphonyl, $C_1$-$C_6$-haloalkylsulphonyl, $C_1$-$C_6$-haloalkoxy, $C_3$-$C_6$-halocycloalkyl and $C_3$-$C_6$-halocycloalkoxy,
a tautomeric, enantiomeric or diastereomeric form thereof, or a physiologically compatible salt thereof.

11. The compound according to claim 1, wherein
A is a phenyl ring, which is substituted with one or two identical or different residues, which, independently of one another, are selected from the group consisting of fluorine, chlorine, CN, $NH_2$, $CF_3$, $CH_3$, $C_2H_5$, n-$C_3H_7$, i-$C_3H_7$, sec-$C_4H_9$, iso-$C_4H_9$, tert-$C_4H_9$, $C(O)CH_3$, $SO_2CH_3$, $SO_2CF_3$, $OCF_3$, $OCHF_2$, methoxy, ethoxy, methoxymethyl, N,N-dimethylamino-methyl and N-methylamino-methyl,
a tautomeric, enantiomeric or diastereomeric form thereof, or a physiologically compatible salt thereof.

12. The compound according to claim 1, wherein
A is a phenyl ring, which is substituted with one or two identical or different residues, which, independently of one another, are selected from the group consisting of fluorine, chlorine, CN, $NH_2$, $CF_3$, $CH_3$, $C_2H_5$, n-$C_3H_7$, i-$C_3H_7$, sec-$C_4H_9$, iso-$C_4H_9$, tert-$C_4H_9$, $C(O)CH_3$, $SO_2CH_3$, $SO_2CF_3$, $OCF_3$, $OCHF_2$, methoxy, ethoxy, methoxymethyl, N,N-dimethylaminomethyl, N-methylaminomethyl, where if there is a substituent it is disposed in position 2, 3 or 4, and if there are two substituents, one substituent is disposed in position 2 and the other is disposed in position 4 or 5,
a tautomeric, enantiomeric or diastereomeric form thereof, or a physiologically compatible salt thereof.

13. The compound according to claim 1, wherein
A is a phenyl ring, which is substituted with at least one or two residues, which, independently of one another, are selected from the group consisting of 2-fluoro, 4-fluoro, 2-chloro, 4-chloro, 2-methoxy, 2-methyl, 2-ethyl, 3-methoxy, 4-methoxy, 2-ethoxy, 4-ethoxy, 4-trifluoromethyl, 4-difluoromethoxy, 4-trifluoromethoxy, 4-methyl, 4-ethyl, 4-isopropyl, 4-tert-butyl, 4-acetyl, 4-nitro, 4-cyano, 4-methylsulphonyl, 2-methoxymethyl, 4-amino, 3-N,N-dimethylaminomethyl and 3-N-methylaminomethyl,
a tautomeric, enantiomeric or diastereomeric form thereof, or a physiologically compatible salt thereof.

14. The compound according to claim 1, wherein
A is a residue selected from the group consisting of 2-methoxyphenyl, 2-ethoxyphenyl, 2-ethoxy-4-fluoro-phenyl, 2-ethoxy-5-methoxyphenyl, 2-chlorophenyl, 3,4-dimethoxyphenyl, 2,4-dimethoxyphenyl, 2,3-dimethoxyphenyl, 2,5-dimethoxyphenyl, 2-methoxymethylphenyl, 3-N,N-dimethylaminomethylphenyl, 2-methoxy-3-N,N-dimethylaminomethylphenyl and 2-methoxy-3-N-methylaminomethylphenyl, 2,4-difluorophenyl, 2,4-dichlorophenyl, 2-chloro-4-fluorophenyl, 2-fluoro-4-cyanophenyl, 2-chloro-4-trifluoromethylphenyl, 2-methoxy-4-ethoxyphenyl, 4-chloro-2-fluorophenyl, 4-fluoro-2-methylphenyl, 4-tert-butylphenyl, 4-isopropylphenyl, 4-(trifluoromethoxy)phenyl, 4-trifluoromethylphenyl, 4-aminophenyl, 4-methylphenyl, 4-(methylsulphonyl)phenyl, 4-difluoromethoxyphenyl, 4-acetylphenyl, 4-ethoxyphenyl, 2-methoxy-4-nitrophenyl, 2-ethoxy-4-methoxyphenyl, a tautomeric, enantiomeric or diastereomeric form thereof, or a physiologically compatible salt thereof.

15. The compound according to claim 1, wherein

Y denotes a residue selected from the group consisting of the residues Y1 to Y20 stated below

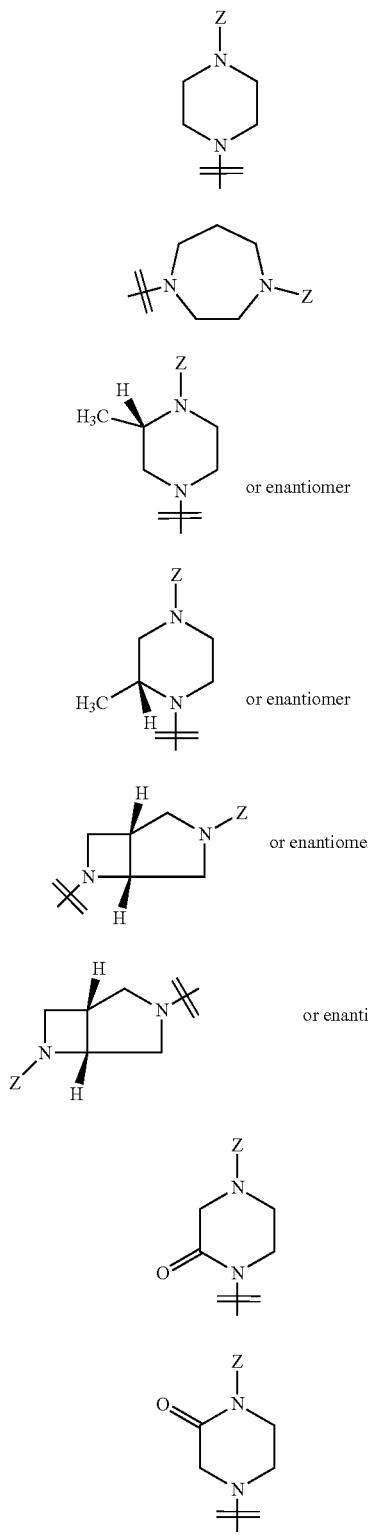
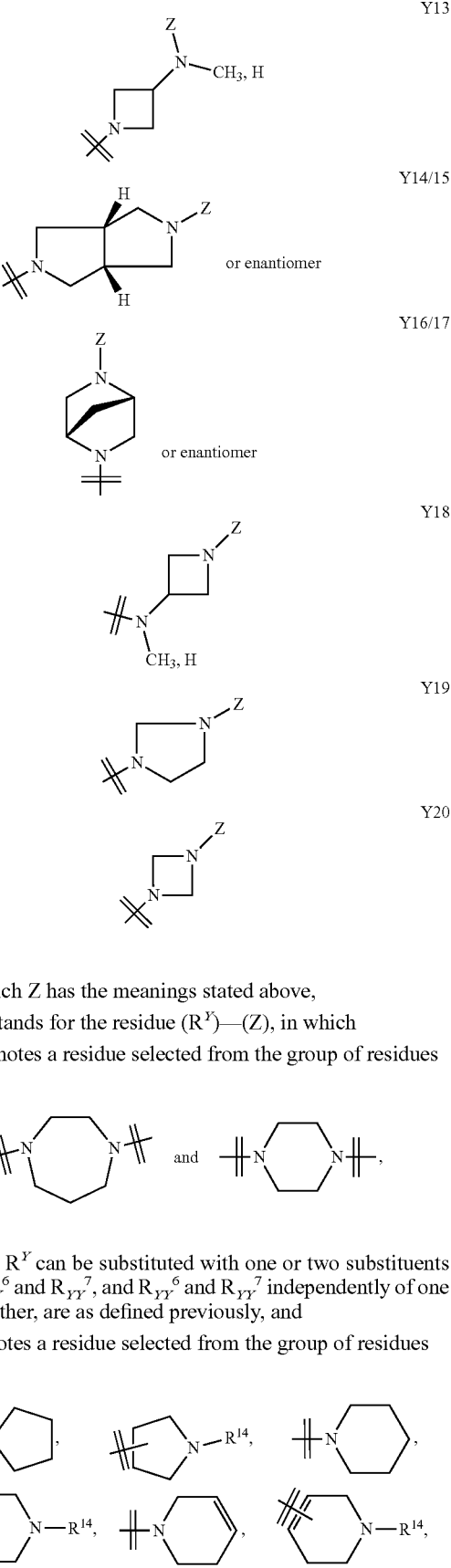

in which Z has the meanings stated above, or Y stands for the residue $(R^Y)$—(Z), in which $R^Y$ denotes a residue selected from the group of residues where $R^Y$ can be substituted with one or two substituents $R_{YY}^6$ and $R_{YY}^7$, and $R_{YY}^6$ and $R_{YY}^7$ independently of one another, are as defined previously, and Z denotes a residue selected from the group of residues

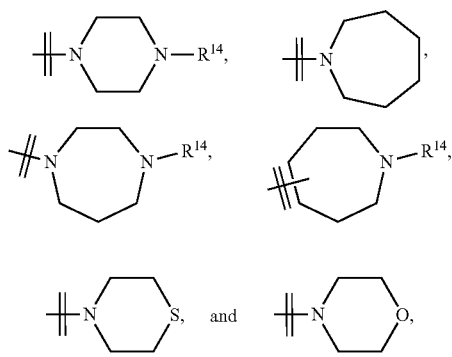

where Z can be substituted with one or two substituents $R_{YY}^6$ and $R_{YY}^7$, and $R_{YY}^6$ and $R_{YY}^7$ independently of one another, and regardless of their occurrence, are as defined previously, and a tautomeric, enantiomeric or diastereomeric form thereof, or a physiologically compatible salt thereof.

16. The compound according to claim 1, wherein

Y denotes a residue selected from the group consisting of the residues Y1 to Y6 and Y14 to Y17 stated below

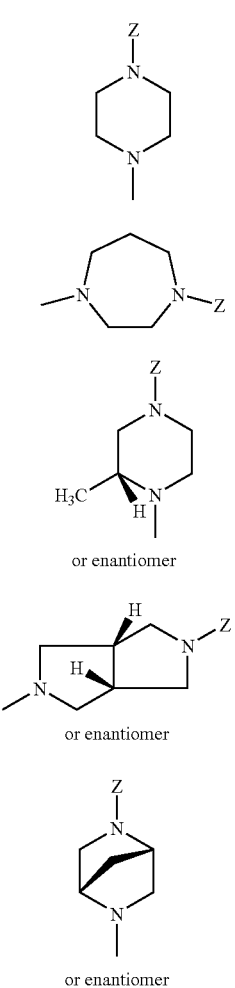

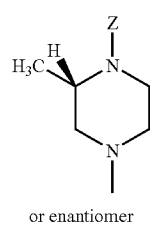

in which Z has the meanings stated above, a tautomeric, enantiomeric or diastereomeric form thereof, or a physiologically compatible salt thereof.

17. The compound according to claim 1, wherein

Z is a 5- or 6-membered, saturated or fully or partially unsaturated heterocycle or aromatic heteroaryl ring, which has 1, 2, 3 or 4 heteroatoms, which are selected from the group consisting of N, O and S, where the heterocycle or heteroaryl ring can have one, two or three identical or different substituents $R_Z^1$, which, independently of one another and regardless of their respective occurrence, are selected from the group consisting of the residues hydrogen, halogen, chlorine, bromine, iodine, fluorine, CN, $CF_3$, $OCF_3$, $NO_2$, OH, O—$C_1$-$C_4$-alkyl, $C_1$-$C_6$-alkyl, O—$C_1$-$C_4$-haloalkyl, $C_1$-$C_6$-haloalkyl, $C_2$-$C_6$-alkenyl, $C_2$-$C_6$-alkynyl, $NH_2$, N-oxide, NH($C_1$-$C_6$-alkyl) and N($C_1$-$C_6$-alkyl)($C_1$-$C_6$-alkyl), a tautomeric, enantiomeric or diastereomeric form thereof, or a physiologically compatible salt thereof.

18. The compound according to claim 1, wherein

Z is a residue selected from the group consisting of 4-pyridyl, 2-pyridyl, 3-pyridyl, 2-triazinyl, 4-pyrimidynyl, 1,3-thiazin-2-yl, which can be substituted with one, two or three identical or different substituents, which, independently of one another, are selected from the group consisting of the residues hydrogen, halogen, chlorine, bromine, iodine, fluorine, CN, $CF_3$, $OCF_3$, $NO_2$, OH, or in each case optionally substituted O—$C_1$-$C_4$-alkyl, $C_1$-$C_6$-alkyl, O—$C_1$-$C_4$-haloalkyl, $C_3$-$C_7$-cycloalkyl, $C_1$-$C_6$-haloalkyl, $C_2$-$C_6$-alkenyl, $C_2$-$C_6$-alkynyl, $NH_2$, N-oxide, NH($C_1$-$C_6$-alkyl) and N($C_1$-$C_6$-alkyl)($C_1$-$C_6$-alkyl), a tautomeric, enantiomeric or diastereomeric form thereof, or a physiologically compatible salt thereof.

19. The compound according to claim 1, wherein

Z is a residue selected from the group consisting of the residues

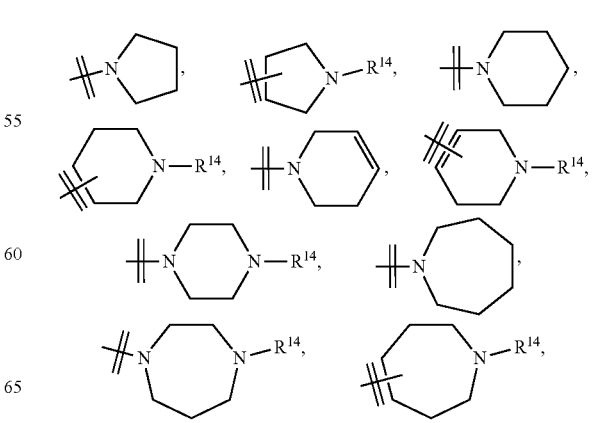

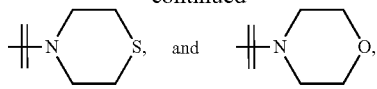

where Z can in addition be substituted with $R_Z^{12}$ and/or $R_Z^{13}$, where $R_Z^{12}$ is hydrogen, $C_1$-$C_6$-alkyl, $C_2$-$C_6$-alkenyl, $C_2$-$C_6$-alkynyl, OH, O—$C_1$-$C_4$-alkyl, O—$C_0$-$C_4$-alkylene-phenyl, $NH_2$, $NH(C_1$-$C_4$-alkyl) or $N(C_1$-$C_4$-alkyl)($C_1$-$C_4$-alkyl), $R_Z^{13}$ is hydrogen, $C_1$-$C_6$-alkyl, $C_2$-$C_6$-alkenyl, $C_2$-$C_6$-alkynyl, OH, O($C_1$-$C_4$-alkyl), O—$C_0$-$C_4$-alkylene-phenyl, $NH_2$, $NH(C_1$-$C_4$-alkyl) or $N(C_1$-$C_4$-alkyl)($C_1$-$C_4$-alkyl), $R^{14}$ is hydrogen, $C_1$-$C_6$-alkyl, $C_2$-$C_6$-alkenyl, $C_2$-$C_6$-alkynyl or $C_0$-$C_4$-alkylene-phenyl a tautomeric, enantiomeric or diastereomeric form thereof, or a physiologically compatible salt thereof.

20. The compound according to claim 1, wherein

Z is a residue selected from the group consisting of 4-pyridyl, 2-pyridyl, 3-pyridyl, 2-triazinyl, 4-pyrimidynyl, 1,3-thiazin-2-yl, which can be substituted with one, two or three identical or different substituents, which, independently of one another, are selected from the group consisting of the residues hydrogen, chlorine, fluorine, CN, methyl, methoxy, ethyl, ethoxy, isopropyl and cyclopropyl, a tautomeric, enantiomeric or diastereomeric form thereof, or a physiologically compatible salt thereof.

21. The compound according to claim 1, wherein

Z is a residue selected from the group consisting of pyridin-4-yl, pyridin-3-yl, pyridin-2-yl, 2-methyl-pyridin-4-yl, 2-ethoxy-pyridin-4-yl, 2-fluoro-pyridin-4-yl, 2-chloro-pyridin-4-yl, 3-methyl-pyridin-4-yl, 3-fluoro-pyridin-4-yl, N-oxopyridin-4-yl, 3,5-dichloropyridin-4-yl, 2-trifluoromethylpyridin-4-yl, 2-isopropylpyridin-4-yl, 2-ethylpyridin-4-yl, 5-cyano-pyridin-4-yl, 1,3-thiazol-2-yl, 1,3,5-triazin-2-yl and 1,3-pyrimidin-4-yl, a tautomeric, enantiomeric or diastereomeric form thereof, or a physiologically compatible salt thereof.

22. The compound according to claim 1, wherein

Z is a residue selected from the group consisting of pyridin-4-yl and 2-methyl-pyridin-4-yl, a tautomeric, enantiomeric or diastereomeric form thereof, or a physiologically compatible salt thereof.

* * * * *

UNITED STATES PATENT AND TRADEMARK OFFICE
CERTIFICATE OF CORRECTION

| | | |
|---|---|---|
| PATENT NO. | : 8,431,567 B2 | Page 1 of 1 |
| APPLICATION NO. | : 12/438696 | |
| DATED | : April 30, 2013 | |
| INVENTOR(S) | : Geneste et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 418 days.

Signed and Sealed this
Thirtieth Day of December, 2014

Michelle K. Lee
*Deputy Director of the United States Patent and Trademark Office*